(12) United States Patent
Yun et al.

(10) Patent No.: US 9,874,531 B2
(45) Date of Patent: Jan. 23, 2018

(54) X-RAY METHOD FOR THE MEASUREMENT, CHARACTERIZATION, AND ANALYSIS OF PERIODIC STRUCTURES

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 105 days.

(21) Appl. No.: 14/712,917

(22) Filed: May 15, 2015

(65) Prior Publication Data

US 2015/0260663 A1    Sep. 17, 2015

Related U.S. Application Data

(63) Continuation-in-part of application No. 14/700,137, filed on Apr. 29, 2015, now Pat. No. 9,719,947,
(Continued)

(51) Int. Cl.
*G01N 23/20* (2006.01)
*G01N 23/201* (2006.01)
(Continued)

(52) U.S. Cl.
CPC ..... *G01N 23/20075* (2013.01); *A61B 6/4007* (2013.01); *A61B 6/4291* (2013.01);
(Continued)

(58) Field of Classification Search
CPC ......... G01N 2223/03; G01N 2223/052; G01N 2223/054; G01N 2223/056;
(Continued)

(56) References Cited

U.S. PATENT DOCUMENTS

| | | | |
|---|---|---|---|
| 2007/0189449 A1* | 8/2007 | Baumann | A61B 6/484 378/44 |
| 2008/0273662 A1* | 11/2008 | Yun | G03F 7/70625 378/74 |
| 2011/0058655 A1* | 3/2011 | Okumura | H01J 35/12 378/143 |

OTHER PUBLICATIONS

Shimura et al., "Hard x-ray phase contrast imaging using a tabletop Talbot-Lau interferometer with multiline embedded x-ray targets", posted Dec. 6, 2012, Optics Letters, vol. 38, No. 2, pp. 157-159.*

(Continued)

*Primary Examiner* — Glen Kao
*Assistant Examiner* — Chih-Cheng Kao
(74) *Attorney, Agent, or Firm* — Bachmann Law Group

(57) ABSTRACT

Periodic spatial patterns of x-ray illumination are used to gather information about periodic objects. The structured illumination may be created using the interaction of a coherent or partially coherent x-ray source with a beam splitting grating to create a Talbot interference pattern with periodic structure. The object having periodic structures to be measured is then placed into the structured illumination, and the ensemble of signals from the multiple illumination spots is analyzed to determine various properties of the object and its structures. Applications to x-ray absorption/transmission, small angle x-ray scattering, x-ray fluorescence, x-ray reflectance, and x-ray diffraction are all possible using the method of the invention.

13 Claims, 43 Drawing Sheets

Related U.S. Application Data which is a continuation-in-part of application No. 14/527,523, filed on Oct. 29, 2014, now abandoned.

(60) Provisional application No. 61/987,106, filed on May 1, 2014, provisional application No. 61/989,743, filed on May 7, 2014, provisional application No. 61/991,889, filed on May 12, 2014, provisional application No. 61/993,811, filed on May 15, 2014, provisional application No. 61/898,019, filed on Oct. 31, 2013, provisional application No. 61/901,361, filed on Nov. 7, 2013, provisional application No. 61/981,098, filed on Apr. 17, 2014, provisional application No. 61/993,792, filed on May 15, 2014.

(51) Int. Cl.
*A61B 6/00* (2006.01)
*G21K 1/02* (2006.01)
*H01J 35/08* (2006.01)

(52) U.S. Cl.
CPC ............ *A61B 6/484* (2013.01); *A61B 6/508* (2013.01); *G01N 23/201* (2013.01); *G21K 1/02* (2013.01); *H01J 35/08* (2013.01); *G21K 2207/005* (2013.01); *H01J 2235/086* (2013.01)

(58) Field of Classification Search
CPC ....... G01N 2223/076; G01N 23/20075; G01N 23/201; A61B 6/4007; A61B 6/4291; A61B 6/484; A61B 6/508; G21K 1/02; G21K 2207/005; H01J 2235/086; H01J 35/08

See application file for complete search history.

(56) References Cited

OTHER PUBLICATIONS

Momose et al., "X-ray Phase Imaging with Talbot Interferometry", 2009, Biomedical Mathematics: Promising Directions in Imaging, Therapy Planning, and Inverse Problems (Medical Physics Publishing, Madison Wis., 2010), pp. 281-320.*

Weitkamp et al., "Design Aspects of X-ray Grating Interferometry", Conference presentation date Mar. 2012, International Workshop on X-ray and Neutron Phase Imaging with Gratings, AIP Conf. Proc. 1466, pp. 84-89.*

Weitkamp et al., "Tomography with grating interferometers at low-brilliance sources", 2006, SPIE, vol. 6318, pp. 0S-1 to 0S-10.*

Morimoto et al., "X-ray phase contrast imaging by compact Talbot-Lau interferometer with a signal transmission grating", Jul. 16, 2014, Optics Letters, vol. 39, No. 15, pp. 4297-4300.*

* cited by examiner

US 9,874,531 B2

X-RAY METHOD FOR THE MEASUREMENT, CHARACTERIZATION, AND ANALYSIS OF PERIODIC STRUCTURES

CROSS-REFERENCE TO RELATED APPLICATIONS

This Patent Application is a continuation-in-part of U.S. patent application Ser. No. 14/700,137, filed Apr. 29, 2015 and entitled "X-RAY INTERFEROMETRIC IMAGING SYSTEM", which in turn is a continuation-in-part of U.S. patent application Ser. No. 14/527,523, filed Oct. 29, 2014 and entitled "X-RAY INTERFEROMETRIC IMAGING SYSTEM", which claims the benefit of U.S. Provisional Patent Application Nos. 61/898,019, entitled "X-ray Phase Contrast imaging System" and filed on Oct. 31, 2013; 61/901,361, entitled "An X-ray Source Consisting of an Array of Fine Sub-Sources" and filed on Nov. 7, 2013; and 61/981,098 entitled "Two Dimensional Phase Contrast Imaging Apparatus" and filed Apr. 17, 2014, all of which are incorporated herein by reference in their entirety. U.S. patent application Ser. No. 14/700,137, for which the present Application is a continuation-in-part, additionally claims the benefit of U.S. Provisional Patent Application No. 61/987,106, filed on May 1, 2014 and entitled "METHODS OF REDUCING SCATTER RADIATION USING TALBOT EFFECT"; 61/989,743, filed on May 7, 2014 and entitled "Methods of Improving Detector MTF and DQE and Reducing Scatter Background of an X-ray Imaging System Using Coherence Effect"; 61/991,889, filed May 12, 2014 and entitled "Method of Single-Shot Imaging to Obtain Absorption and Differential Phase, and/or Scattering, and/or Phase Contrast Images"; 61/993,811, filed May 15, 2014 and entitled "Method of Talbot Effect based X-ray Imaging with High Image Contrast and Design of Apparatus Using Such", all of which are incorporated herein by reference in their entirety. The present Application additionally claims the benefit of U.S. Provisional Patent Application 61/993,792, filed May 15, 2014 and entitled "Method of Talbot-Effect Based X-ray Patterned Probe and Characterization (Metrology or Inspection) Apparatuses Using Such", which is also incorporated herein by reference in its entirety.

FIELD OF THE INVENTION

The embodiments of the invention disclosed herein relate to interferometric systems using x-rays, and in particular, interferometric measurement, characterization and analysis systems for observing period structures. The system uses high-brightness coherent sources of x-rays, which in turn may use anodes or targets comprising periodic microstructures of x-ray generating materials embedded in a thermally conducting substrate of low atomic number material.

BACKGROUND OF THE INVENTION

The initial discovery of x-rays by Röntgen in 1895 [W. C. Röntgen, "Eine Neue Art von Strahlen" (Wurzburg Verlag, 1896); "On a New Kind of Rays," *Nature*, Vol. 53, pp. 274-276 (Jan. 23, 1896)] occurred when Röntgen was experimenting with electron bombardment of targets in vacuum tubes. The contrast between the absorption from bone containing calcium (atomic number Z=20) and soft tissue containing mostly carbon (Z=6), was immediately apparent because the absorption difference between the two materials at x-ray energies between 5 and 30 keV can differ by a factor of 10 or more, as illustrated in FIG. 1. These high energy, short wavelength photons are now routinely used for medical applications and diagnostic evaluations, as well as for security screening, industrial inspection, quality control and failure analysis, and for scientific applications such as crystallography, tomography, x-ray fluorescence analysis and the like.

Although x-ray shadowgraphs have become a standard medical diagnostic tool, there are problems with simple absorption contrast imaging. Notably, for tests such as mammograms, variations in biological tissue may result in only a subtle x-ray absorption image contrast, making unambiguous detection of tumors or anomalous tissue difficult.

In the past decade, a new kind of x-ray imaging methodology has emerged, based on x-ray phase contrast interferometry. The method relies on the well-known Talbot interference effect, originally observed in 1837 [H. F. Talbot, "Facts relating to optical science No. IV", *Philos. Mag.* vol. 9, pp. 401-407, 1836] and fully explained by Lord Rayleigh in 1881 [Lord Rayleigh, "On copying diffraction gratings and some phenomena connected therewith," *Philos. Mag.* vol. 11, pp. 196-205 (1881)].

This effect is illustrated in FIG. 2. For an absorbing grating G of period p, the diffraction pattern from a monochromatic beam of a wavelength $\lambda$ with sufficient coherence forms a repeating interference pattern that reconstructs the original grating pattern, (known as a "self-image") at multiples of a distance known as the Talbot Distance $D_T$. For the case when the incident beam is a plane wave (equivalent to a source located at infinity from the grating G), $D_T$ is given by:

$$D_T = \frac{2p^2}{\lambda} \qquad \text{[Eqn. 1]}$$

Between the grating G and the Talbot Distance, other periodic interference patterns emerge as well. The periodicity and the position of the Talbot fringes depend on the transmission properties of the grating G, including amount of phase-shift and percent of absorption, and grating line-to-space (opening) ratio, or duty factor. For example, for a periodic absorption grating, a fringe pattern that reconstructs the original grating pattern with a lateral shift by half the grating period occurs at half the Talbot Distance $D_T/2$, and a fringe pattern with a period of half of the original grating period occurs at one quarter of the Talbot Distance $D_T/4$ and at three quarters of the Talbot Distance $3D_T/4$, as illustrated in FIG. 2. These 2-D interference patterns are sometimes called a "Talbot Carpet" because of the resemblance of these complex patterns to ornate oriental carpets. [Note: this image of an Optical Talbot Carpet in FIG. 2 is adapted from a file created by Ben Goodman and available at commons.wikimedia.org/wiki/File:Optical_Talbot_Carpet.png.]

FIGS. 3 and 4 illustrate a prior art Talbot interferometric comprising a partially coherent source 200 (shown as a microfocus source) of x-rays 288 and a beam splitting grating $G_1$ 210 of period $p_1$ that establishes a set of Talbot interference fringe patterns 289. It should be noted that the coherence length of the x-ray source is preferably set to be comparable to or larger than the period $p_1$ of the beam splitting grating $G_1$ 210, so that the Talbot interference fringes will have high contrast (Talbot fringes may be well defined if the fringe contrast is, for example, greater than 20%). The beam splitting grating 210 may be an amplitude (also known an absorption or transmission) grating, creating intensity fringes as illustrated in FIG. 2, but is more typically a phase grating for efficient use of the illuminating x-rays, introducing periodic phase-shifts to the x-ray pattern that also form periodic Talbot fringes 289. Henceforth in this application, a transmission grating will be used to describe gratings in which the x-ray transmission through the grating lines is less than 10% and a phase grating will be used to describe gratings in which the phase shift through the grating lines is a fraction (e.g. ½) or odd integer multiple of π.

The Talbot fringes 289 are detected using an x-ray detector 290, preferably with a spatial resolution equal to or better than one third of the Talbot fringe period and having a high x-ray quantum detection efficiency. The detector 290 transforms the x-ray intensity pattern into electronic signals that are transmitted over a connector 291 to an image processing system 295. When an object is placed in the beam path, the image processing system 295 is used to process the x-ray intensity pattern intensity information 298 to obtain absorption, phase, and scattering contrast images.

In practice, the spatial resolution of the detector 290 (such as a flat panel detector, or a charge coupled device (CCD) detector coupled with a scintillator that converts x-rays to visible light) is often on the order of tens of micrometers or larger, and the Talbot fringes 289 may be too fine to detect directly with the detector 290. In this case, an analyzer grating $G_2$ 220 of period $p_2$ is often used to produce Moiré fringes. To record a complete set of images, the analyzer grating $G_2$ 220 will be moved in predetermined distances orthogonal to the grating period and relative to the detector to collect multiple interference patterns in a process called "phase-stepping", or less commonly, rotated at a small angle relative to $G_1$ to obtain a Moiré pattern in a single-shot image for Fourier analysis. The image(s) are then processed to reconstruct the wavefront and determine the shapes, structures, and composition of the objects that created them.

It should also be noted that, instead of physically moving the analyzer grating 220, the position of the x-ray source may also be displaced to create a translation of the interference images that allows the collection of phase-shift information. This can be accomplished electronically by moving the position of the electron beam that bombards the x-ray generating material that serves as the source for the x-rays [see, for example, H. Miao et al., "Motionless phase stepping in X-ray phase contrast imaging with a compact source", *Proceedings of the National Academy of Sciences*, vol. 110(48) pp. 19268-19272, 2013] or by physically moving the x-ray source relative to a fixed position of the analyzer grating 220.

These grating-based x-ray phase-contrast imaging (XPCI) techniques are generally referred to as "grating-based interferometry" (GBI).

As illustrated so far, the grating interferometer only produces interference fringes, and the analysis of these fringes will reveal the structure of the already known grating $G_1$ 210 or the wavefront of the illumination beam. However, when an object is introduced in the path of the x-ray beam, variations in the wavefront introduced by the object result in corresponding changes in the pattern of the Talbot interference fringes, generally known as Moiré fringes. Interferometric image reconstruction techniques may then be used to analyze the wavefront and reconstruct images representing the structure of the unknown object.

In FIG. 5, the prior art Talbot interferometer of FIGS. 3 and 4 is illustrated being used as an imaging technique for a biological sample, in this case, a mouse 240-M, placed between the source 200 and the beam splitting grating $G_1$ 210. The x-rays 288 from the coherent source 200 pass through the mouse 240-M and the beam splitting grating $G_1$ 210 and create a perturbed set of Talbot fringes 289-M. The local phase shifts create angular deviations that translate into changes of locally transmitted intensity when analyzed by the analyzer grating $G_2$ 220 and detector 290. Collecting multiple images from the x-ray detector 290 for situations where the analyzer grating $G_2$ 220 has been displaced by multiple predetermined positions allow a recording of the interference pattern 289-M.

As before, the detector 290 transforms the x-ray intensity pattern into electronic signals that are transmitted over a connector 291 to an image processing system 295 used to produce one or more images 298-M with absorption, differential phase, phase, and scattering contrast information. Numerical processing of the images, including images collected by the system with and without the object under investigation, can be used to infer the shapes and structure of the objects that created them, including objects such as the mouse 240-M. The recorded intensity oscillations can be represented by a Fourier series, and with the proper image processing algorithms, differential phase shift and absorption signals can be extracted, and images corresponding to x-ray absorption, phase contrast, and scattering by the object can be synthesized. [See, for example, A. Momose et al., "Demonstration of x-ray Talbot interferometry", *Jpn. J. Appl. Phys.* vol. 42, pp. L866-L868, 2003; A. Momose, U.S. Pat. No. 7,180,979, issued Feb. 20, 2007; T. Weitkamp et al. "Hard X-ray phase imaging and tomography with a grating interferometer", *Proc. SPIE* vol 5535, pp. 137-142, 2004, and "X-ray phase imaging with a grating interferometer", *Optics Express* vol. 13(16), pp. 6296-6304, 2005; and C. Kottler & R. Kaufmann, U.S. Pat. No. 7,924,973.]

It should be noted that other configurations exist in which the object, such as a mouse 240-M, can be placed between the beam splitting grating $G_1$ 210-A and the analyzer grating $G_2$ 220 and detector 290, as illustrated in FIG. 6. Other configurations using various phase and amplitude gratings, or using detector 290 with higher resolution pixels without the analyzer grating 220, may also be known to those skilled in the art.

Aside from imaging the anatomy of mice, clinical applications of phase-contrast x-ray imaging may be found in mammography, where the density of cancerous tissue may have a distinct phase signature from healthy tissue [see, for example, J. Keyriläinen et al., "Phase contrast X-ray imaging of breast", *Acta Radiologica* vol. 51 (8) pp. 866-884, 2010], or for bone diseases like osteoporosis or osteoarthritis, in which the angular orientation of the bone structures may be an early indicator of bone disease [see, for example, P. Coan et al., "In vivo x-ray phase contrast analyzer-based imaging for longitudinal osteoarthritis studies in guinea pigs", *Phys. Med. Biol.* vol. 55(24), pp. 7649-62, 2010].

However, for the prior art configurations described so far, x-ray power is a problem. An x-ray source with a full-width half maximum diameter S given by $$S \le \frac{\lambda L}{2\pi p_1} \qquad \text{[Eqn. 2]}$$

where $p_1$ is the period of the beam splitting grating $G_1$ 210 and L the distance between the source 200 and the beam splitting grating $G_1$ 210, is required for the technique to produce high contrast fringes and Moiré patterns. For practical applications and system geometries, this implies a microfocus source. However, electron bombardment of the target also causes heating, and the x-ray power that can be achieved is limited by the maximum total electron power that can fall on the microspot without melting the x-ray generating material. A limited electron power means a limited x-ray power, and the low x-ray flux achievable with typical x-ray targets may lead to unacceptable long exposure times when used, for example, for mammography or other diagnostic tests involving live patients or animals. The total x-ray flux can be increased by distributing higher electron power over a larger area, but then the source becomes less coherent, degrading the image contrast.

Coherent x-rays of higher brightness and sufficient flux can be achieved by using a synchrotron or free-electron laser x-ray source, but these machines may occupy facilities that cover acres of land, and are impractical for use in clinical environments.

One innovation that has been shown to enable greater x-ray power employs an additional grating $G_0$ [see, for example, John F. Clauser, U.S. Pat. No. 5,812,629, issued Sep. 22, 1998]. Such a system is illustrated in FIG. 7. In this configuration, a source grating $G_0$ 308 with period $p_0$, which is typically an x-ray transmission grating, is used in front of an x-ray source 300. In this case, the x-ray source may be a high-power extended source with a large incident electron beam area (and not a microfocus source) that produces a higher total flux of x-rays.

The x-rays 388 pass through the grating $G_0$ 308 and emerge from the grating apertures as an array of individually spatially coherent (similar to a microfocus source described above) but mutually incoherent sub-sources of illumination for the beam splitting grating $G_1$. To ensure that each x-ray sub-source in $G_0$ contributes constructively to the image-formation process, the geometry of the setup should satisfy the condition:

$$p_0 = p_2 \frac{L}{D} \qquad \text{[Eqn. 3]}$$

When the condition is met, the x-rays from the many apertures of $G_0$ produce the same (overlapping) Talbot interference pattern, and because the various mutually incoherent sources do not interfere with each other, these Talbot patterns will add as intensities. The effect at the detector 290 is therefore to simply increasing the signal (along with it the signal-to-noise ratio) over what a single coherent source can provide.

This configuration is called the Talbot-Lau interferometer [see Franz Pfeiffer et al., "Phase retrieval and differential phase-contrast imaging with low-brilliance X-ray sources", *Nature Physics* vol. 2, pp. 258-261, 2006; and also Described in U.S. Pat. No. 7,889,838 by Christian David, Franz Pfeiffer and Timm Weitkamp, issued Feb. 15, 2011].

FIG. 8 illustrates an example of periodic structures in an object (an IC or silicon wafer) that may be examined using the methods of the invention disclosed herein. This illustration (published in of Victor Vartanian et al., "Metrology needs for through-silicon via fabrication", in J. Micro/ Nanolith. MEMS MOEMS vol. 13(1), 011206 (January-March 2014), FIG. 6) shows a cross section of copper through silicon vias (TSVs) that have been fabricated with voids in the center of the TSV.

Unfortunately, the current art of Talbot-Lau GBIs have many constraints for most practical applications such as semiconductor device inspection, including a requirement that both the source grating $G_0$ and the analyzer grating $G_2$ have fine pitches and apertures with large aspect ratios.

The requirement for the source grating $G_0$ is to create fine individual well-separated x-ray sub-sources to minimize the reduction in image contrast due to unwanted transmission of x-rays through the aperture defining structures. However, for a 1:1 line-to-space ratio grating, simple x-ray shadowing dictates that the x-ray transmission through the grating is limited to less than 50%, and is reduced further when the angular shadowing (limiting the angular range of the x-rays from the source to reach the object) is included. Furthermore, the optimal line-to-space ratio for $G_0$ that reduces the radiation dose to the object (which is important to preclinical and clinical imaging applications) is closer to 3:1 rather than 1:1. In this case, about 75% of the x-rays from the source are blocked due to area shadowing alone, and when gratings with large aspect ratios are used, greater losses occur due to angular shadowing.

The requirement for the analyzer grating $G_2$ is to be able to sample the Talbot interference fringes with sufficient resolution without losing contrast. As a result, both the $G_0$ and $G_2$ gratings must have small apertures and be of thickness sufficient to minimize unwanted x-ray transmission, which limits the efficient use of the x-rays from the source. Furthermore, the loss from the analyzer grating $G_2$ further results in a significantly higher dose (relative to the same system without a $G_2$ grating) for the object under investigation to produce an image with good characteristics due to multiple exposures for phase-stepping and absorption of x-rays resulting in lower signal-to-noise. When the object under investigation is a live animal or human, higher doses of ionizing radiation are undesirable and generally discouraged.

If the aperture dimensions of the grating $G_0$ are larger, angular collimation can be reduced (although not the area shadowing) so that x-ray transmission is not reduced as severely, but this reduces the spatial coherence length of the x-ray beam downstream from the apertures, and leads a reduction in image contrast. Smaller apertures can increase the possible image contrast and resolution by improving spatial coherence, but decreases the overall number of x-rays in the system, thus requiring longer exposure times. Moreover, with smaller apertures, these fine gratings become more difficult to manufacture.

The problem is exacerbated when attempting to use a Talbot-Lau interferometer for higher energy x-rays, which are often desired to obtain sufficient transmission through an object and to reduce radiation dose. In general, as was illustrated in FIG. 1, the absorption of x-rays for biological tissue is far lower for x-rays with energy greater than 5 keV, and the use of higher energy x-rays will reduce the absorbed dose of potentially harmful ionizing radiation by orders of magnitude. However, 5 keV photons have a wavelength of 0.248 nm, and 50 keV have a wavelength 10 times smaller (0.0248 nm). Furthermore, building absorbing gratings such as $G_0$ and $G_2$ for these higher-energy, shorter-wavelength x-rays can present difficulties, as the thickness of the gratings must increase exponentially to maintain the same absorption factor for higher energy x-rays (the x-ray attenuation length is approximately proportional to $E_{kev}^3$).

The preceding problems of Talbot-Lau GBIs using linear gratings, which can be used for collecting interference data in one dimension only, become more severe if one wishes to generate phase-contrast images in two orthogonal directions. This is often required to make the image reconstruction robust and images more understandable, and because features parallel to the grating lines in the 1-D case are typically less accurately measured. One simple approach is to perform XPCI in two orthogonal directions and then subsequently register the two datasets properly. In addition to challenges associated with the imaging and registration processes, this approach may not be practical, especially when used with living subjects who may move or simply become impatient, and who will incur increased dosage (doubled) if the phase stepping must be performed in two directions. Simultaneous two-dimensional XPCI would be desirable, especially if data collection in a single exposure (shot) and at high x-ray energies is possible to reduce exposure times and the absorbed dosage.

There is therefore a need for an x-ray interferometric imaging system that offers the resolution and detection capabilities of the Talbot-Lau interferometer, but employing a brighter compact source of x-rays and, ideally, a brighter source of higher energy x-rays, especially one that could provide simultaneous two-dimensional phase-contrast imaging.

BRIEF SUMMARY OF THE INVENTION

We disclose here an x-ray interferometric method for the measurement, characterization and analysis of objects containing periodic structures. Periodic spatial patterns of x-ray illumination are used to gather information about periodic objects. The structured illumination may be created using the interaction of a coherent or partially coherent x-ray source with a beam splitting grating to create a Talbot interference pattern with periodic structure. The object having periodic structures to be measured is then placed into and aligned with the structured illumination, and the ensemble of signals from the multiple illumination spots is analyzed to determine various properties of the object and its structures. Applications to x-ray absorption/transmission, small angle x-ray scattering, x-ray fluorescence, x-ray reflectance, and x-ray diffraction are all possible using the method of the invention.

Although embodiments may be implemented with a number of different x-ray sources, one embodiment may use a array source in which the x-ray source comprises a target having a plurality of micro structured x-ray generating materials arranged within a periodic array pattern to form periodic sub-sources of x-rays. The system additionally comprises a beam-splitting grating $G_1$ that creates a Talbot interference pattern, and an x-ray detector to convert two-dimensional x-ray intensities into electronic signals.

The use of structured illumination in the form of a Talbot interference pattern to illuminate a periodic object may be carried out using a beam splitting grating $G_1$ designed to produce interference patterns at the same pitch and feature size as the periodic features in the object to be examined. Different gratings $G_1$ may be used in conjunction with different objects. The gratings $G_1$ may be fabricated as lithographically produced microstructures in silicon, and may comprise 1-D structures, 2-D structures, or combinations thereof.

In some embodiments, the x-ray source target comprises a plurality of microstructures of x-ray generating materials (such as molybdenum or tungsten) in close thermal contact with a thermally conducting substrate of a low atomic number material, such as diamond or beryllium. The x-ray generating microstructures may be arranged in a periodic pattern, with each periodic element of the pattern corresponding to a single discrete microstructure or alternatively, with each periodic element of the pattern comprising multiple discrete microstructures. One or more sources of electrons bombard the plurality of x-ray generating materials, which are generally arranged within a periodic array, so that the x-ray generated from each periodic array element serves as an individually coherent sub-source of x-rays of illumination for the beam splitting grating $G_1$. In some embodiments, the microstructures have lateral dimensions measured on the order of microns, and with a thickness on the order of one half of the electron penetration depth within the substrate material. In some embodiments, the microstructures are formed in a regular two-dimensional array.

A particular advantage of the invention is that high x-ray brightness and large x-ray power may be achieved by using an x-ray target in which the microstructures of a high Z material are in close thermal contact with, or embedded in, a substrate of low Z material and high thermal conductivity, such as beryllium or diamond. The ability of the substrate to draw heat away from the x-ray generating material allows higher electron density and power to be used, generating greater x-ray brightness and power from each of the sub-sources. This results in the creation of individual, well-separated spatially coherent x-ray sub-sources from the high Z material, while the use of a substrate with low Z and low mass density minimizes the production of x-rays from the substrate that can lead to a reduction in image contrast.

Figure 1:
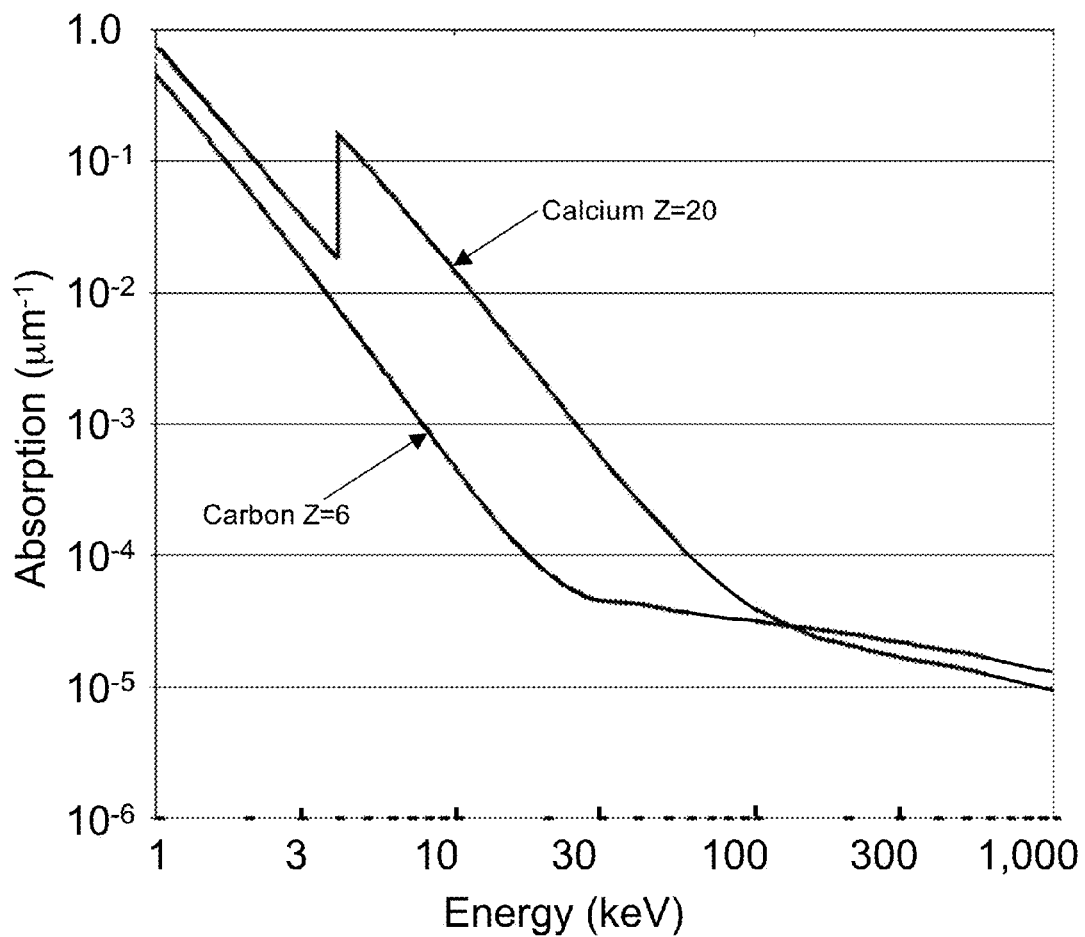
FIG. 1 illustrates a plot of the x-ray absorption of carbon and calcium as a function of x-ray energy.

Note: The illustrations in the Drawings disclosed in this application are typically not shown to scale, and are meant to illustrate the principle of the invention and its function only, and not specific relationships between the microstructures in the target and the various grating periods $p_1$, $p_2$, $p_3$, $p_4$, $p_5$ and $p_6$. Please refer to the descriptions in the text of the Specification for specific details of the dimensions of these objects.

DETAILED DESCRIPTIONS OF EMBODIMENTS OF THE INVENTION

Descriptions of Various Embodiments of the Invention

Figure 9:
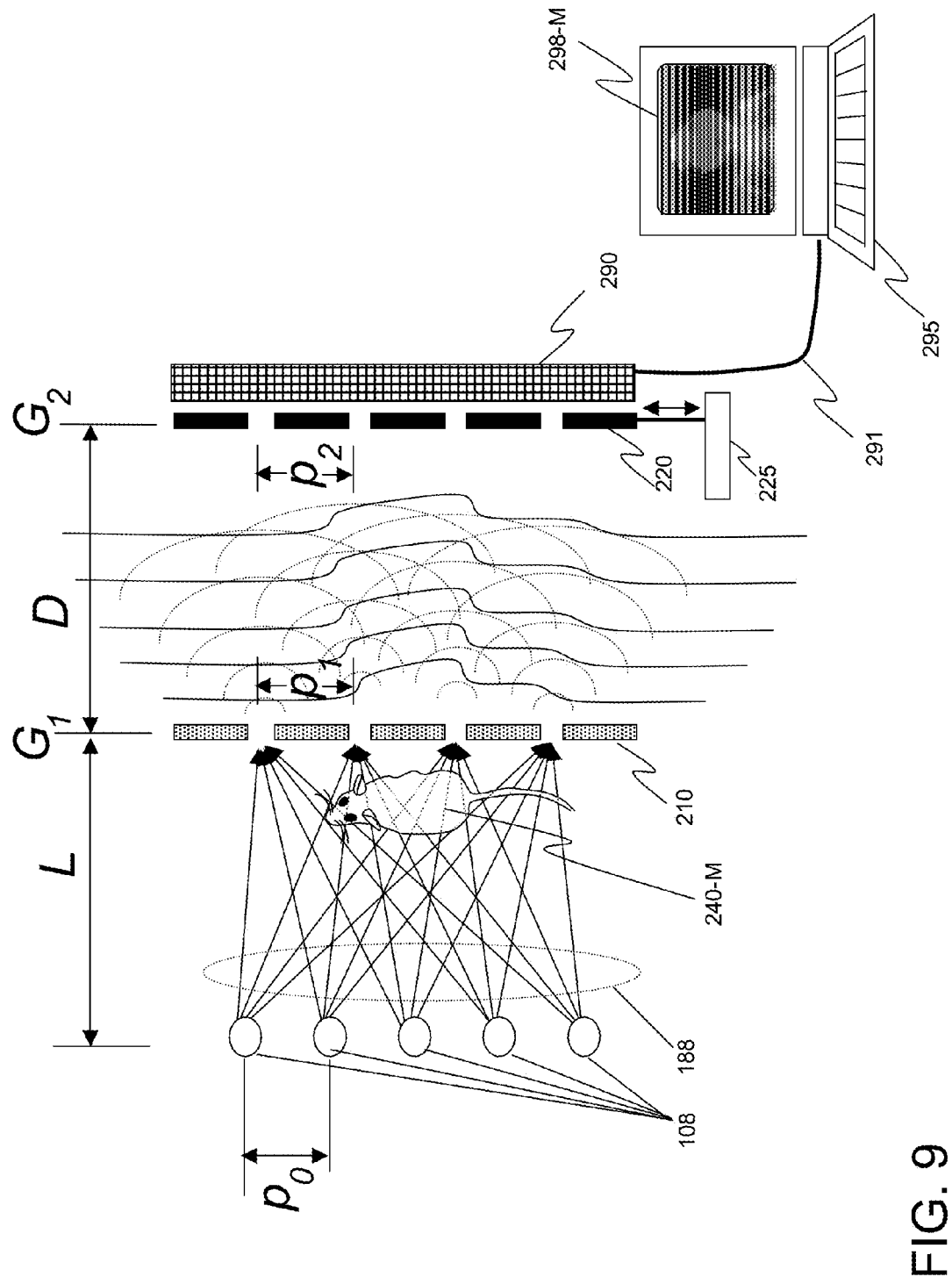
FIG. 9 illustrates a schematic cross-section view of an embodiment of an x-ray interferometric imaging system according to the invention.

One embodiment of the invention disclosed herein is an x-ray phase-contrast imaging (XPCI) system as illustrated in FIG. 9. The system bears some similarity to the prior art Talbot-Lau interferometer, in that it comprises a beam splitting grating $G_1$ 210 of period $p_1$ that establishes a Talbot interference pattern, and an x-ray detector 290 typically comprising an array of sensors to convert two-dimensional x-ray intensities into electronic signals.

The beam splitting grating $G_1$ 210 may be a phase grating or a transmission grating, and may comprise 1-D periodic patterns (linear gratings), or may comprise more complex 2-D structures such as a grid that is periodic in two orthogonal directions.

The system may also comprise an analyzer grating $G_2$ 220 of period $p_2$ that may be placed in front of the detector to form additional interference fringes, such as Moiré fringes. The system may additionally comprise a means 225 to translate the analyzer grating $G_2$ 220 relative to the detector, and a connector 291 to transmit electronic signals corresponding to the detected x-ray intensity to an image processing system 295 for processing.

However, instead of using an extended x-ray source and an additional grating $G_0$ to create a plurality of x-ray source spots, as was done in the Talbot-Lau system, the embodiments of the present invention use an x-ray source comprising a plurality of x-ray generating sub-sources 108 arranged in a periodic array that generate x-rays 188 from electron beam bombardment, such that each sub-source is individually coherent, but together function as a set of mutually incoherent or partially coherent sub-sources of illumination for the beam splitting grating $G_1$. As with the combination of the extended x-ray source and the source grating of the Talbot-Lau interferometer, these sub-sources 108 form the Talbot interference fringe patterns that are created by the beam splitting grating $G_1$ 210 and perturbed by an object 240-M, and may be recorded by detector 290. If the spatial resolution of the detector 290 has a spatial resolution equal to or better than one third of the Talbot fringe period, the detector may record the fringes directly. If a lower resolution detector is used, an analyzer grating $G_2$ 220 may also be used to create Moiré fringes, as was described for the Talbot-Lau interferometer.

The plurality of discrete x-ray sub-sources can be considerably brighter than the x-ray source of the Talbot-Lau system. Because the source comprises sub-sources that are self-coherent but may be mutually incoherent, there is no need for an attenuating transmission grating $G_0$ to create an array of sub-sources from an extended x-ray source.

A system according to the invention comprising multiple sub-sources in a structured target may be designated a Talbot-ST interferometer.

Figure 10:
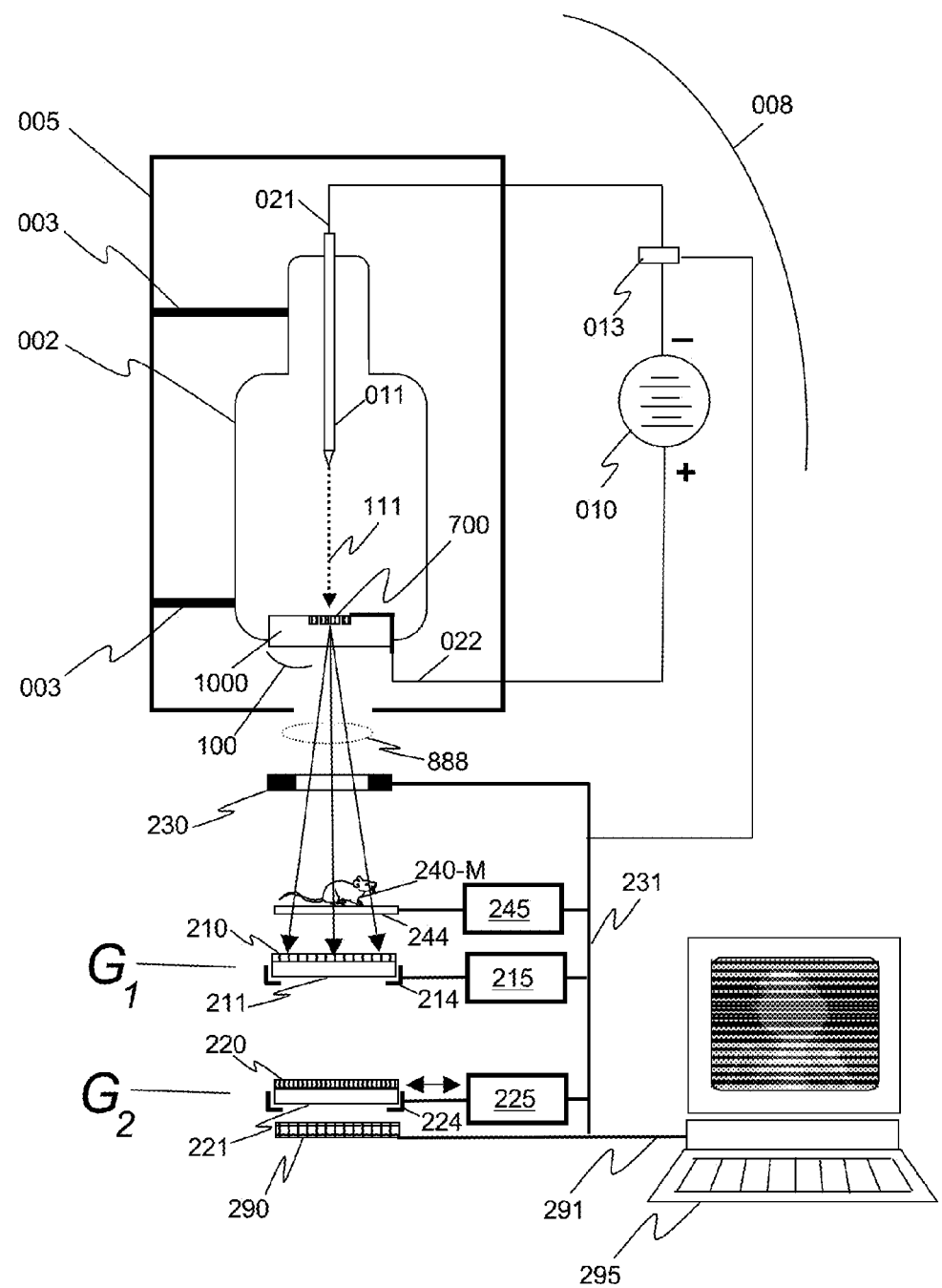
FIG. 10 illustrates a schematic cross-section view of an embodiment of the invention.
Figure 11:
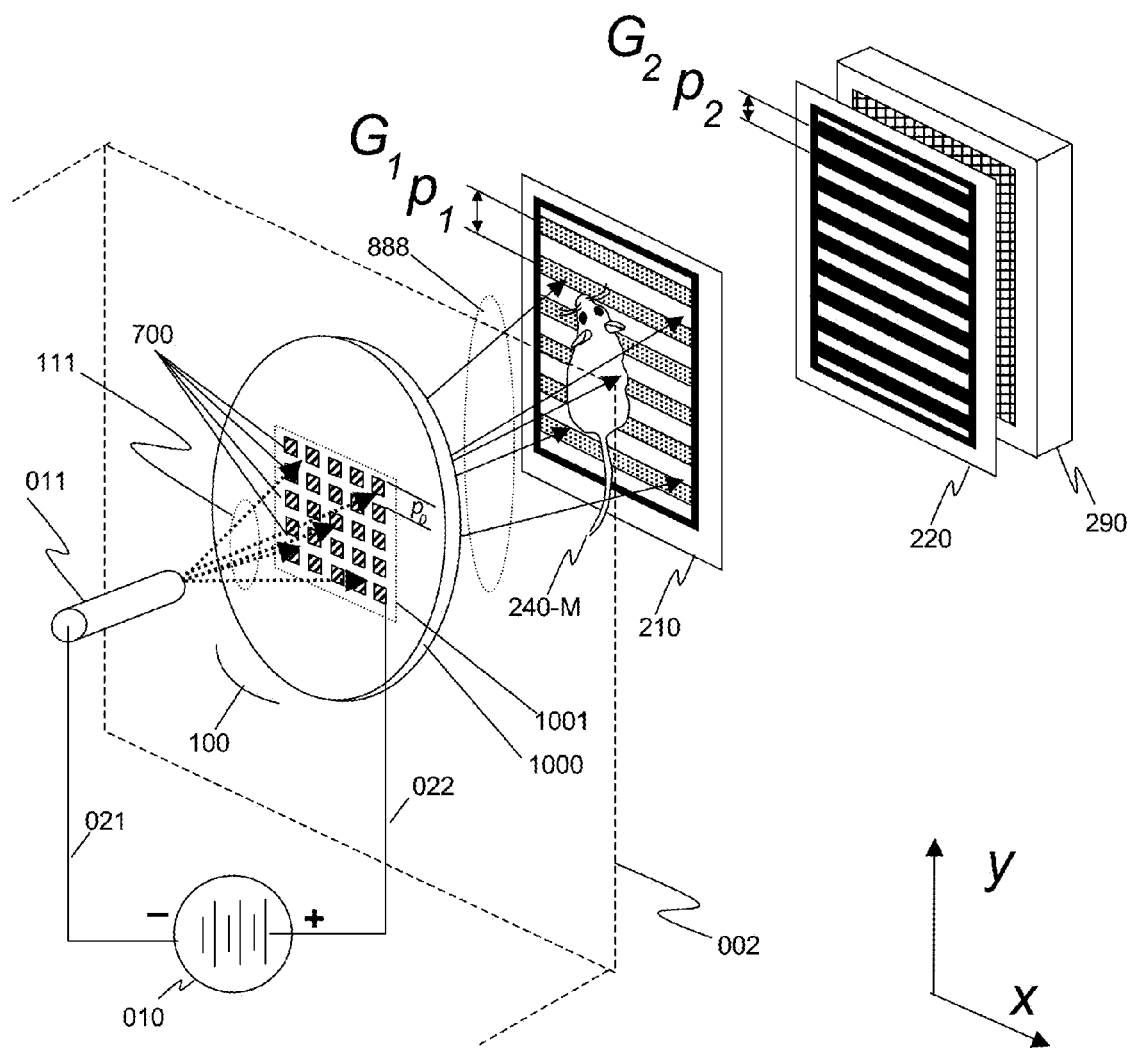
FIG. 11 illustrates a perspective view of the embodiment of the invention shown in FIG. 10, in which the x-ray target comprises a two-dimensional periodic array of x-ray generating microstructures.
Figure 12:
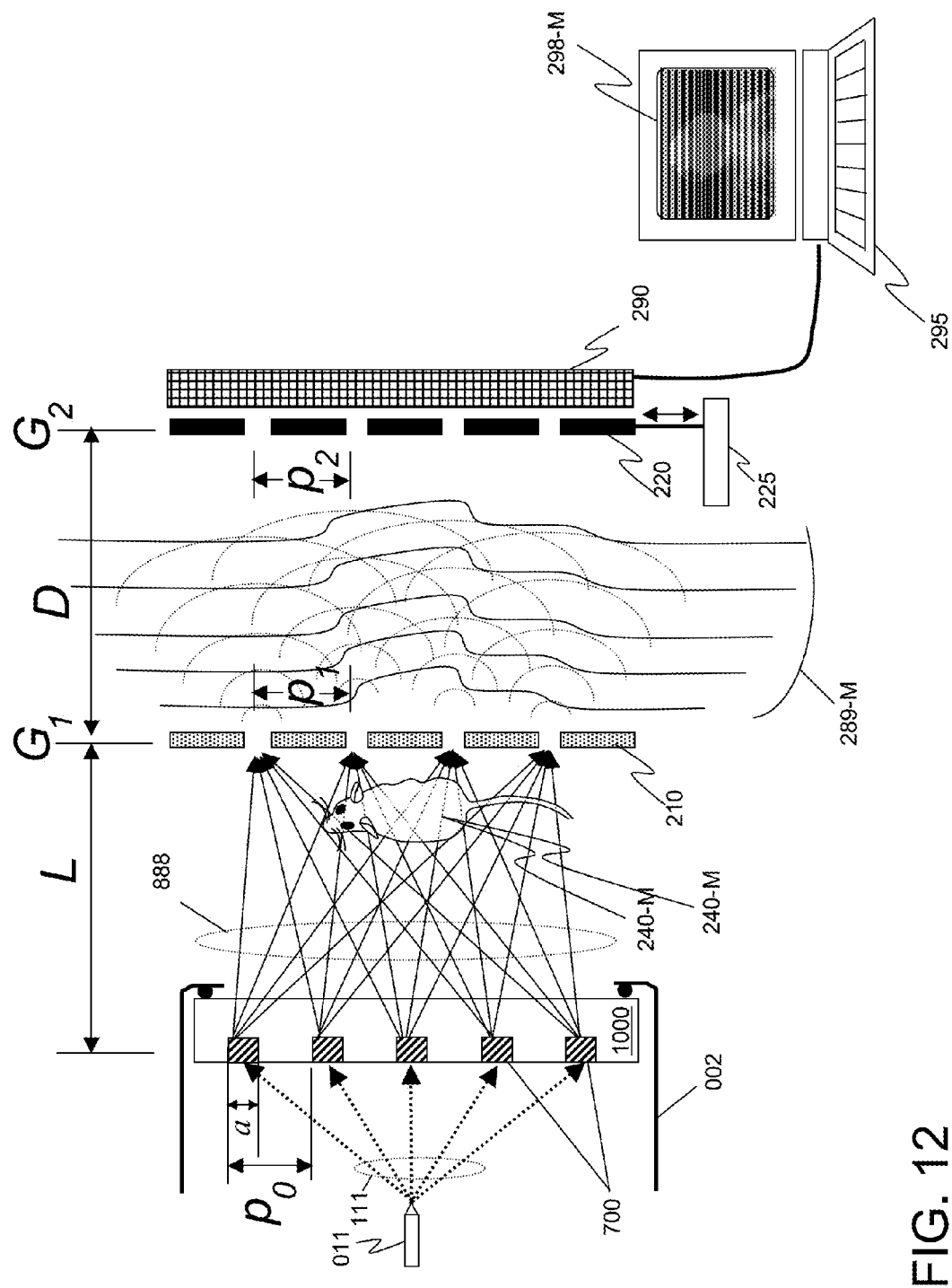
FIG. 12 illustrates a detailed schematic cross-section view of the embodiment of the invention shown in FIGS. 10 and 11.

FIGS. 10, 11 and 12 show a more detailed illustration of one embodiment of the invention, in which the array of sub-sources are formed using microstructures of x-ray generating material embedded in a thermally conducting substrate. In this embodiment, an x-ray source 008 illuminates an object 240-M and a beam-splitting grating $G_1$ 210, and the interference pattern they form is detected by a detector 290.

For the x-ray source 008, a high voltage power supply 010 provides electrons through a lead 021 to an electron emitter 011 in a vacuum chamber 002 held to a shielding housing 005 by supports 003. The electron emitter 011 emits electrons 111 towards a target 100. The target 100 comprises a substrate 1000 and a region that comprises a periodic array of discrete microstructures 700 comprising x-ray generating material (typically a high Z metallic material such as copper, molybdenum or tungsten) positioned on or embedded or buried in the substrate (typically a low Z material such as beryllium, diamond, silicon carbide). The discrete microstructures 700 may be any number of sizes or shapes, but are generally designed to be periodic arrays of right rectangular prisms with lateral dimensions on the order of microns in size in at least one dimension, such that the emission from each microstructure acts as a sub-source of x-rays with a spatial coherence length that is comparable to or larger than the grating period $p_1$ at the beam splitting grating $G_1$ 210. Additionally, the microstructures are preferably of a thickness (as typically measured orthogonal to the target surface) that is on the order of one half of the electron penetration depth within the substrate material.

The period $p_0$ of the microstructures 700 that form the x-ray sub-sources is related to the other geometric parameters in the system by:

$$p_0 = p_2 \frac{L}{D} \qquad \text{[Eqn. 4]}$$

where L is the distance from the x-ray sub-sources 700 to the grating $G_1$ 210, and D is the distance from the grating $G_1$ to the detector/analyzer grating $G_2$ 220 with period $p_2$. In some embodiments, D will be set to be one of the fractional Talbot distances with interference fringes of high contrast (visibility), defined by:

$$\text{Contrast} = \frac{I_{max} - I_{min}}{I_{max} + I_{min}} \qquad \text{[Eqn. 5]}$$

where $I_{max}$ and $I_{min}$ is the intensity peak and valley of the Talbot interference fringes without an object in the beam path, respectively.

For plane wave illumination (i.e. equivalent to the x-ray source being located at infinity) of a beam-splitting grating with a $\pi$ phase-shift, the distance D is preferably given by:

$$D = D_N = N \frac{p_1^2}{8\lambda} = \frac{N}{16} D_T \qquad \text{[Eqn. 6]}$$

where $D_N$ is the fractional Talbot distance for a plane wave illumination, $\lambda$ is the mean x-ray wavelength, and N is referred to as a Talbot fractional order. The preferred value of D is dependent on the attenuating or phase shifting properties of the beam-splitting grating $G_1$, the line-space ratio of the beam-splitting grating $G_1$, and the source-to-grating distance L. For a $\pi$ phase-shifting grating with a line-to-space ratio of 1:1, an odd integer fractional Talbot order N (N=1, 3, 5 . . . ) is preferred for determining the distance D. For an x-ray source located at a finite distance (e.g. L not infinity), D is increased to:

$$D = \frac{L \times D_N}{L - D_N} \qquad \text{[Eqn. 7]}$$

The Talbot fringe period $p_f$ for a given fractional order is given by:

$$p_f = Kp_1 \frac{L+D}{L} \quad [\text{Eqn. 8}]$$

where K is a parameter dependent on the attenuating or phase shifting properties of the beam-splitting grating $G_1$. K equals ½ when the beam-splitting grating is a π phase-shift grating, and equals 1 when the beam splitting grating is a π/2 phase shift grating.

Likewise, the Talbot fringe contrast is improved if a smaller x-ray sub-source size (i.e. more spatially coherent x-rays) is used, and in which the pitch $p_1$ used for the beam splitting grating $G_1$ is related to the size of the sub-source a and the distance L between them, satisfying the following requirement:

$$p_1 < \frac{\lambda L}{a} \quad [\text{Eqn. 9}]$$

where λ is a predetermined x-ray wavelength that will generally correspond to the wavelength of the monochromatic x-rays produced by the corresponding sub-source, or the mean x-ray wavelength for an x-ray sub-source with a broader spectrum.

In the vacuum chamber 002, electrons 111 bombard the target, and generate heat and x-rays 888 in the microstructures 700. The material in the substrate 1000 is selected such that it has relatively low energy deposition rate for electrons in comparison to the microstructures of the x-ray generating material, typically by selecting a low Z material for the substrate, and therefore will not generate a significant amount of heat and x-rays. The substrate 1000 material may also be chosen to have a high thermal conductivity, typically larger than 100 W/(m °C.). The microstructures of the x-ray generating material are also typically embedded within the substrate, i.e. if the microstructures are shaped as rectangular prisms, it is preferred that at least five of the six sides are in close thermal contact with the substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

The microstructures are typically connected electrically with a lead 022 to the positive terminal of the high voltage source 010 to allow the target to serve as an anode in the electrical system. Alternatively, the target may be grounded while the cathode (electron emitter) is of negative charge, or the target may be connected to a positive terminal while the cathode is grounded, so long as the anode is of relative higher voltage than the cathode. Additionally, in some embodiments, electron optics such as electrostatic lenses or magnetic coils may be placed inside or outside of the vacuum chamber 002 around or near the path of electrons 111 to further direct and focus the electron beam.

The target 100 as illustrated may additionally serve as a window in the vacuum chamber 002 so that the x-ray generating material is facing the interior of the vacuum chamber and the electron source, but x-rays 888 are also propagate through the back side of the target 100 towards the beam-splitting grating $G_1$ 210. In other embodiments, a separate window is used, and additional x-ray filters may also be used Once generated by the source 008, the x-rays 888 may pass through an optional shutter 230, an x-ray spectral filter to obtain a desired spectral bandwidth with a desired wavelength, and an object 240-M to be investigated. The x-rays then diffract off the beam splitting grating $G_1$ 210, which may additionally be mounted on a substrate 211, and then fall on the analyzer grating $G_2$ 220, which may also be mounted on a substrate 221. The final interference pattern will be detected by an array detector 290 that provides electrical signals corresponding to the x-ray intensity through a connector 291 to an image processing system 295 for analysis.

In addition to the x-ray source and interference detection system, means to move the object 240-M and the various gratings relative to each other, to the detector, and to the source may be used. In FIG. 10, the image processing system 295 may also be connected through a network 231 to a means 245 of controlling a stage 244 that sets the position and angle of the object 240-M, to a means 215 of controlling a mount 214 that sets the position and angle of the beam splitting grating $G_1$ 210, and to a means 225 of controlling a mount 224 that sets the position and angle of the analyzer grating $G_2$ 220, as well as a possible connection to the shutter 230 or to a switch 013 for the high voltage supply 010 to allow the x-rays to be moved and modulated (such as being turned on and off). Software run by processors in the image processing system 295 may control the motion of the gratings $G_1$ 210, $G_2$ 220, the object 240-M, and also the x-ray exposure to allow the collection of the multiple images needed to obtain detailed amplitude, differential phase, phase-contrast, and scattering contrast images of the object 240-M.

Additional embodiments may also include controls that allow the electron beam to be moved or modulated. For example, embodiments may be designed that additionally comprise a means of translating the x-ray source anode relative to the analyzer grating $G_2$. Additional embodiments that also allow the position and angle of the x-ray detector 290 to be adjusted may also be designed.

Figure 13:
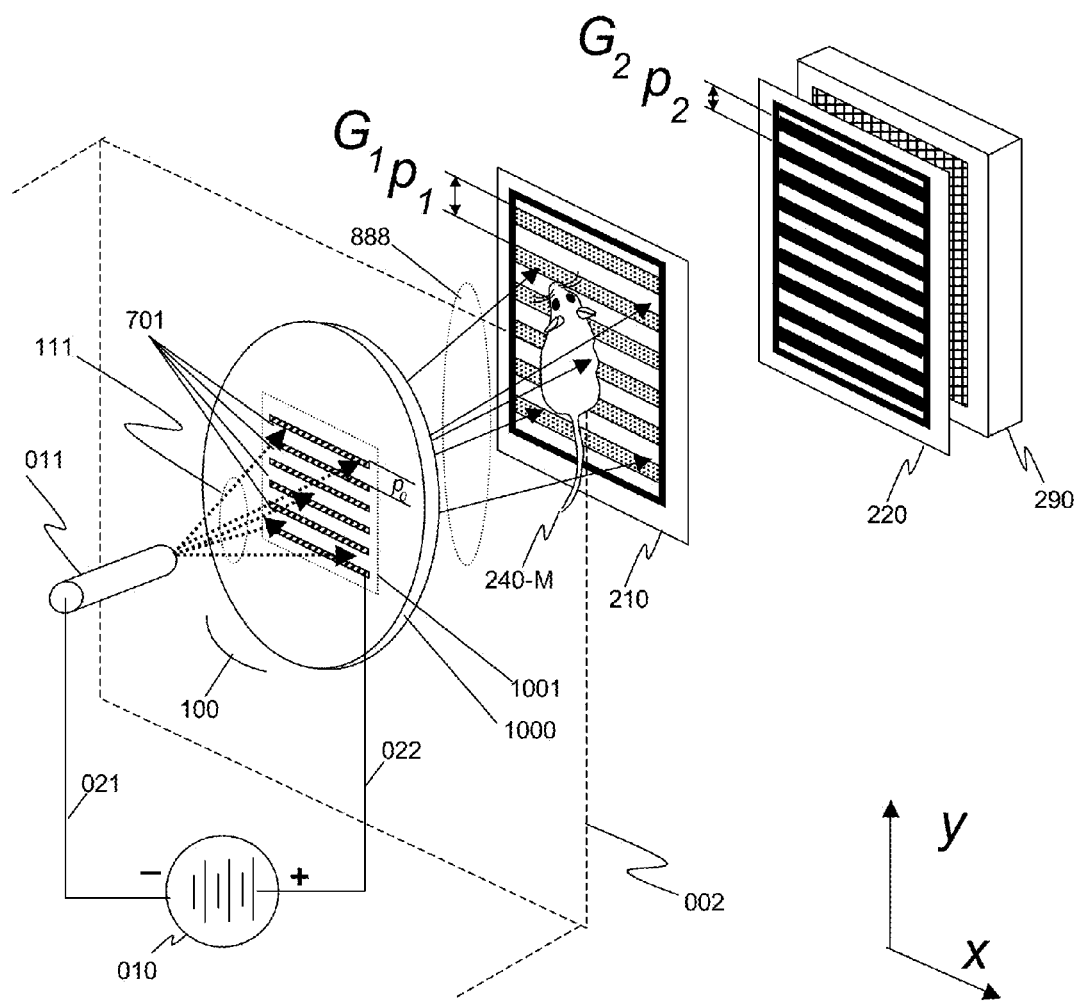
FIG. 13 illustrates a perspective view of an embodiment of the invention in which the x-ray target comprises of x-ray generating microstructures in the form of parallel lines.

FIG. 13 illustrates an embodiment of the invention in which the target 100 comprises a substrate 1000 and a plurality of microstructured line sources 701. These microstructured line sub-sources 701 will typically be a few microns wide in one direction (corresponding to the sub-source size parameter a, generally in the dimension orthogonal to the direction of the lines of the gratings $G_1$ 210 and $G_2$ 220, which corresponds to the y-direction in FIG. 13) but much longer (e.g. up to 1000 microns or several millimeters) in the direction parallel to the lines (which corresponds to the x-direction in FIG. 13). The pitch of the microstructures 701 as sub-sources as shown in FIG. 13 is $p_0$, and is related to the pitch of the analyzer/detector by Equation 4.

Figure 14:
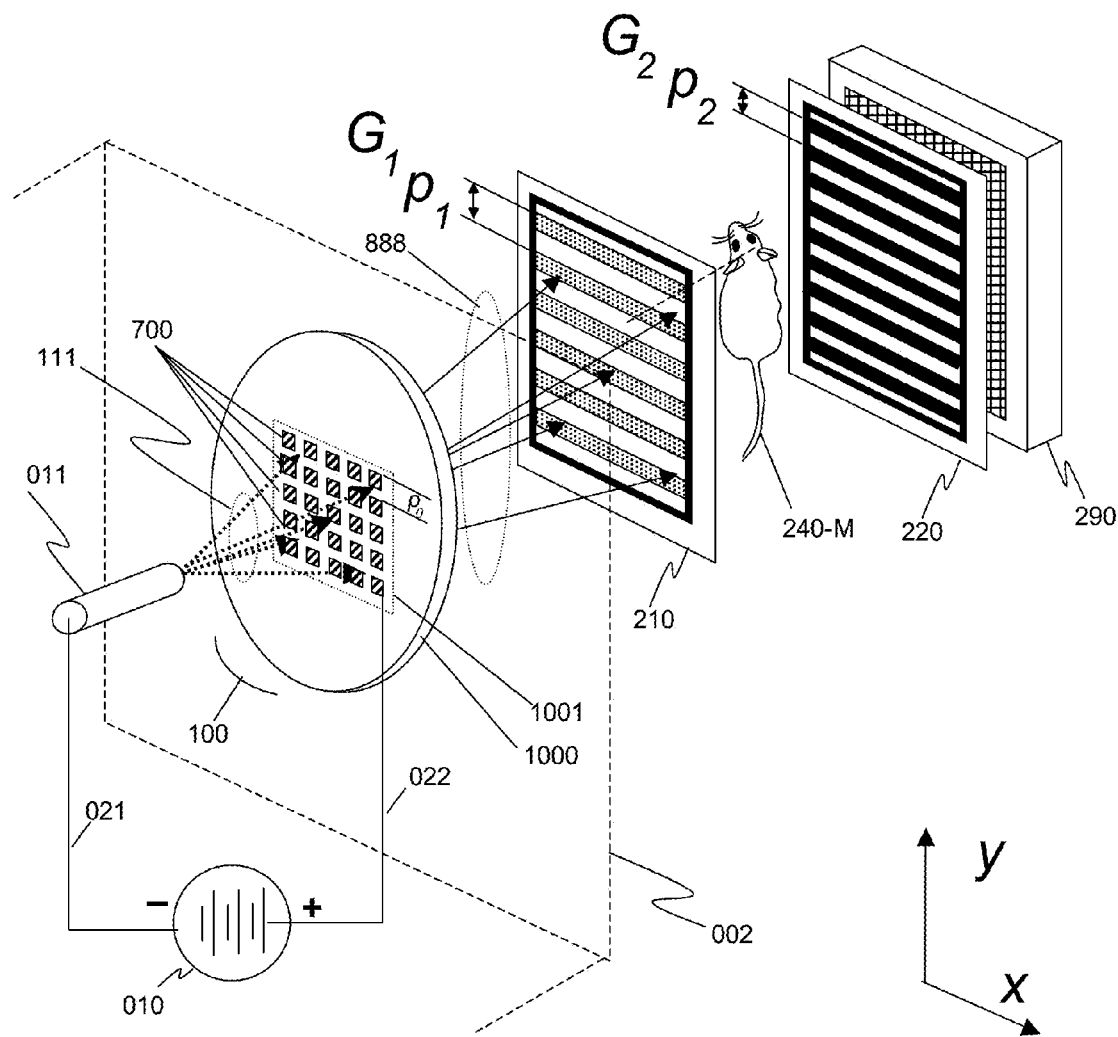
FIG. 14 illustrates a perspective view of an embodiment of the invention in which the object (a mouse) is placed between the gratings $G_1$ and $G_2$.

FIG. 14 illustrates an embodiment of the invention in which the object 240-M to be examined is placed between the gratings $G_1$ 210 and the detector 290. The microstructures 700 of x-ray generating material on the target as illustrated in FIG. 14 comprise sub-sources arranged in a 2-D periodic array in two orthogonal directions, but may be any periodic array that satisfies the coherence illumination condition of the beam-splitting grating $G_1$ 210, including a grid, a mesh, a checkerboard, or other periodic structures.

If the gratings comprise one-dimensional structures, the microstructures 700 in the source target 100 need only be periodic in the same direction as the 1-D arrays of $G_1$ 210 and G$_2$ 220 (i.e. the lines of microstructures 701 are ideally parallel to the lines of the gratings) but can have arbitrary or non-periodic structure in the perpendicular direction.

Figure 15:
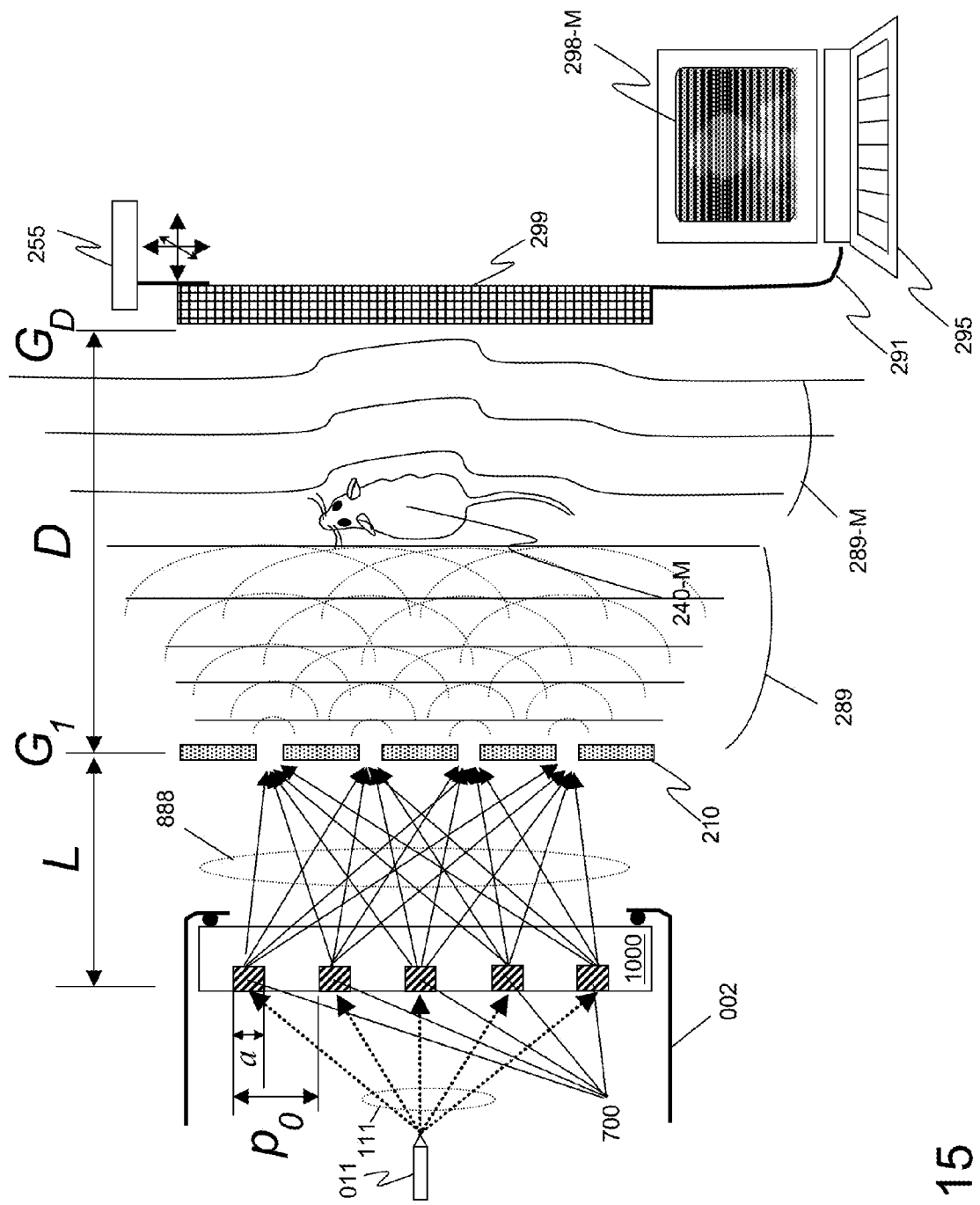
FIG. 15 illustrates a detailed schematic cross-section view of an embodiment of the invention in which a high-resolution detector is used without an analyzer grating.

FIG. 15 additionally illustrates an embodiment of the invention in which the there is no analyzer grating G$_2$ 220, but instead the detector 299 has a high resolution array G$_D$ with a pixel resolution equal to or better than one third (⅓) of the Talbot fringe period in the direction orthogonal to the grating lines. With this resolution, a single exposure image may be processed to obtain absorption, phase, and scattering contrast images simultaneously. This can be advantageous in that the intensity loss of 50% or more that typically occurs for x-rays passing through G$_2$ 220 is avoided, and the signal reaching the detector and therefore the signal-to-noise ratio is substantially higher.

In order to collect the multiple images for the calculation of detailed amplitude, differential phase, phase-contrast, and scattering contrast images for an object 240-M, the embodiment of FIG. 15 may additionally comprise a means 255 for translating the detector 290, not only in the two lateral directions parallel to the plane of the grating G$_1$, but also in direction defined along the path of x-ray propagation, to ensure that the detector 299 is placed at the correct multiple of the Talbot distance T$_D$.

Figure 16:
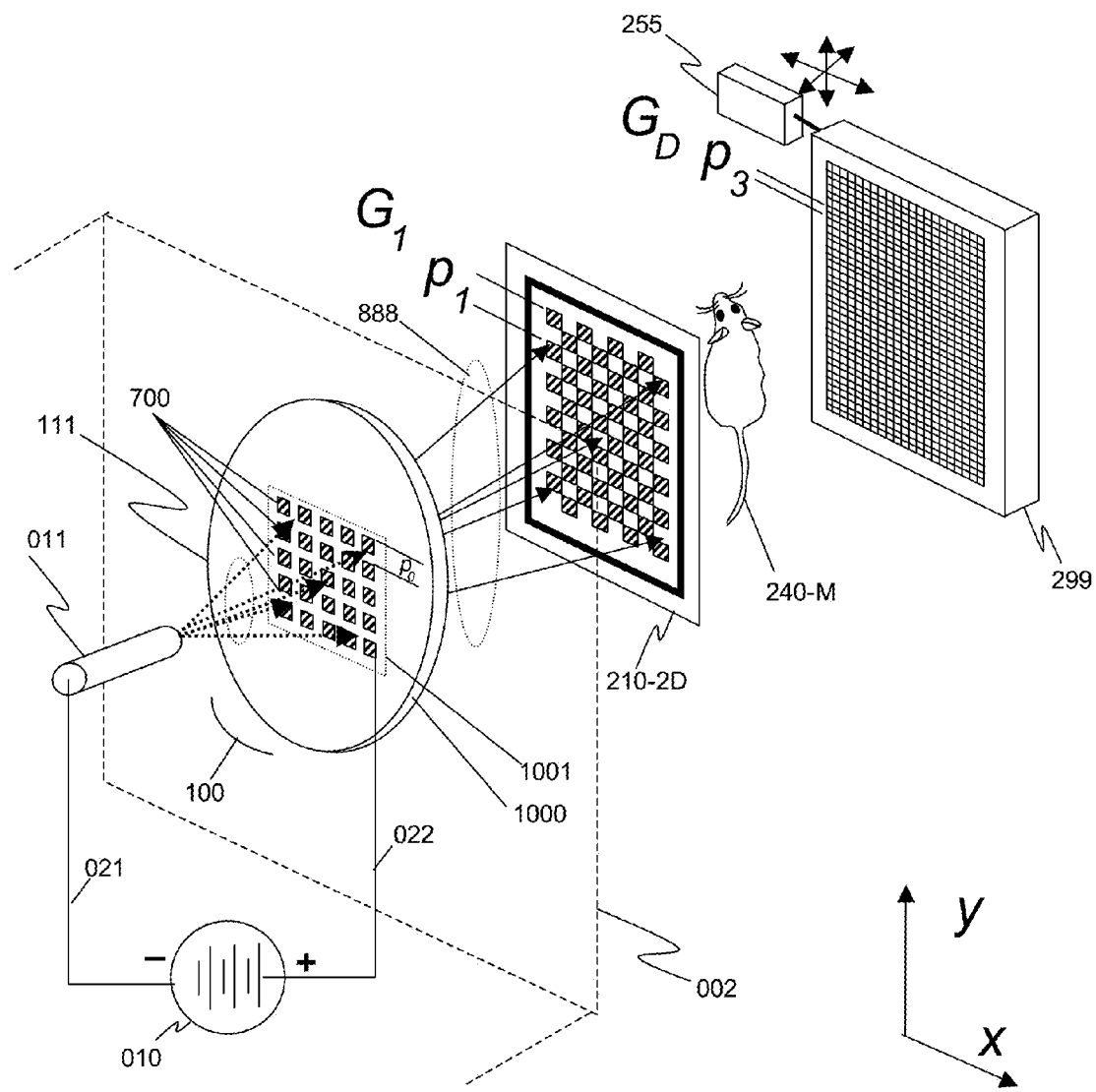
FIG. 16 illustrates a perspective view of an embodiment of the invention in which the object (a mouse) is placed between the grating $G_1$ and the detector, and the grating $G_1$ comprises a two-dimensional phase structure.
Figure 17:
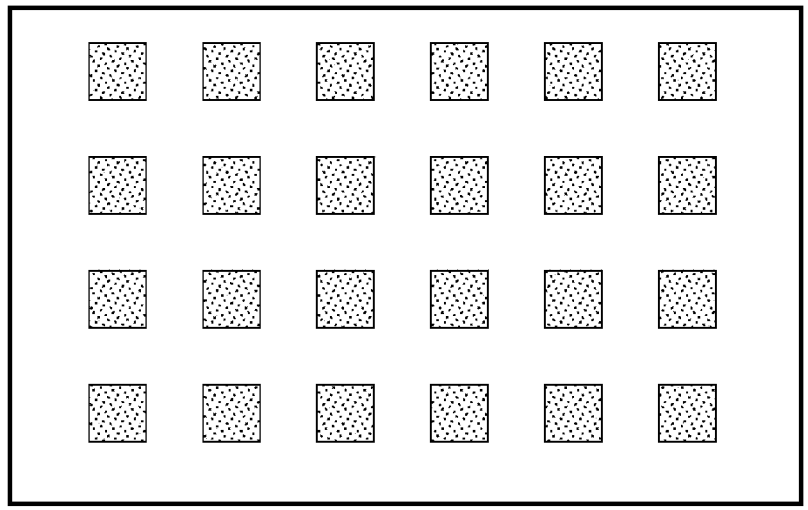
FIG. 17 illustrates a "mesh" 2-D pattern for a beam splitting grating used in some embodiments of the invention.
Figure 18:
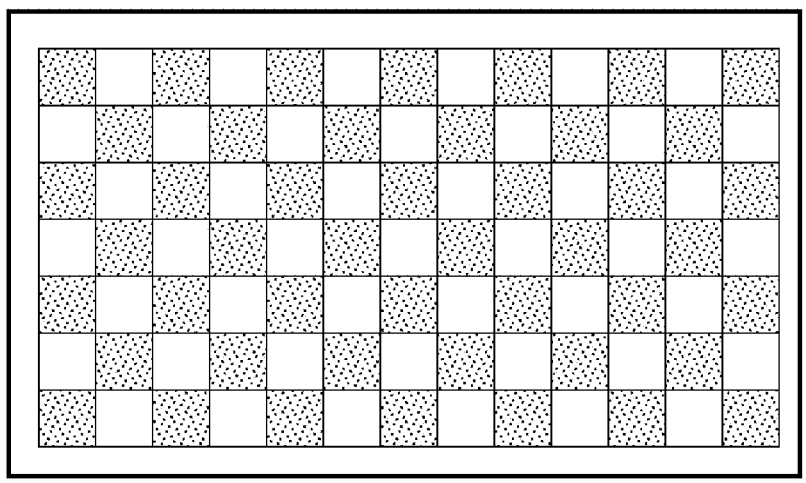
FIG. 18 illustrates a "checkerboard" 2-D pattern for a beam splitting grating used in some embodiments of the invention.

FIG. 16 illustrates an embodiment of the invention in which the beam splitting grating G$_1$ 210-2D comprises a two-dimensional periodic array, which may be either a transmission or a phase grating. When using a 2-D beam-splitting grating of this type, the patterns may be arranged in any one of a number of periodic patterns, including a mesh, such as the pattern illustrated in FIG. 17, or a checkerboard pattern, as illustrated in FIG. 18, In these illustrations, clear regions are non-phase shifted regions, while patterned regions represent regions with a relative phase shift. Different, or even opposite relative phase shifts, may also be used in some embodiments, i.e., the clear regions can be phased shifted while the patterned regions are not.

For use with an incident x-ray beam with a spectral bandwidth of less than ±15% around the mean energy, a beam splitting grating with a phase shift of π radians and a line-to-space ratio of 1:1 may be preferred. For use with an incident beam with a spectral bandwidth greater than ±15%, a relative phase shift of π/2 radians may be preferred.

The beam splitting gratings in some embodiments may have a profile comprising 1-D stripes, such as a Ronchi profile or structures having a rectangular profile. The relative phase shift between the dark and clear stripes is preferably selected to be π or π/2 radians, but may also be any integer multiple or fraction of π. Alternatively, the dark stripes may have low x-ray transmission so that the beam splitting grating is an absorption grating.

FIG. 16 illustrates the use of a 2-D beam splitting grating G$_1$ 210-2D in conjunction with a high-resolution detector 299, as was also shown in FIG. 15. To simultaneously obtain a differential phase contrast, phase contrast, absorption, scattering contrast images in two orthogonal directions, the geometric parameters, including the x-ray sub-source size a, the period p$_1$ of the grating G$_1$ 210-2D and the distance L, need to satisfy the coherence illumination condition of the grating G$_1$ in both directions. As before, the detector 299 has spatial resolution equal to or better than ⅓ of the Talbot fringe period in the two orthogonal directions in the image plane and is positioned to be aligned with the Talbot fringe pattern.

Such embodiments with 2-D patterns on the beam splitting grating G$_1$ 210-2D may also be used with the previously described lower resolution detector 290 in conjunction with a two-dimensional analyzer grating G$_2$ which may be phase stepped in two directions in any sequence so that the phase information is obtained in both orthogonal directions. Similar to the description of G$_1$ 210-2D above, this 2-D analyzer grating G$_2$ may be of any periodic structure such as a mesh, a checkerboard, or 2-D array of structures such as circles, triangles, squares, rectangles, etc.

Figure 19:
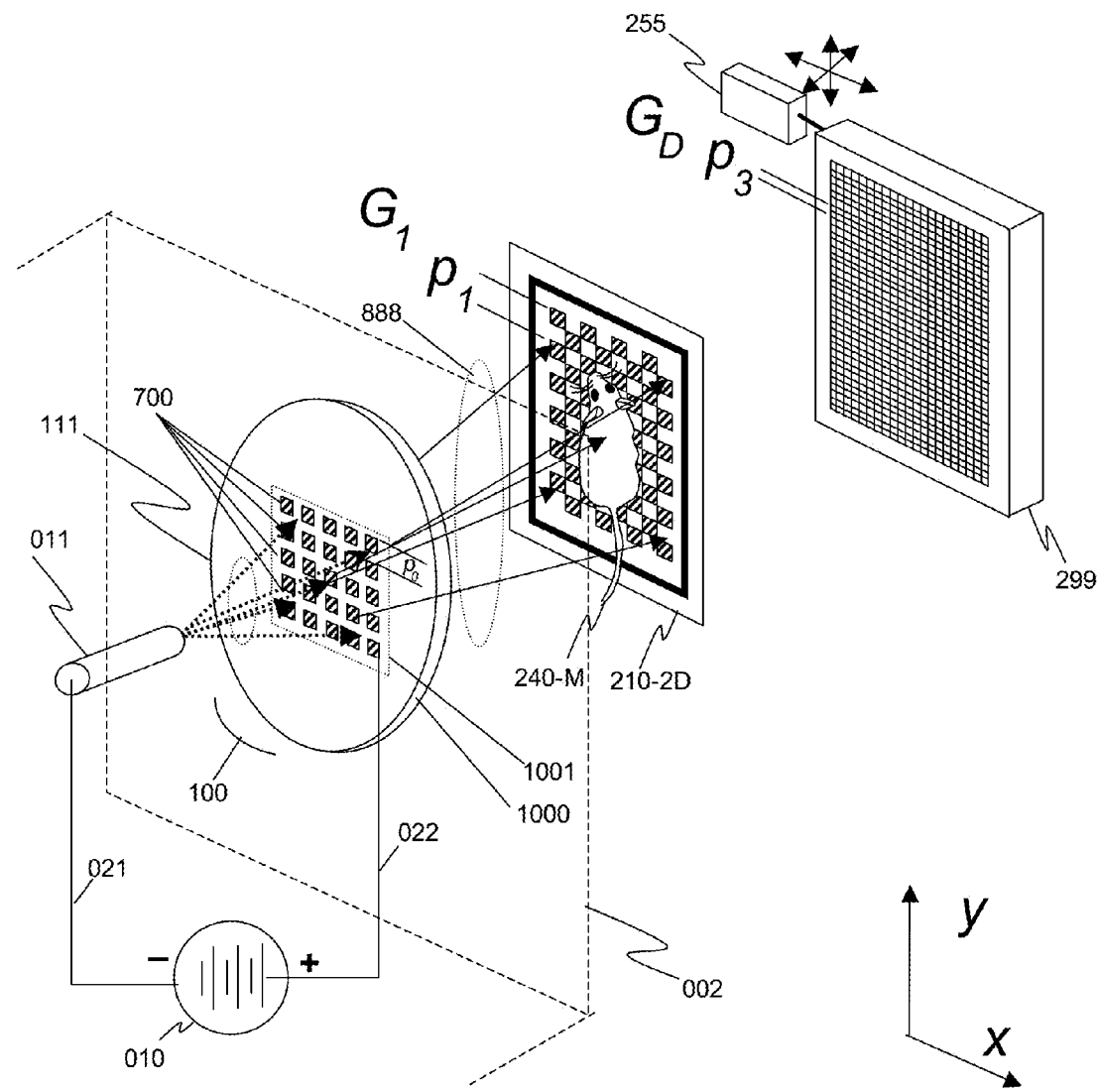
FIG. 19 illustrates a perspective view of an embodiment of the invention in which the object (a mouse) is placed between the source and the grating $G_1$, and the grating $G_1$ comprises a two-dimensional phase structure.

FIG. 19 represents an embodiment similar to FIG. 16, except that the object 240-M under examination is now placed between the x-ray source and the beam-splitting grating 210-2D.

Note that some of the embodiments are one-dimensional Talbot-Yun interferometers in which absorption, phase, and scattering information is obtained in one direction and incorporate one or more 1-D gratings in combination with a micro structured source target that is periodic in at least in the direction perpendicular to the grating line direction (but may be periodic in other directions as well). Other embodiments are two-dimensional Talbot-ST interferometers in which absorption, phase, and scattering information is obtained in two orthogonal directions (or all three dimensions by performing computed tomography using the 2-D Talbot-Yun setup).

Figure 20:
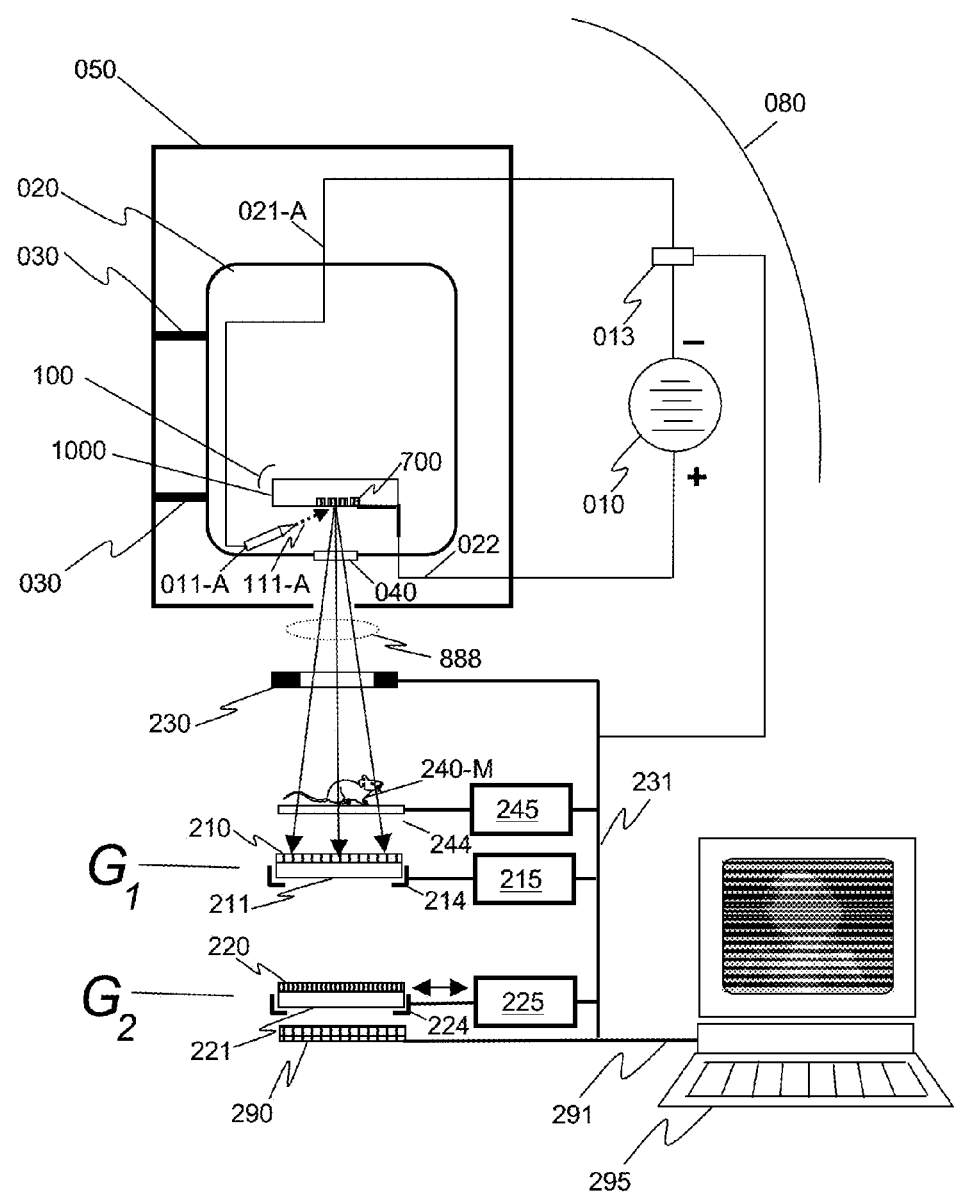
FIG. 20 illustrates a schematic cross-section view of an embodiment of the invention in which the target is mounted within the vacuum chamber.
Figure 21:
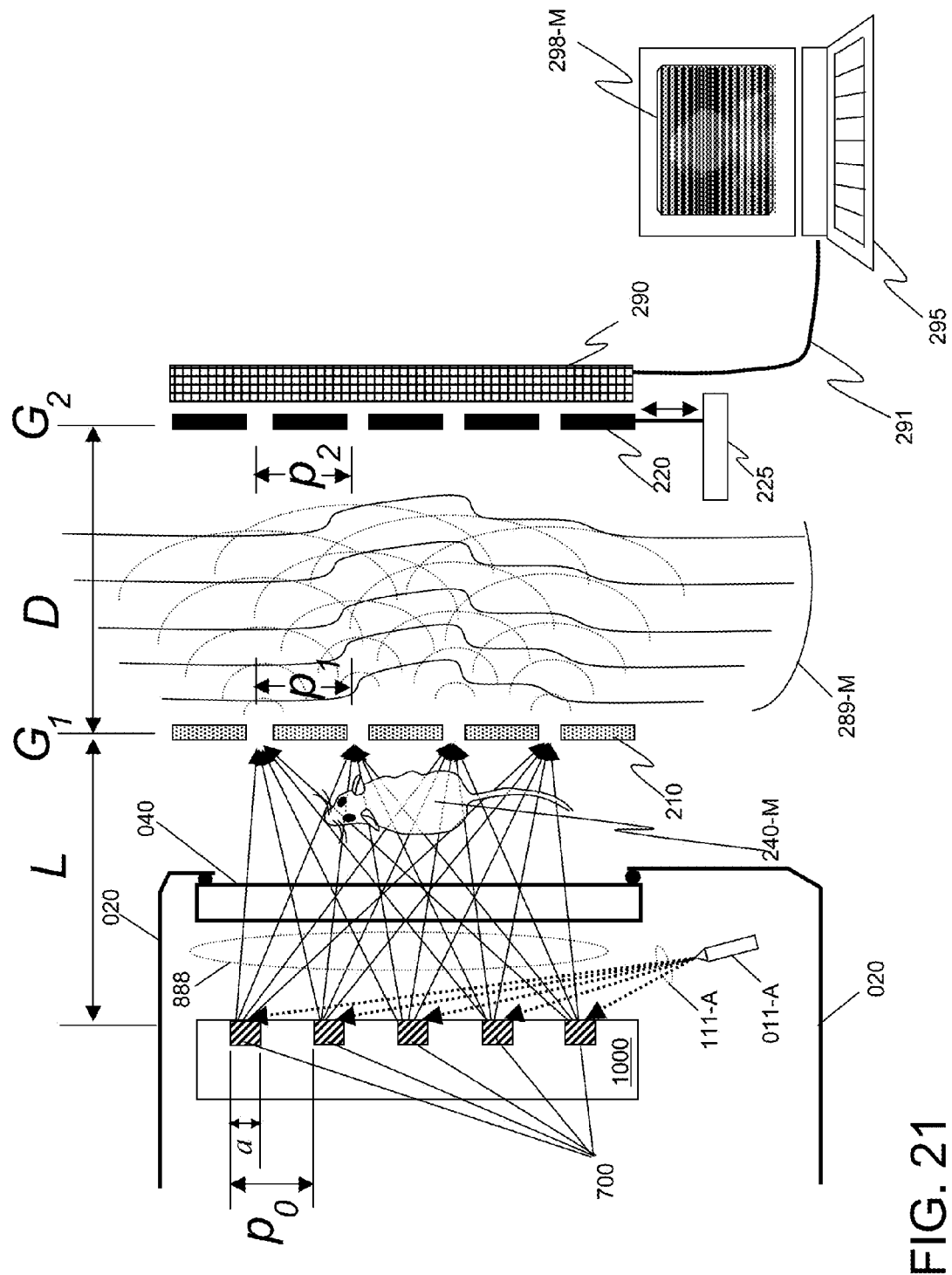
FIG. 21 illustrates a detailed schematic cross-section view of the embodiment of the invention shown in FIG. 20.

FIGS. 20 and 21 illustrate another embodiment of the invention in which the x-ray source 080 comprises a vacuum chamber 020 supported on mounts 030 within an x-ray shielding housing 050. The source 080 also comprises a target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-A to an electron emitter 011-A, while the positive terminal is connected through one or more leads 022 to the microstructures in the target, allowing them to serve as an anode.

However, in this embodiment, the surface of the target 100 comprising the periodic array of x-ray sub-sources 700 comprising of x-ray generating material is facing a window 040 mounted in the wall of the vacuum chamber 020, and the electron emitter 011-A is aligned to emit a beam of electrons 111-A onto the surface of the target 100 comprising sub-sources 700 facing the window 040.

Figure 22:
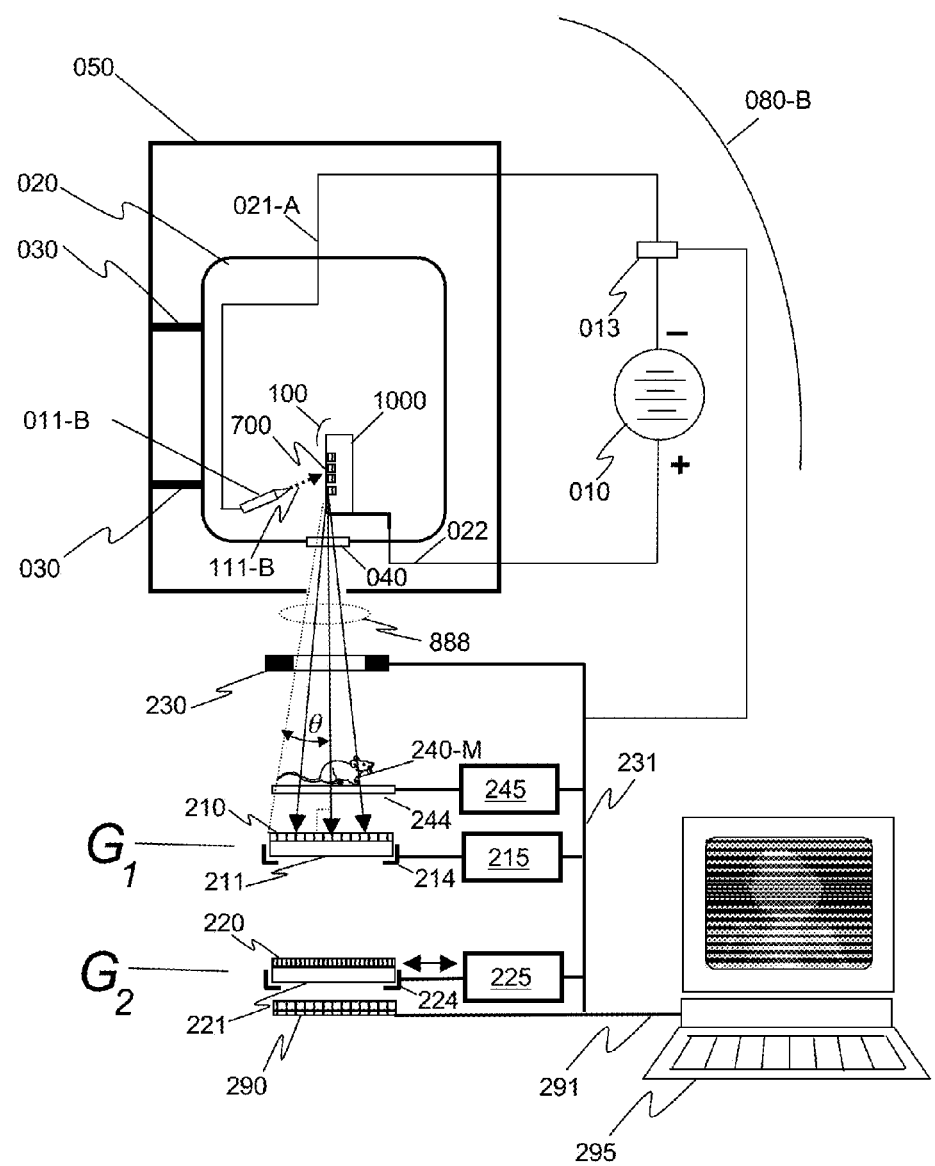
FIG. 22 illustrates a schematic cross-section view of an embodiment of the invention in which the target is mounted within the vacuum chamber and x-rays are generated using linear accumulation.
Figure 23:
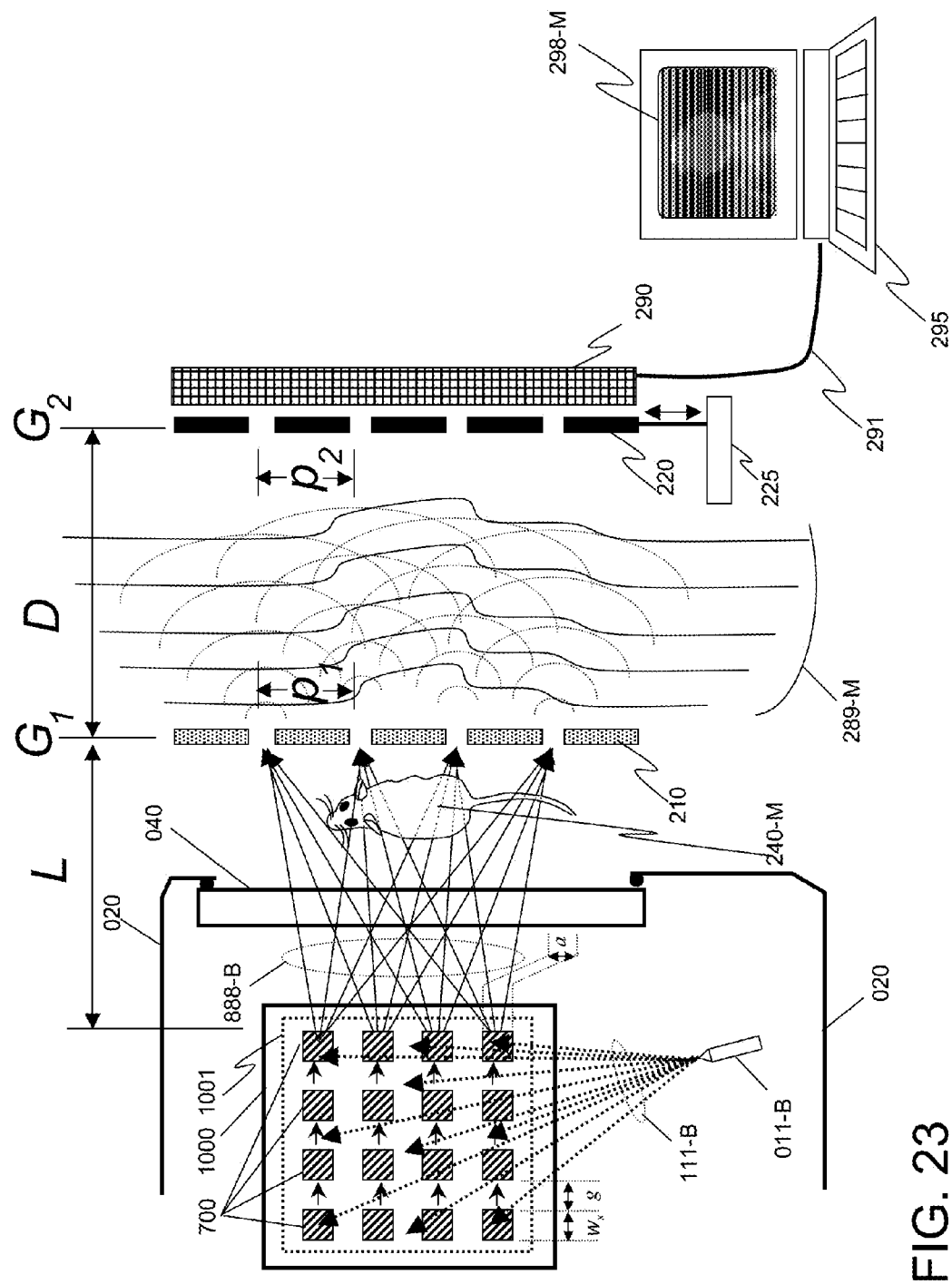
FIG. 23 illustrates a detailed schematic cross-section view of the embodiment of the invention shown in FIG. 22.

FIGS. 22 and 23 illustrate another embodiment of the invention in which the target 100 comprising a substrate 1000 and a periodic pattern comprising x-ray sub-sources 700 mounted entirely within the vacuum chamber 020. As before, this embodiment also comprises a high voltage source 010, which has a negative terminal connected through a lead 021-B to an electron emitter 011-B, while the positive terminal is connected through one or more leads 022 to the microstructures in the target, allowing them to serve as an anode.

However, in this embodiment, the surface of the target 100 comprising the periodic array of x-ray sub-sources 700 comprising x-ray generating material is oriented such that x-rays produced by some of the microstructures propagate towards other microstructures that are also producing x-rays, and a linear accumulation of x-rays 888-B from a plurality of microstructures 700 emerges from the target. The distance g between the microstructures and microstructures 700 emerges from the target. The distance g between the microstructures and the width w$_x$ in the propagation direction should be small enough such that the emission from the nth microstructure contributing to the accumulated x-rays can be considered as a single sub-source with dimension a of Eqn. 9, i.e.:

$$a \geq \tan\theta \cdot (n(g+w_x))$$ [Eqn. 10]

where a is the sub-source dimension that meets the coherence requirements of the system, and θ is one half of the field-of-view angle for the system.

Linear accumulation of x-ray sources as used in this embodiment of the invention is described more fully in the co-pending U.S. Patent Application entitled X-RAY SOURCES USING LINEAR ACCUMULATION by the inventors of the present invention (U.S. patent application Ser. No. 14/490,672 filed Sep. 19, 2014), which is hereby incorporated by reference in its entirety. Any of the source designs and configurations disclosed in the above referenced co-pending application may be considered for use as a component in any or all of the interferometric imaging systems disclosed herein.

Figure 24:
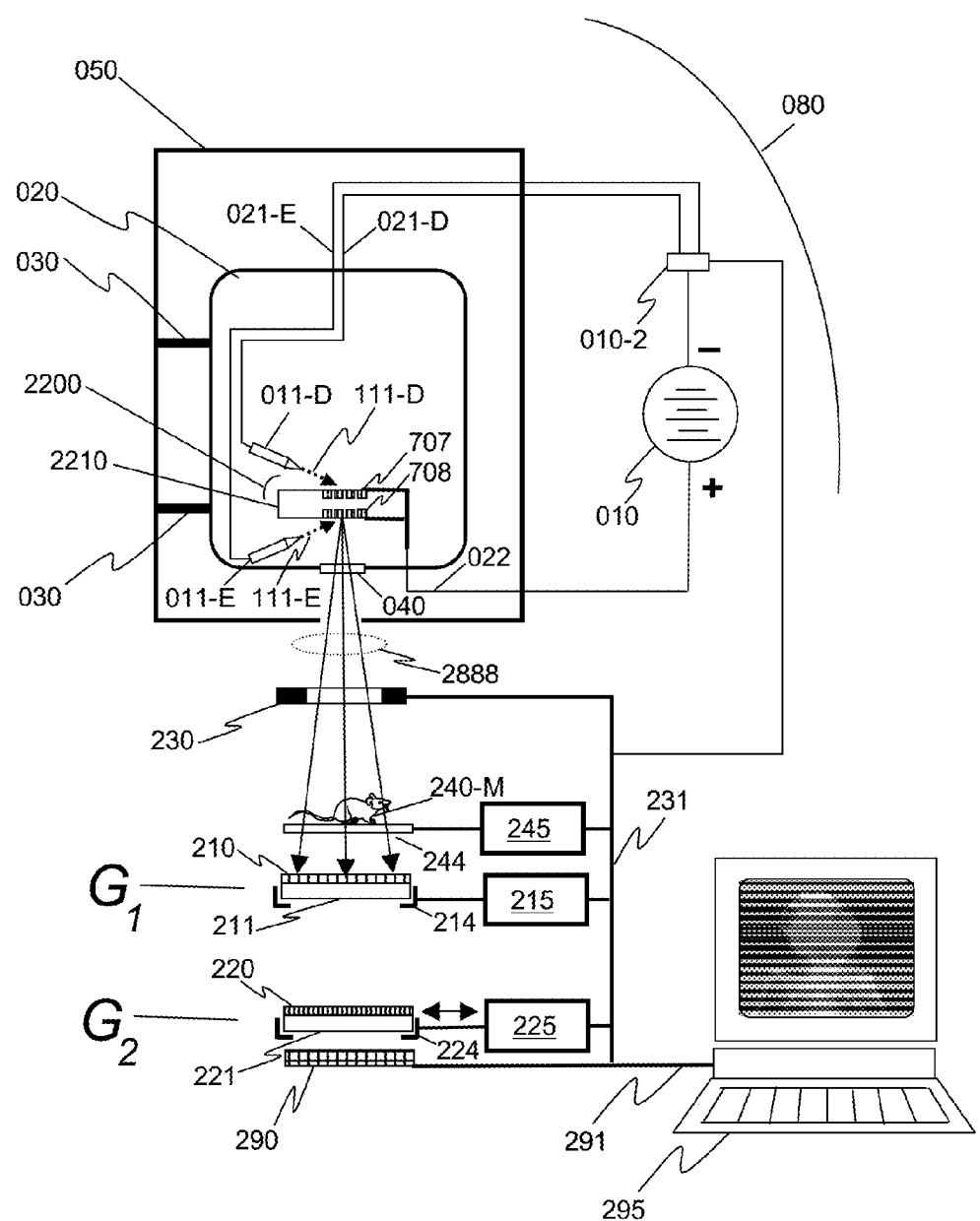
FIG. 24 illustrates a schematic cross-section view of an embodiment of the invention in which two electron beams bombard the target from both sides.
Figure 25:
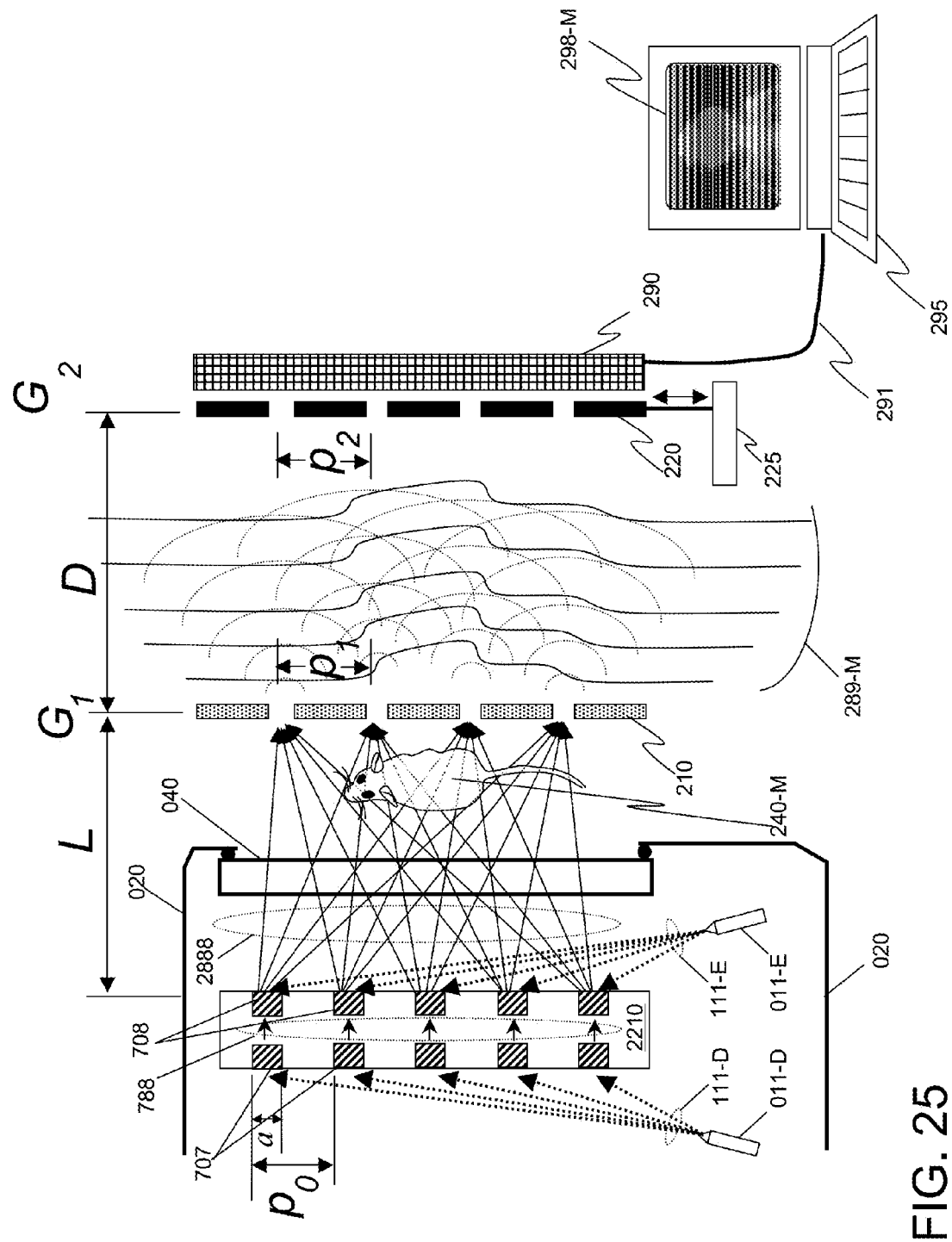
FIG. 25 illustrates a detailed schematic cross-section view of the embodiment of the invention shown in FIG. 24.

Likewise, FIGS. 24 and 25 illustrate another embodiment of the invention that utilizes linear accumulation of x-rays. In this embodiment, the x-ray source 080 includes a target 2200 comprising a substrate 2210 and a first set of sub-sources 707 and a second set of sub-sources 708 mounted entirely within the vacuum chamber 020. As before, this embodiment also comprises a high voltage source 010, but this high voltage source is connected to a junction 010-2 that provides high voltage to two electron emitters 011-D and 011-E through leads 021-D and 021-E, respectively. As shown in FIGS. 24 and 25, the first electron emitter 021-D provides an electron beam 111-D that bombards the first set of sub-sources 707, while the second electron emitter 021-E provides an electron beam 111-E that bombards the second set of sub-sources 708. Some of the x-rays 788 generated by the first set of sub-sources 707 and the second set of sub-sources 708 along the x-ray imaging beam axis combine to produce x-rays 2888 from the target 2200 will be augmented by the linear accumulation of x-rays from these two sets of x-ray sub-sources. In some embodiments, the separation between the two sets of sub-sources 707 and 708 may be smaller than 5 mm but larger than the source size in direction perpendicular to a line passing through the center of the two sub-sources. The periods of both the sub-sources 707 and 708 may be selected so that the associated Talbot fringes downstream of the beam splitting grating $G_1$ substantially overlap.

It will also be known to those skilled in the art that other embodiments of the invention comprising an x-ray source in which the target/anode under bombardment by electrons is moved, translated, or rotated to distribute the heat load are also possible.

Note: The illustrations of FIGS. 10 through 25 are not shown to scale, and are meant to illustrate the principle of the invention and not specific relationships between the microstructures 700, the target 100 and the various grating periods $p_1$ and $p_2$. The microstructures 700, 701, 707, 708 etc. may be on the order of microns in size, while the object under examination 240-M may be centimeters in size. Likewise, although these are illustrated in which an object with dimensions on the order of centimeters (a mouse) is shown, the techniques described are not limited to such objects, but may be used to examine even larger structures, or microscopic structures as well, as long as a suitable resolution for the detector and other elements of the interferometer are suitably constructed.

2. Fabrication of X-Ray Targets

Targets such as those to be used in x-ray sources according to the invention disclosed herein have been described in detail in the co-pending U.S. Patent Application entitled STRUCTURED TARGETS FOR X-RAY GENERATION by the inventors of the present invention (U.S. patent application Ser. No. 14/465,816, filed Aug. 21, 2014), which is hereby incorporated by reference in its entirety. Any of the target designs and configurations disclosed in the above referenced co-pending application may be considered for use as a component in any or all of the x-ray sources disclosed herein.

As described herein and in the above cited pending Patent Applications, the target used in the source of x-rays may comprise a periodic array of sub-sources. Each sub-source may be comprised of a single or multiple microstructures of x-ray generating material in thermal contact with, or preferably embedded in, a substrate selected for its thermal conductivity. When the microstructures are in good thermal contact with a substrate having a high thermal conductivity, higher electron current densities may be used to generate x-rays, since the excess heat will be drawn away into the substrate. The higher current densities will give rise to higher x-ray flux, leading to a higher brightness source. As described in the above co-pending patent Applications, sources with microstructures of x-ray generating material may have a brightness more than 10 times larger than simpler constructions made from the same materials. Additional configurations in which multiple sub-sources are aligned to contribute x-rays on the same axis can multiply the brightness further through linear accumulation of the x-ray sub-sources.

It should also be noted here that, when the word "microstructure" is used herein, it is specifically referring to microstructures comprising x-ray generating material. Other structures, such as the cavities used to form the x-ray microstructures, have dimensions of the same order of magnitude, and might also be considered "microstructures". As used herein, however, other words, such as "structures", "cavities", "holes", "apertures", etc. may be used for these structures when they are formed in materials, such as the substrate, that are not selected for their x-ray generating properties. The word "microstructure" will be reserved for structures comprising materials selected for their x-ray generating properties.

Likewise, it should be noted that, although the word "microstructure" is used, x-ray generating structures with dimensions smaller than 1 micron, or even as small as nano-scale dimensions (i.e. greater than 10 nm) may also be described by the word "microstructures" as used herein as long as the properties are consistent with the geometric factors for sub-source size and grating pitches set forth in the various embodiments.

It should also be noted that, when the word "sub-source" is used, it may refer to a single microstructure of x-ray generating material, or an ensemble of smaller microstructures that function similarly to a single structure for the purposes of Talbot interferometry.

The fabrication of these microstructured targets may follow well known processing steps used for the creation of embedded structures in substrates. If the substrate is a material with high thermal conductivity such as diamond, conventional lithographic patterning, such as focused ion beam lithography or electron beam lithography, using photoresists can produce micron sized structures, which may then be etched into the substrate using processes such as reactive ion etching (RIE). Deposition of the x-ray generating material into the etched structures formed in the substrate may then be carried out using standard deposition processes, such as electroplating, chemical vapor deposition (CVD), atomic layer deposition, or hot pressing.

The x-ray generating material used in the target should ideally have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For these reasons, targets are often fabricated using tungsten, with an atomic number Z=74.

Table I lists several materials that are commonly used for x-ray targets, several additional potential target materials (notably useful for specific characteristic lines of interest), and some materials that may be used as substrates for target materials. Melting points, and thermal and electrical conductivities are presented for values near 300° K (27° C.). Most values are cited from the *CRC Handbook of Chemistry and Physics*, 90$^{th}$ ed. [CRC Press, Boca Raton, Fla., 2009]. Other values are cited from various sources found on the Internet. Note that, for some materials (such as sapphire, for example), thermal conductivities an order of magnitude larger may be possible when cooled to temperatures below that of liquid nitrogen (77° K) [see, for example, Section 2.1.5, Thermal Properties, of E. R. Dobrovinskaya et al., *Sapphire: Material, Manufacturing, Applications*, Springer Science+Business Media, L L C, 2009].

Figure 26:
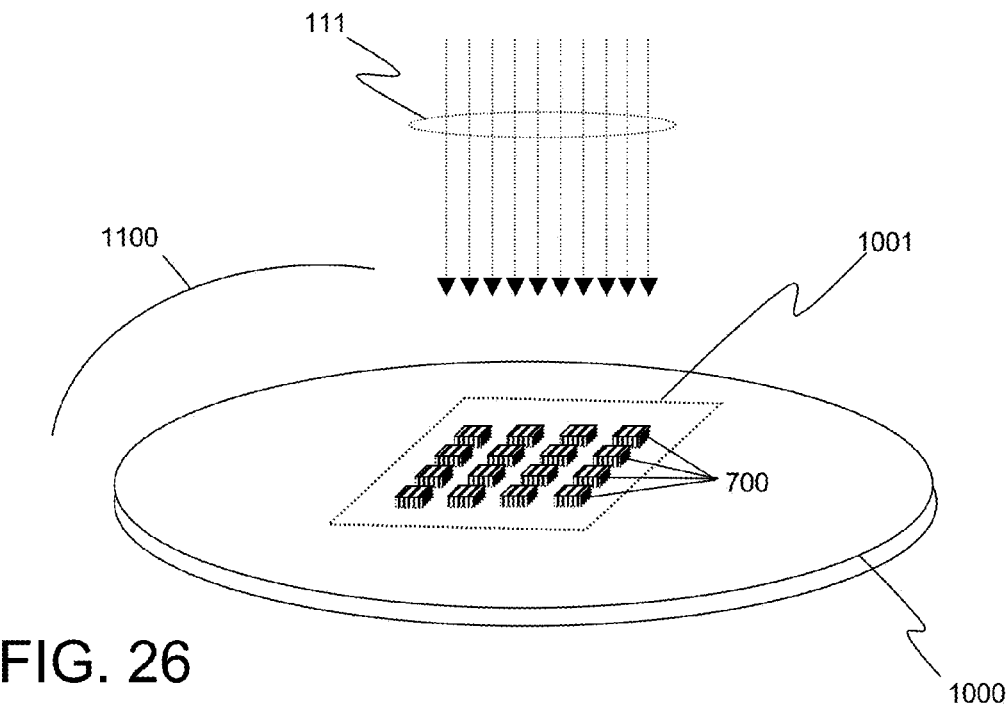
FIG. 26 illustrates a perspective view of a target comprising a grid of embedded rectangular target microstructures on a larger substrate that may be used in some embodiments of the invention.

FIG. 26 illustrates a target as may be used in some embodiments of the invention. In this figure, a substrate 1000 has a region 1001 that comprises an array of sub-sources 700 comprising microstructures of x-ray generating material (typically a metallic material), in which the sub-sources are arranged in a regular array of right rectangular prisms. In a vacuum, electrons 111 bombard the target from above, and generate heat and x-rays in the microstructures 700. The material in the substrate 1000 is selected such that it has relatively low x-ray production (efficiency is proportional to atomic number) and energy deposition rate (stopping power is proportional to density) for electrons in comparison to the x-ray generating microstructure material, and therefore will not generate a significant amount of heat and x-rays. This is typically achieved by selecting a low mass density and low atomic number (Z) material for the substrate.

The substrate 1000 material may also be chosen to have a high thermal conductivity, typically larger than 100 W/(m ° C.), and the microstructures are typically embedded within the substrate, i.e. if the microstructures are shaped as rectangular prisms, it is preferred that at least five of the six sides are in close thermal contact with the

TABLE I

Various Target and Substrate Materials and Selected Properties.

| Material (Elemental Symbol) | Atomic Number Z | Melting Point ° C. (1 atm) | Thermal Conductivity (W/(m ° C.)) | Electrical Conductivity (MS/m) |
|---|---|---|---|---|
| Common Target Materials: | | | | |
| Chromium (Cr) | 24 | 1907 | 93.7 | 7.9 |
| Iron (Fe) | 26 | 1538 | 80.2 | 10.0 |
| Cobalt (Co) | 27 | 1495 | 100 | 17.9 |
| Copper (Cu) | 29 | 1085 | 401 | 58.0 |
| Molybdenum (Mo) | 42 | 2623 | 138 | 18.1 |
| Silver (Ag) | 47 | 962 | 429 | 61.4 |
| Tungsten (W) | 74 | 3422 | 174 | 18.4 |
| Other Possible Target Materials: | | | | |
| Titanium (Ti) | 22 | 1668 | 21.9 | 2.6 |
| Gallium (Ga) | 35 | 30 | 40.6 | 7.4 |
| Rhodium (Rh) | 45 | 1964 | 150 | 23.3 |
| Indium (In) | 49 | 157 | 81.6 | 12.5 |
| Cesium (Cs) | 55 | 28 | 35.9 | 4.8 |
| Rhenium (Re) | 75 | 3185 | 47.9 | 5.8 |
| Gold (Au) | 79 | 1064 | 317 | 44.0 |
| Lead (Pb) | 82 | 327 | 35.3 | 4.7 |
| Other Potential Substrate Materials with low atomic number: | | | | |
| Beryllium (Be) | 4 | 1287 | 200 | 26.6 |
| Carbon (C): Diamond | 6 | * | 2300 | $10^{-19}$ |
| Carbon (C): Graphite∥ | 6 | * | 1950 | 0.25 |
| Carbon (C): Nanotube (SWNT) | 6 | * | 3180 | 100.00 |
| Carbon (C): Nanotube (bulk) | 6 | * | 200 | |
| Boron Nitride (BN) | B = 5 N = 7 | ** | 20 | $10^{-17}$ |
| Silicon (Si) | 14 | 1414 | 124 | $1.56 \times 10^{-9}$ |
| Silicon Carbide (β-SiC) | Si = 14 C = 6 | 2798 | 0.49 | $10^{-9}$ |
| Sapphire (Al$_2$O$_3$)∥C | Al = 13 O = 8 | 2053 | 32.5 | $10^{-20}$ |

* Carbon does not melt at 1 atm; it sublimes at ~3600° C.
** BN does not melt at 1 atm; it sublimes at ~2973° C.

substrate 1000, so that heat generated in the microstructures 700 is effectively conducted away into the substrate 1000. However, targets used in other embodiments may have fewer direct contact surfaces. In general, when the term "embedded" is used in this disclosure, at least half of the surface area of the microstructure will be in close thermal contact with the substrate.

Note that the sub-source sizes and dimensions in some embodiments may be constrained by the same limitations as the periodicity $p_0$ of the grating $G_0$ in prior art. In other words, the spatial resolution achievable at the object position in the x-ray interferometric imaging systems as shown in FIGS. 9 through 25 is determined by the overall x-ray source size and the detector resolution, similar to the conditions described in the prior art interferometric imaging systems, such as the Talbot-Lau system. Therefore, the maximum x-ray source size (width of each microstructure spot) is limited for a given detector resolution and a given imaging geometry as determined by the distance between the source and object and the distance between the object to the detector.

The line-to-space ratio of the arrays of sub-sources is a design parameter that should be considered in the design of any system. A large spatial coherence length is inversely proportional to the size of an x-ray source or sub-source. Because the fringe visibility of the Talbot interference fringes increases linearly with the relative ratio of the spatial coherence length of the illuminating x-ray beam to the period of the beam-splitting grating $p_1$ for a value of the ratio from 0.3 to 1, it is generally preferred to have a small source size. However, the x-ray production is inversely proportional to the area of the sub-source (e.g. a reduction in line width will lead to a decrease of x-ray production). Since the throughput of an imaging system is generally proportional to square of the contrast transfer function and only proportional to the x-ray flux, it is generally preferred to have a line-to-space ration less than 1:1. Some embodiments of the invention may use a line-to-space (i.e. x-ray generating material to substrate material) ratio between 1:5 and 1:2 (i.e. the relative area of the x-ray generating material may range from 20% to 33%).

A figure of merit (FOM) that may be helpful for the selection of materials for targets according to this invention is the ratio of x-rays produced by the microstructures to the x-rays produced by the electrons also bombarding the substrate. This figure of merit may be useful for the design of and selection of materials for the targets for the system, and should be taken into consideration in addition to the thermal conductivity of the substrate. As the electron energy deposition rate is proportional to the mass density and the x-ray production efficiency in a material is proportional to its atomic number, this figure of merit may be defined as follows:

$$FOM = \frac{Z_2 \times \rho_2}{Z_1 \times \rho_1} \quad [\text{Eqn. 11}]$$

where Z is the atomic number and ρ is the density, and material 1 is the substrate and material 2 is the x-ray generating material.

cially useful when used with electron beams focused to form a micro-spot, or by more intricate systems that form a more complex electron exposure pattern.

The depth of penetration of electrons into the material can be estimated by Pott's Law [P. J. Potts, Electron Probe Microanalysis, Ch. 10 of *A Handbook of Silicate Rock Analysis*, Springer Netherlands, 1987, p. 336)], which states that the penetration depth x in microns is related to the 10% of the value of the electron energy $E_0$ in keV raised to the 3/2 power, divided by the density of the material:

$$x(\mu m) = 0.1 \times \frac{E_0^{1.5}}{\rho} \quad [\text{Eqn. 12}]$$

For less dense material, such as a diamond substrate, the penetration depth is much larger than for a material with greater density, such as most materials containing elements used for x-ray generation.

Using this formula, Table III illustrates some of the estimated penetration depths for some common x-ray target materials.

TABLE II

Figure of Merit for x-ray material/substrate combinations.

| Substrate material | | | Microstructure material | | | Figure of Merit |
|---|---|---|---|---|---|---|
| Material | Atomic # $Z_1$ | Mass density (g/cm³) | Material | Atomic # $Z_2$ | Mass density (g/cm³) | $\frac{Z_2 \times \rho_2}{Z_1 \times \rho_1}$ |
| SiC | 12.55 | 3.21 | Cu | 29 | 8.96 | 6 |
| Si | 14 | 2.33 | Cu | 29 | 8.96 | 8 |
| SiC | 12.55 | 3.21 | Mo | 42 | 10.2 | 11 |
| Diamond | 6 | 3.5 | Cu | 29 | 8.96 | 12 |
| Si | 14 | 2.33 | Mo | 42 | 10.2 | 13 |
| Diamond | 6 | 3.5 | Mo | 42 | 10.2 | 21 |
| SiC | 12.55 | 3.21 | W | 74 | 19.25 | 35 |
| Be | 4 | 1.85 | Cu | 29 | 8.96 | 35 |
| Si | 14 | 2.33 | W | 74 | 19.25 | 44 |
| Be | 4 | 1.85 | Mo | 42 | 10.2 | 59 |
| Diamond | 6 | 3.5 | W | 74 | 19.25 | 68 |
| Be | 4 | 1.85 | W | 74 | 19.25 | 193 |

A number of microstructures and substrate material combinations are listed below in Table II. Any of the following combinations may be used, but it is preferable that the materials are selected such that the FOM is greater than 12, and that the thermal conductivity of the substrate material is greater than 100 W/(m ° C.) at room temperature.

Figure 27:
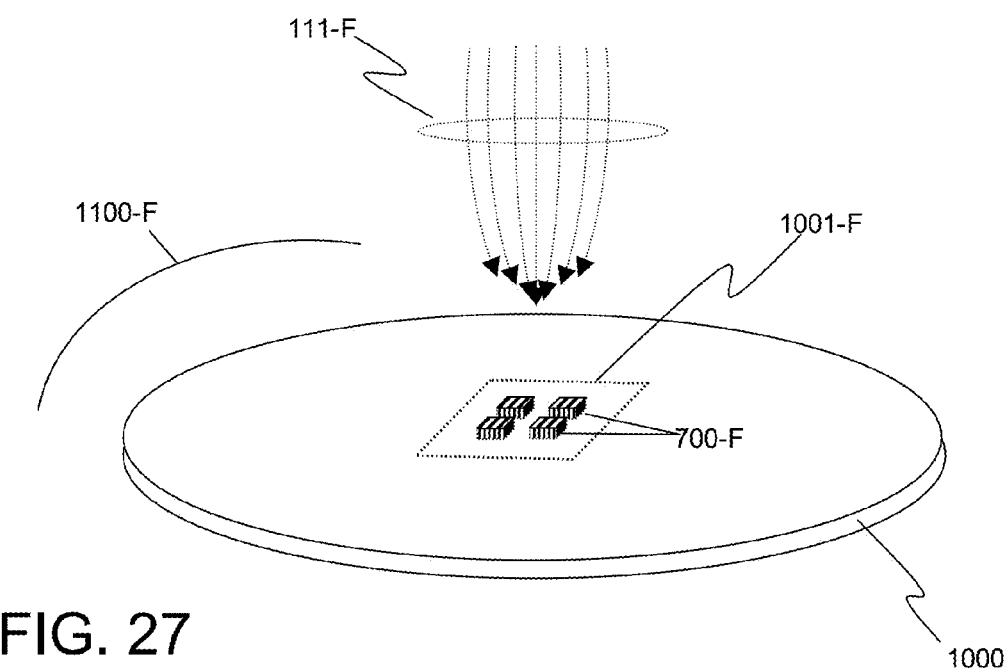
FIG. 27 illustrates a perspective view of a variation of a target comprising a grid of embedded rectangular target microstructures on a larger substrate for use with focused electron beam that may be used in some embodiments of the invention.

FIG. 27 illustrates another target as may be used in some embodiments of the invention in which the electron beam 111-F is directed by electrostatic lenses to form a more concentrated, focused spot. For this situation, the target 1100-F will still comprise a region 1001-F comprising an array of microstructures 700-F comprising x-ray material, but the size and dimensions of this region 1001-F can be matched to regions where electron exposure will occur. In these targets, the "tuning" of the source geometry and the x-ray generating material can be controlled such that the designs mostly limit the amount of heat generated to the micro structured region 1001-F, while also reducing the design and manufacturing complexity. This may be espe-

TABLE III

Estimates of penetration depth for 60 keV electrons into some materials.

| Material | Z | Density (g/cm³) | Penetration Depth (μm) |
|---|---|---|---|
| Diamond | 6 | 3.5 | 13.28 |
| Copper | 29 | 8.96 | 5.19 |
| Molybdenum | 42 | 10.28 | 4.52 |
| Tungsten | 74 | 19.25 | 2.41 |

The majority of characteristic Cu K x-rays are generated within the penetration depth. The electron interactions below that depth typically generate few characteristic K-line x-rays but will contribute to the heat generation, thus resulting in a low thermal gradient along the depth direction. It is therefore preferable in some embodiments to set a maximum thickness for the microstructures in the target in order to limit electron interaction in the material and optimize local thermal gradients. One embodiment of the invention limits the depth of the micro structured x-ray generating material in the target to between one third and two thirds of the electron penetration depth in the substrate at the incident electron energy. In this case, the lower mass density of the substrate leads to a lower energy deposition rate in the substrate material immediately below the x-ray generating material, which in turn leads to a lower temperature in the substrate material below. This results in a higher thermal gradient between the x-ray generating material and the substrate, enhancing heat transfer. The thermal gradient is further enhanced by the high thermal conductivity of the substrate material.

For similar reasons, selecting the thickness of the microstructures to be less than one half of the electron penetration depth in the substrate is also generally preferred for efficient generation of bremsstrahlung radiation, because the electrons below that depth have lower energy and thus lower x-ray production efficiency.

Note: Other choices for the dimensions of the x-ray generating material may also be used. In targets as used in some embodiments of the invention, the depth of the x-ray material may be selected to be 50% of the electron penetration depth in the substrate. In other embodiments, the depth of the x-ray material may be selected to be 33% of the electron penetration depth in the substrate. In other embodiments, the depth for the microstructures may be selected related to the "continuous slowing down approximation" (CSDA) range for electrons in the material. Other depths may be specified depending on the x-ray spectrum desired and the properties of the selected x-ray material.

Figure 28A:
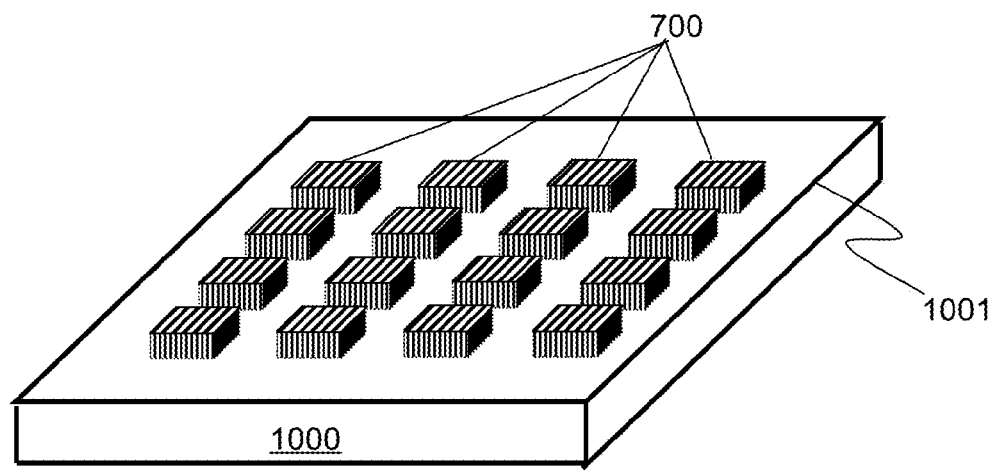
FIG. 28A illustrates a perspective view of a target comprising a grid of embedded rectangular target microstructures as used in some embodiments of the invention.
Figure 28B:
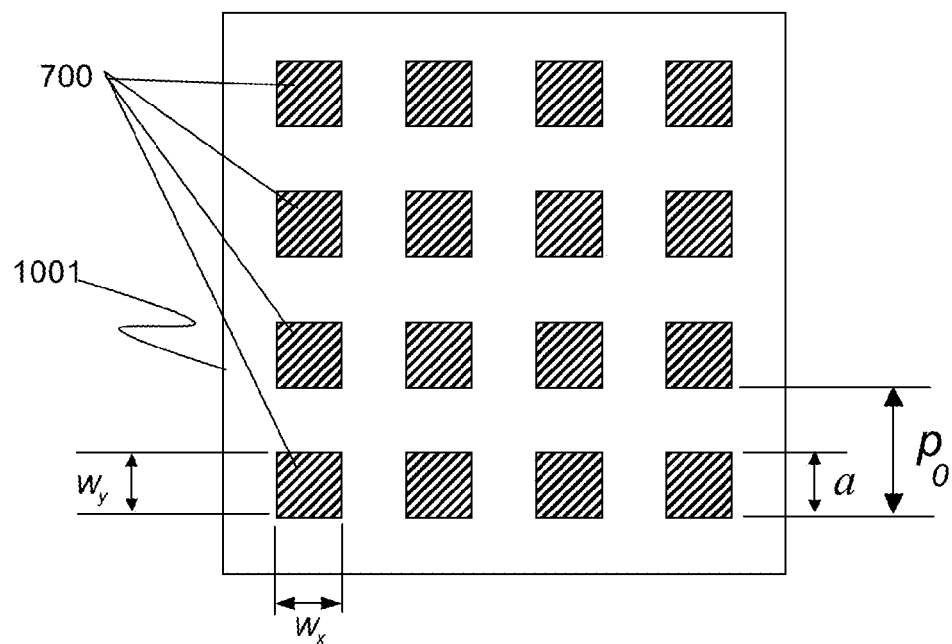
FIG. 28B illustrates a top view of the target of FIG. 28A.
Figure 28C:
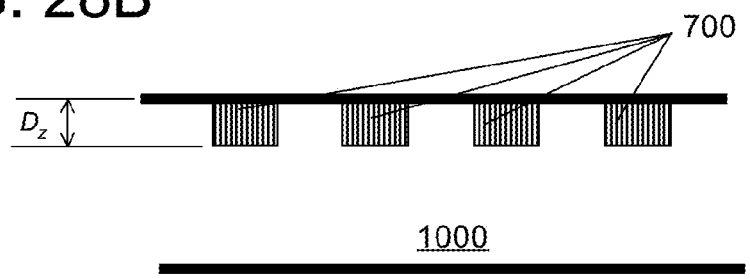
FIG. 28C illustrates a side/cross-section view of the target of FIGS. 28A and 28B.

FIG. 28 illustrates a region 1001 of a target as may be used in some embodiments of the invention that comprises an array of sub-sources 700 with microstructures in the form of right rectangular prisms comprising x-ray generating material arranged in a regular array. FIG. 28A presents a perspective view of the sixteen microstructures 700 for this target, while FIG. 28B illustrates a top down view of the same region, and FIG. 28C presents a side/cross-section view of the same region. (For the term "side/cross-section view" in this disclosure, the view meant is one as if a cross-section of the object had been made, and then viewed from the side towards the cross-sectioned surface. This shows both detail at the point of the cross-section as well as material deeper inside that might be seen from the side, assuming the substrate itself were transparent [which, in the case of diamond, is generally true for visible light].)

In these targets, the microstructures have been fabricated such that they are in close thermal contact on five of six sides with the substrate. As illustrated, the top of the microstructures 700 are flush with the surface of the substrate, but other targets in which the microstructure is recessed may be fabricated, and still other targets in which the microstructures present a topographical "bump" relative to the surface of the substrate may also be fabricated.

An alternative target as may be used in some embodiments of the invention may have several microstructures of right rectangular prisms simply deposited upon the surface of the substrate. In this case, only the bottom base of the prism would be in thermal contact with the substrate. For a structure comprising the microstructures embedded in the substrate with a side/cross-section view as shown in FIG. 28C with depth $D_z$ and lateral dimensions in the plane of the substrate of $W_x$ and $W_y$, the ratio of the total surface area in contact with the substrate for the embedded microstructures vs. deposited microstructures is $$\frac{A_{Embedded}}{A_{Deposited}} = 1 + 2D\frac{(W+L)}{(W \times L)} \quad \text{[Eqn. 13]}$$

With a small value for D relative to W and L, the ratio is essentially 1. For larger thicknesses, the ratio becomes larger, and for a cube (D=W=L) in which 5 equal sides are in thermal contact, the ratio is 5. If a cap layer of a material with similar properties as the substrate in terms of mass density and thermal conductivity is used, the ratio may be increased to 6.

Figure 29A:
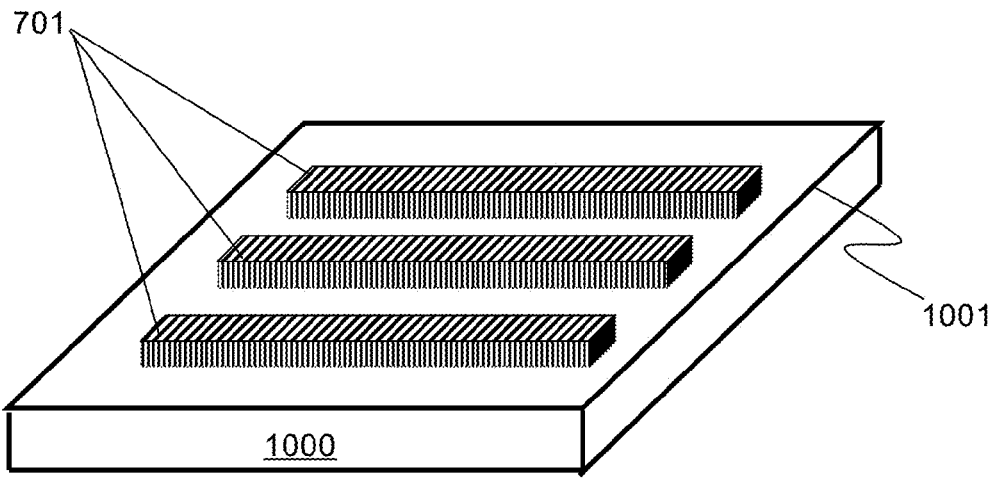
FIG. 29A illustrates a perspective view of a target comprising a set of embedded rectangular target microstructures forming a periodic linear pattern as used in some embodiments of the invention.
Figure 29B:
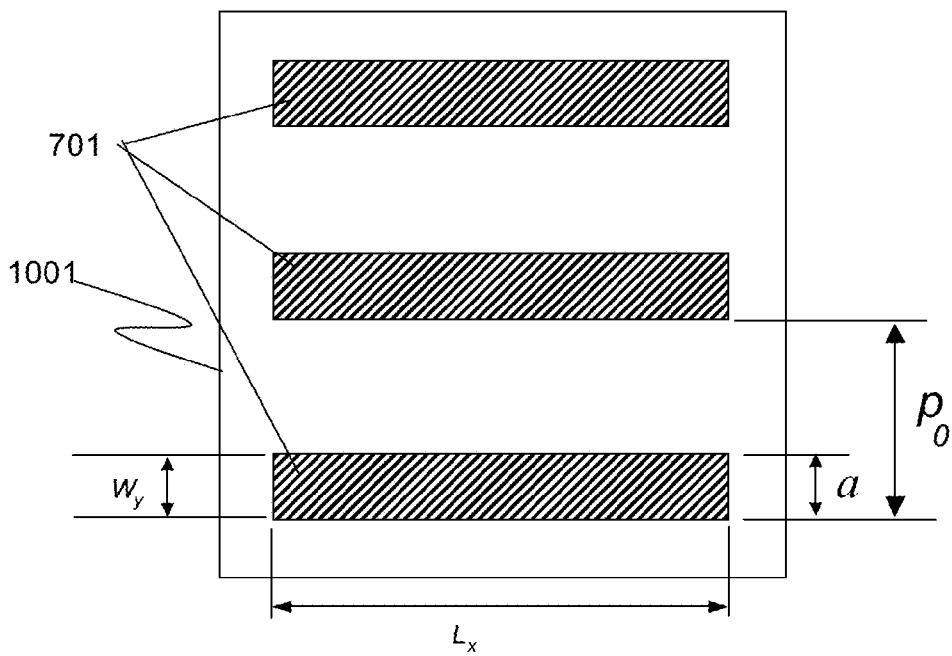
FIG. 29B illustrates a top view of the target of FIG. 29A.
Figure 29C:
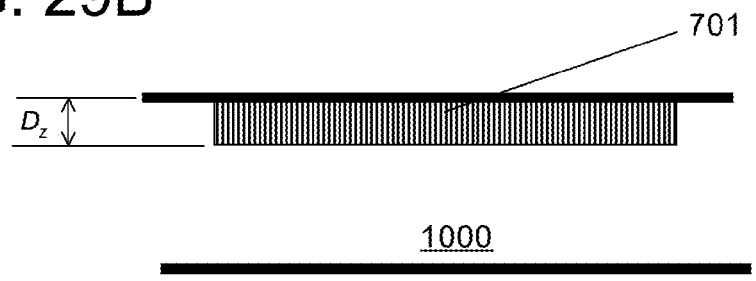
FIG. 29C illustrates a side/cross-section view of the target of FIGS. 29A and 29B.

FIG. 29 illustrates a region 1001 of a target as may be used in some embodiments of the invention, such as that previously illustrated in FIG. 13, that comprises an array of linear sub-sources 701 with microstructures in the form of right rectangular prisms comprising x-ray generating material arranged in a regular array. FIG. 29A presents a perspective view of the three microstructures 701 for this target, while FIG. 29B illustrates a top down view of the same region, and FIG. 29C presents a side/cross-section view of the same region.

In this embodiment, the lateral dimensions in the plane of the substrate are a width and length $W_x$ and $L_y$. The effective sub-source size a will correspond to the width $W_x$.

Figure 30:
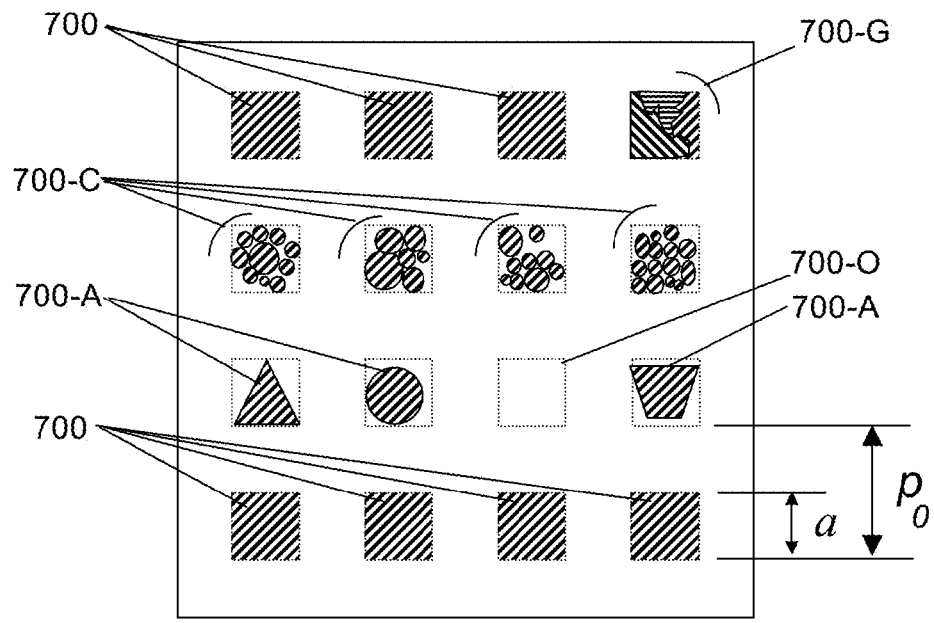
FIG. 30 illustrates variations in target structure for a target as shown in FIGS. 28A-C that may arise from processing variations.
Figure 31:
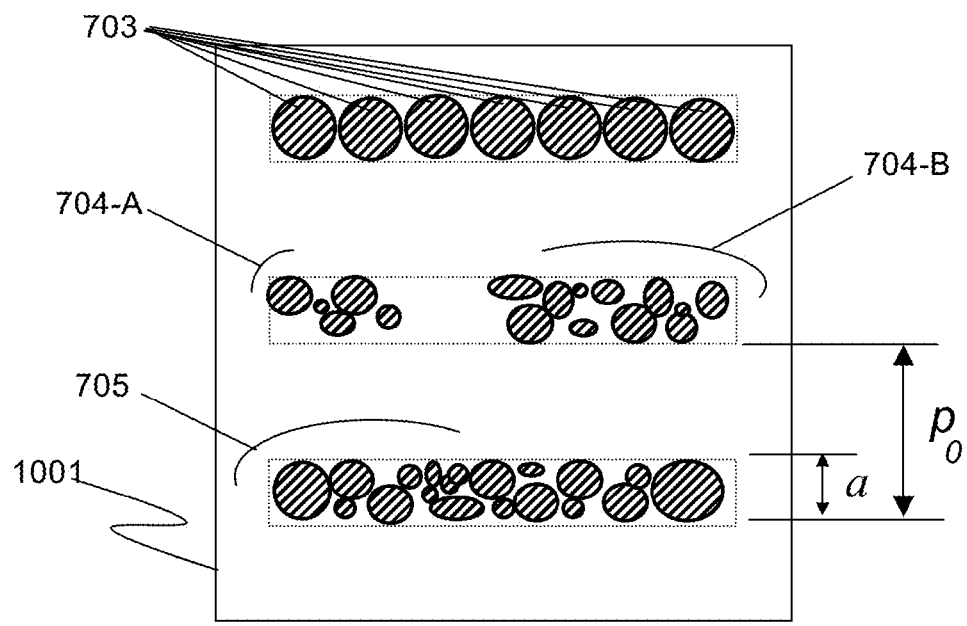
FIG. 31 illustrates variations in target structure for a target as shown in FIGS. 29A-C that may arise from processing variations.

FIGS. 30 and 31 illustrate a practical issue that may arise in forming the targets such as those illustrated in FIGS. 28 and 29. FIG. 30 illustrates variations possible with the grid of x-ray generating microstructures 700 as illustrated in FIG. 28, and FIG. 31 illustrates variations possible with the linear x-ray generating microstructures 701 as illustrated in FIG. 29.

In FIG. 30, odd-shaped microstructures 700-A of other geometric shapes may be formed. Likewise, voids 700-O may also appear where certain structures may be expected. Other deposition processes, for example deposition using pre-formed particles of x-ray generating material may create ensemble clusters of particles 700-C that, when bombarded with electrons, may still act as x-ray sub-sources similar in function to those that are produced by a uniform structure. Also shown in FIG. 30 is a microstructure with multiple crystal structures and grain boundaries 700-G that again may still produce x-rays similar to those that are produced by a uniform structure, but may be considered to comprise an ensemble of microstructures.

The effective x-ray sub-source size in all of these situations may be approximated using the size parameter a, even though the microstructures comprise particles that are considerable smaller.

FIG. 31 shows examples of ensemble microstructures as may occur when fabricating linear microstructures 701. If uniform pre-fabricated particles of x-ray generating material are created and coated onto the substrate, an ensemble of particles 703 of x-ray generating material may be formed. In other processes, if non-uniform particles are used, clusters of particles 704-A and 704-B may form, in some cases with a non-uniform distribution that may include gaps of voids. In other processes, an ensemble of particles 704 of x-ray generating material may approximate a line source of x-rays.

All of these ensembles, when bombarded with electrons, may still act as x-ray sub-sources similar in function to those that are produced by a uniform linear structure. The effective source size in these situations may be approximated using the size parameter a, even though the microstructures comprise particles that are considerable smaller.

Figure 32:
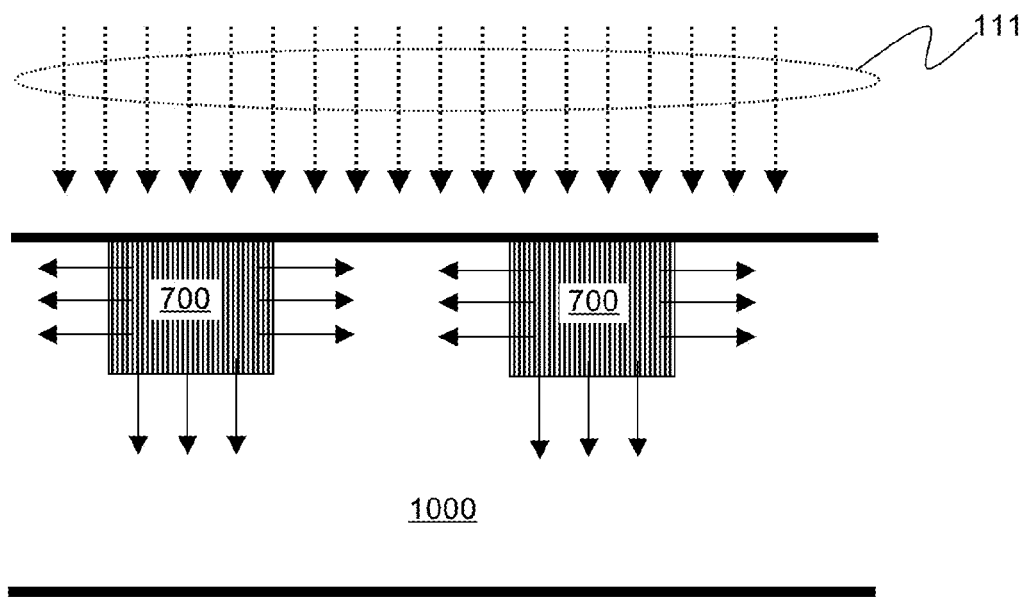
FIG. 32 illustrates a cross-section view of a portion of the target of FIGS. 28A-C and/or FIGS. 29A-C, showing thermal transfer to a thermally conducting substrate under electron beam exposure according to the invention.

The heat transfer that may occur under electron bombardment is illustrated with representative arrows in FIG. 32, in which the heat generated in sub-sources 700 embedded in a substrate 1000 is conducted out of the microstructures comprising the sub-sources 700 through the bottom and sides (arrows for transfer through the sides out of the plane of the drawing are not shown). The amount of heat transferred per unit time (ΔQ) conducted through a material of area A and thickness d given by:

$$\Delta Q = \frac{\kappa \cdot A \cdot \Delta T}{d} \quad [\text{Eqn. 14}]$$

where κ is the thermal conductivity in W/(m ° C.) and ΔT is the temperature difference across thickness d in ° C. Therefore, an increase in surface area A, a decrease in thickness d and an increase in ΔT all lead to a proportional increase in heat transfer.

Figure 33:
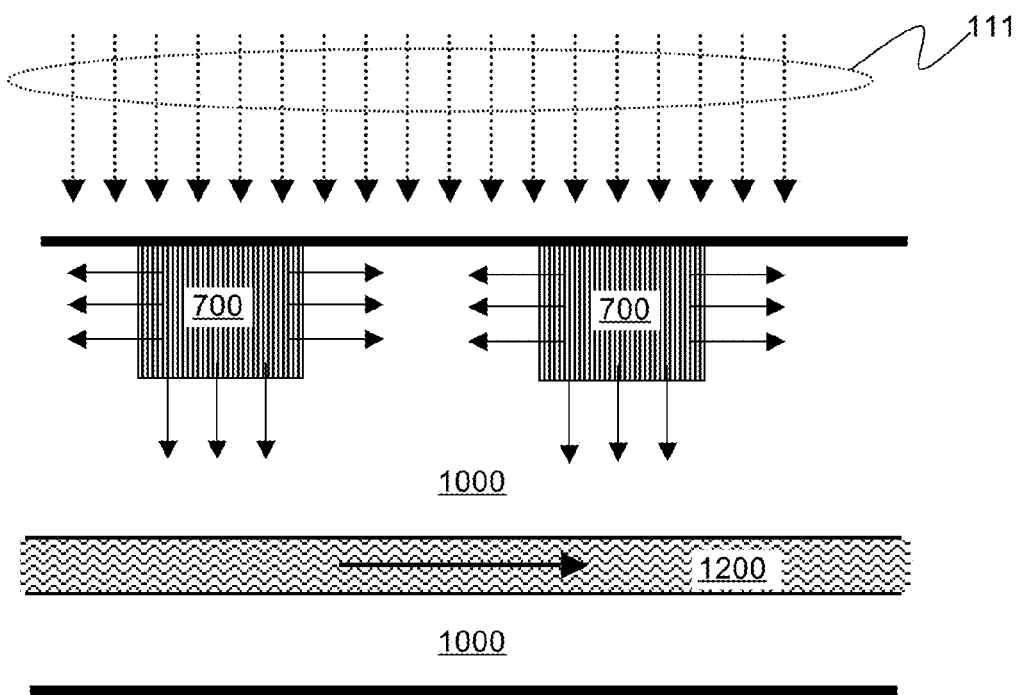
FIG. 33 illustrates a cross-section view of a variation of the target of FIGS. 28A-C, FIGS. 29A-C and/or FIG. 32 comprising a substrate with a thermal cooling channel according to the invention.

An alternative embodiment is illustrated in FIG. 33, in which the substrate additionally comprises a cooling channel 1200. Such cooling channels may be a prior art cooling channel, as discussed above, using water or some other cooling fluid to conduct heat away from the substrate, or may be fabricated according to a design adapted to best remove heat from the regions near the embedded microstructures 700.

Other target structures for various embodiments may be understood or devised by those skilled in the art, in which the substrate may, for example, be bonded to a heat sink, such as a copper block, for improved thermal transfer. The copper block may in turn have cooling channels within it to assist in carrying heat away from the block. Alternatively, the substrate may be attached to a thermoelectric cooler, in which a voltage is applied to a specially constructed semiconductor device. In these devices, the flow of current causes one side to cool while the other heats up. Commercially available devices, such as Peltier coolers, can produce a temperature difference of up to 70° C. across the device, but may be limited in their overall capacity to remove large amounts of heat from a heat source. Heat pipes containing a heat transfer fluid that evaporates and condenses, as are used for cooling CPU chips in server farms when compact design is a consideration, may also be used to cool the substrate.

Alternatively, the substrate can be attached to a cryogenic cooler, such as a block containing channels for the flow of liquid nitrogen, or be in thermal contact with a reservoir of liquid nitrogen or some other cryogenic substance, such as an antifreeze solution, to provide more extreme cooling. When the substrate comprises a material such as diamond, sapphire, silicon, or silicon carbide, thermal conductivity generally increases with decreasing temperature from room temperature. In such a case, designing the target so that it can withstand cooling to these lower temperatures may be preferred.

Figure 34:
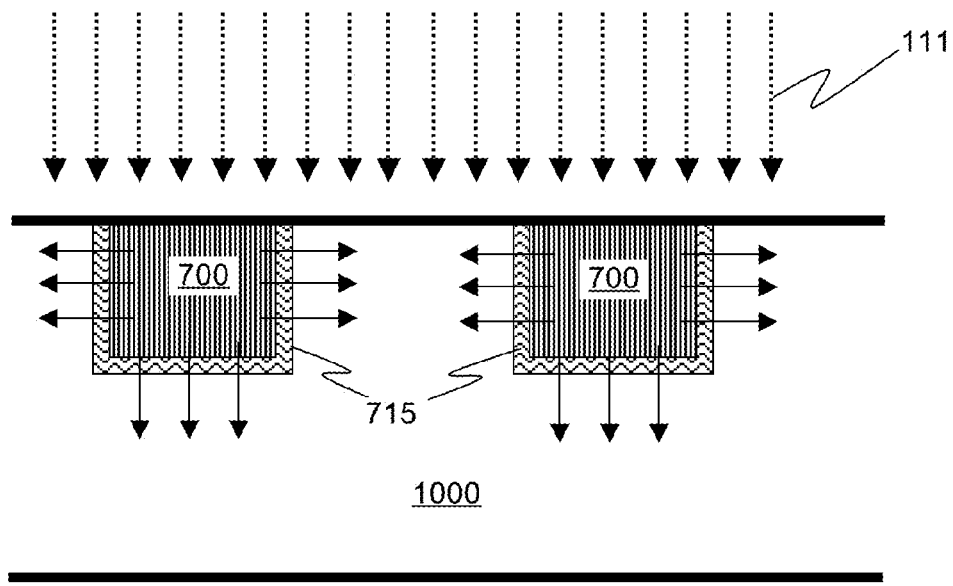
FIG. 34 illustrates a cross-section view of another variation of the target of FIGS. 28A-C and/or FIGS. 29A-C comprising an adhesion layer according to the invention.

FIG. 34 illustrates an alternative example of a target that may be used in embodiments of the invention in which the cavities formed in the substrate 1000 are first coated with an adhesion layer 715 (preferably of minimal thickness) before embedding the x-ray generating material that forms the microstructures 700. Such an adhesion layer may be appropriate in cases where the bond between the x-ray material and the substrate material is weak. The adhesion layer may also act as a buffer layer when the difference between thermal expansion coefficients for the two materials is large. For some choices of materials, the adhesion layer may be replaced or extended (by adding another layer) with a diffusion barrier layer to prevent the diffusion of material from the microstructures into the substrate material (or vice versa). For embodiments in which an adhesion and/or diffusion barrier layer is used, the selection of materials and thicknesses should consider the thermal properties of the layer as well, such that heat flow from the microstructures 700 to the substrate 1000 is not significantly impeded or insulated by the presence of the adhesion layer 715.

Figure 35:
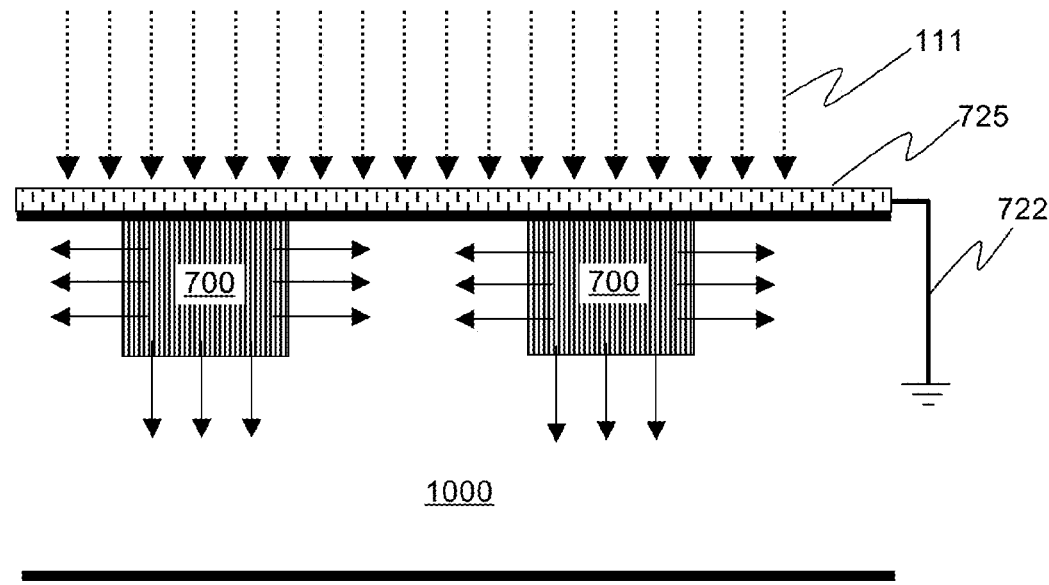
FIG. 35 illustrates a cross-section view of another variation of the target of FIGS. 28A-C and/or FIGS. 29A-C comprising an electrically conducting overcoat according to the invention.

FIG. 35 illustrates an alternative example of a target that may be used in an embodiment in which an electrically conducting layer 725 has been added to the surface of the target. When bombarded by electrons, the excess charge needs a path to return to ground for the target to function effectively as an anode. If the target as illustrated in FIGS. 28 and 29 were to comprise only discrete, unconnected microstructures 700 within an electrically insulating substrate material (such as undoped diamond), under continued electron bombardment, significant charge would build up on the surface. The electrons from the cathode would then not collide with the target with the same energy, or might even be repelled, diminishing the generation of x-rays.

This can be addressed by the deposition of a thin layer of conducting material that is preferably of relatively low atomic number, such as aluminum (Al), beryllium (Be), carbon (C), chromium (Cr) or titanium (Ti), that allows electrical conduction from the discrete microstructures 700 to an electrical path 722 that connects to a positive terminal relative to the high voltage supply. This terminal as a practical matter is typically the electrical ground of the system, while the cathode electron source is supplied with a negative high voltage.

Figure 36:
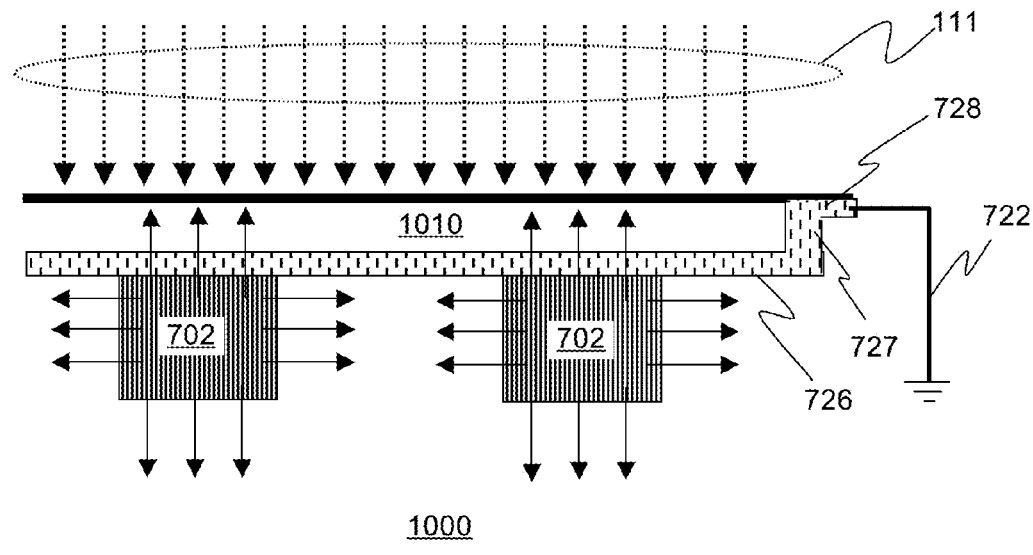
FIG. 36 illustrates a cross-section view of another variation of the target of FIGS. 28A-C and/or FIGS. 29A-C comprising buried x-ray material according to the invention.

FIG. 36 illustrates another example of a target that may be used in an embodiment of the invention, in which the sub-sources 702 are embedded deeper, or buried, into the substrate 1000. Such an embedded microstructure may be further covered by the deposition of an additional layer 1010, which may be, for example, diamond, providing the same heat transfer properties as the substrate. This allows heat to be conducted away from all sides of the buried sub-source 702. For such a situation and when the additional layer 1010 does not have sufficient electrical conductivity, it is advisable to provide a path 722 to ground for the electrons incident on the structure, which may be in the form of an embedded conducting layer 726 laid down before the deposition of the additional layer 1010. In some embodiments, this conducting layer 726 will have a "via" 727, or a vertical connection, often in the form of a pillar or cylinder, that provides an electrically conducting structure to link the embedded conducting layer 726 to an additional conducting layer 728 on the surface of the target, which in turn is connected to the path 722 to ground, or the high voltage supply.

Figure 37:
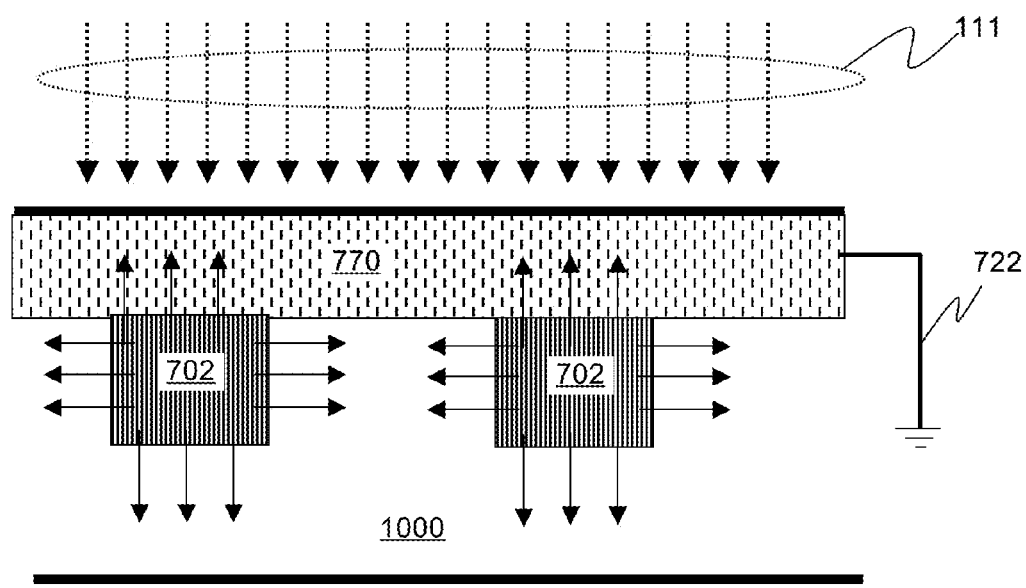
FIG. 37 illustrates a cross-section view of another variation of the target of FIGS. 28A-C and/or FIGS. 29A-C comprising buried x-ray material and a thick thermally and electrically conducting overcoat according to the invention.

FIG. 37 illustrates another example of a target that may be used in embodiments of the invention, in which the sub-sources 702 are again buried within the substrate. However, in this embodiment, instead of first providing an electrically conducting layer followed by the deposition of an additional cap layer, in this embodiment only a single layer 770 is deposited, selected for a combination of electrical properties and thermally conducting properties. This may be, for example, a deposition of carbon nanotubes (Z=6) oriented vertically relative to the surface, such that they conduct both heat and electrons away from the buried microstructures 702. This single layer 770 may in turn be connected to a path 722 to ground to allow the target to serve as an anode in the x-ray generation system. Alternatively, the material of the layer 770 may be selected to comprise aluminum (Al), beryllium (Be), chromium (Cr), or copper (Cu).

Figure 38:
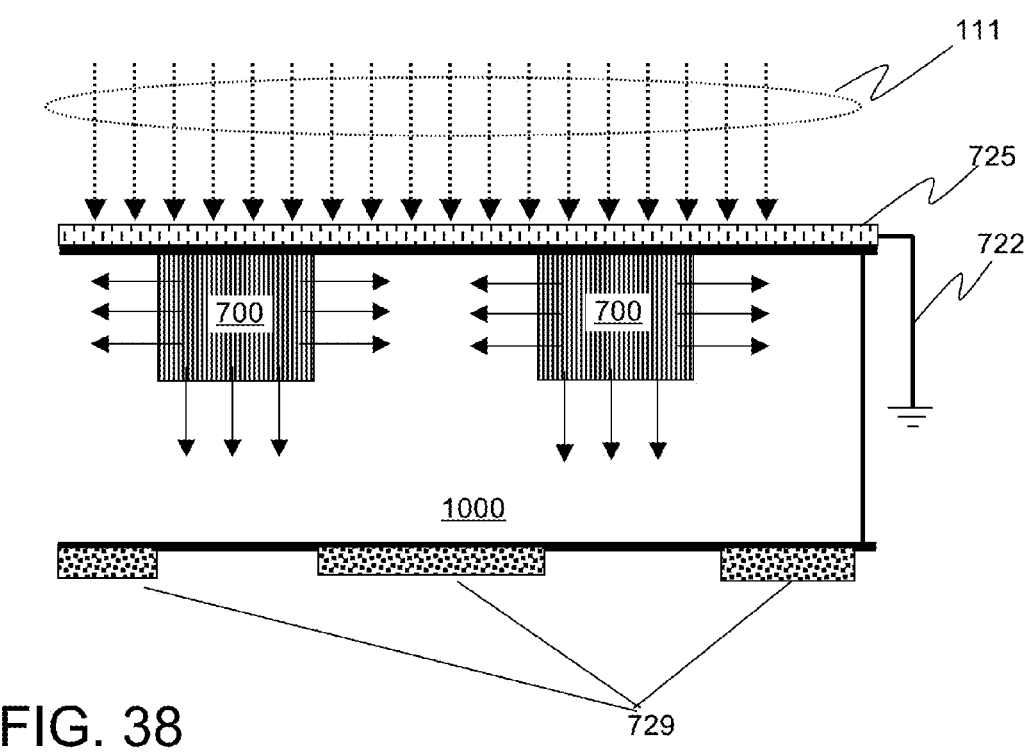
FIG. 38 illustrates a cross-section view of another variation of the target of FIGS. 28A-C and/or FIGS. 29A-C comprising an additional blocking structures on the back surface of the substrate, to block the transmission of x-rays produced by the substrate
Figure 39:
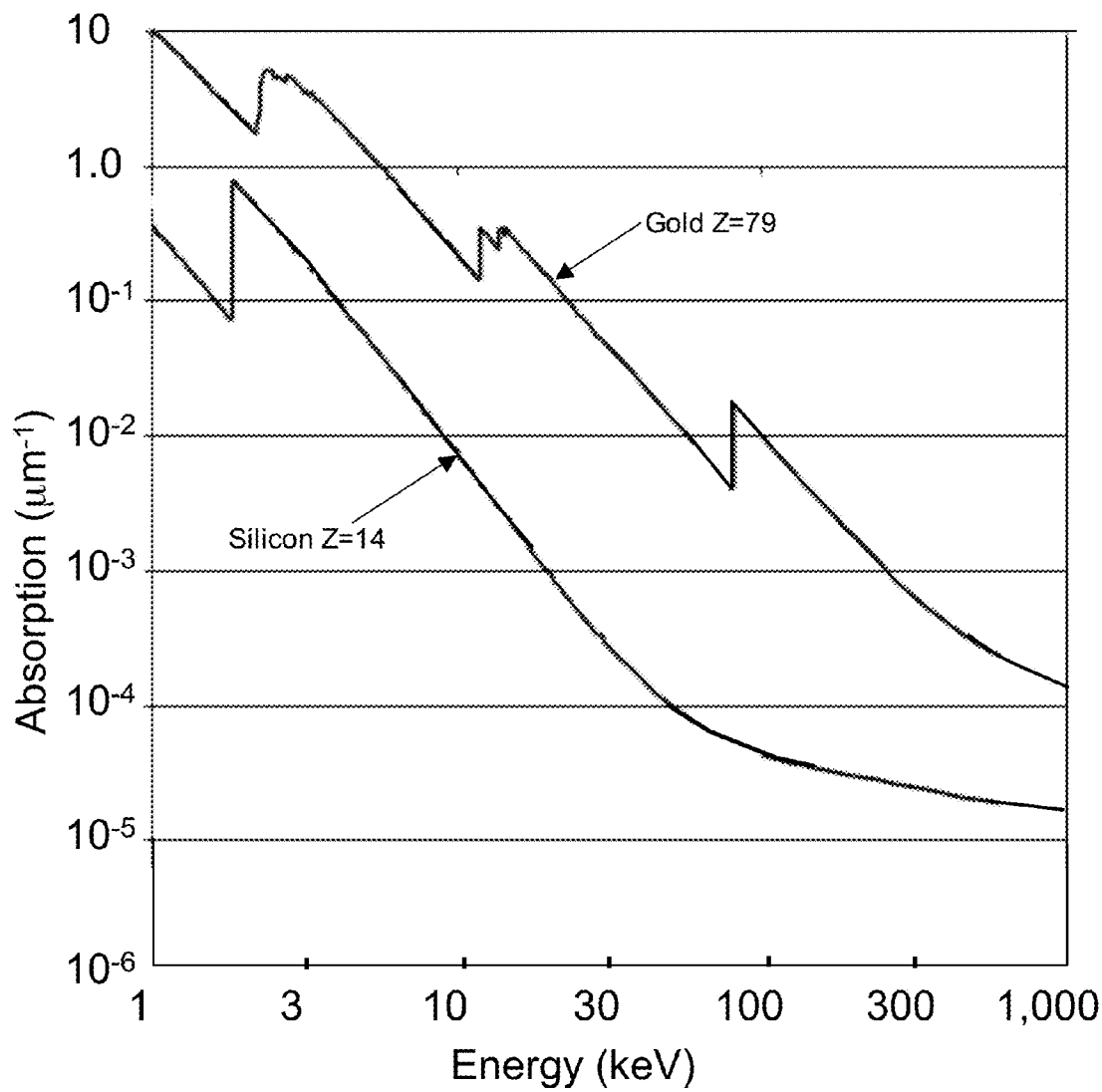
FIG. 39 illustrates a plot of the x-ray absorption of gold and silicon as a function of x-ray energy.

FIG. 38 illustrates another variation of an embodiment, in which additional patterns of blocking material 729 have been deposited on the backside of the target substrate 1000. If the figure of merit for the selected material combination, as discussed above in Table II, is not large, there may still be significant x-rays generated by the substrate that will reduce contrast in the image. These substrate-generated x-rays can be blocked by a deposition of a suitable material, such as gold, as blocking structures 729. Gold (Z=79) has a strong x-ray absorption, as illustrated in FIG. 39. Processes to deposit these blocking structures may comprise standard deposition processes, and an alignment step may be needed to ensure alignment with the x-ray generating structures on the opposite side.

It should be clear to those skilled in the art that although several embodiments have been presented separately in FIGS. 26-38, and various processes for their manufacture will be presented later, the elements of these embodiments may be combined with each other, or combined with other commonly known target fabrication methods known in the art. For example, the buried sub-sources 702 of FIG. 37 may also comprise multiple grains of microstructures, as was illustrated in FIGS. 30 and 31. Likewise, the adhesion layer 715 as illustrated in FIG. 34 may also be applied to fabrication of embedded sub-sources 700 as shown in FIG. 35. The separation of these alternatives is for illustration only, and is not meant to be limiting for any particular process.

Although the sub-sources illustrated in FIGS. 26-38 have been shown as regularly spaced patterns with uniform size and shape, a regular pattern of sub-sources having non-uniform size and shape, can also be used in some embodiments of the invention. Additionally, each sub-source within a regular periodic pattern may further be comprised of multiple smaller microstructures of non-uniform sizes and shapes. These smaller microstructures may be non-regular and do not necessarily need to have similar x-ray emission characteristics or strength, so as long as the larger sub-sources that each group of microstructures comprise are periodic in nature.

Likewise, although some embodiments have been described with microstructures in, for example, the shape of right rectangular prisms, fabrication processes may create structures that have walls at angles other than 90°, or do not have corners that are exactly right angles, but may be rounded or beveled or undercut, depending on the artifacts of the specific process used. Embodiments in which the microstructures are essentially similar with the shapes described herein will be understood by those skilled in the art to be disclosed, even if process artifacts lead to some deviation from the shapes as illustrated or described.

In other embodiments of the system, a periodic attenuating grating $G_0$ such as are used in the prior art Talbot-Lau interferometers may also be used in conjunction with the source of the invention, so that the x-rays produced by the substrate material surrounding the sub-sources are further attenuated, allowing greater monochromaticity and therefore higher spatial coherence for the source. The apertures of the grating should be coincident with projections of the microstructured x-ray sub-sources, or may, in some embodiments, be placed at a Talbot fractional or integer distance downstream of the source and with the apertures coincident with the source self-images. It is preferable that the grating $G_0$ is of high atomic number and relatively low aspect ratio, for ease of manufacturability.

3. Application to Metrology and Inspection

Conventional x-ray analysis or imaging systems have thus far relied on uniform illumination of an object over an extended area, or the use of an illumination beam focused onto a particular feature. For example, information about particular devices or features on a semiconductor IC or IC package, such as transistor structures or periodic through-silicon vias (TSVs), may be gathered by observing x-ray fluorescence from those devices or structures. However, if illuminated by flood illumination, additional x-ray signal from the surrounding silicon wafer may contribute to the detected signal as background and reduce signal-to-noise ratio of the information from the features, and reduce sensitivity. Similarly, if an x-ray beam is focused on a single feature, information about that particular feature may be gathered, but given that there may be millions or even billions of such features in a given IC, determination of the statistical properties of the multiple features will take an inordinate amount of time and is very inefficient.

However, if certain substantially similar features are placed in a periodic pattern, such as transistors or TSVs often are, an approach that selectively illuminates these periodic features with a periodic pattern of illumination may provide information about a large number of the features simultaneously with high signal-to-noise ratio and with high measurement throughput. In such a case, it is useful to concentrate the x-ray illumination solely on the features under observation, and reduce as much as possible the x-ray signals from the surrounding regions.

As discussed above, in the last decade, Talbot-based imaging techniques have been developed for x-ray grating-based phase contrast imaging. The Talbot effect occurs when a beam-splitting grating is illuminated with a beam of sufficiently large spatial coherence and sufficiently narrow spectral bandwidth, and as a result, periodic interference patterns (Talbot patterns) are formed at the fractional Talbot distances on the downstream side of the grating.

Diffraction gratings of both phase-type and absorption-type produce intensity modulations downstream at different defined Talbot distances as has been previously presented in references such as "X-Ray Phase Imaging with Talbot Interferometry" by A Momose et al. in *BIOMEDICAL MATHEMATICS: Promising Directions in Imaging, Therapy Planning, and Inverse Problems* (Medical Physics Publishing, Madison Wis., 2010), pp. 281-320. The intensity modulations of the Talbot pattern vary from zero at the regions of destructive interference (nodes) to two times the intensity incident on the grating at a magnification of 1, and may be scaled by the square of a magnification factor defined as $(R+z/R)$, where z is the distance of the intensity modulation from the diffraction grating and R is the distance of the diffraction grating from the x-ray source. This principle has been used to great extent for obtaining phase information from samples, but so far, has not been employed as a useful phenomenon for other x-ray modalities.

Described in this Section are various embodiments a method and apparatus that can accomplish measurement of large numbers of periodic features through the use of periodic x-ray microbeams generated as part of a Talbot interference pattern. This use of patterned illumination can be used to characterize, analyze, and measure periodic structures that are naturally occurring or manmade.

The Talbot interference pattern results from a beam splitting grating such as has been described above. These periodic microbeams can be utilized to probe specific and periodic regions with established x-ray techniques (such as x-ray absorption, small angle x-ray scattering (SAXS), x-ray fluorescence (XRF), x-ray diffraction (XRD), X-ray reflectivity (XRR), etc.) singularly or in combination.

The periodic arrays of x-ray microbeams may have sub-100 nm size in at least one dimension for high spatial characterization. Spatial resolution down to 10 nm can be obtained to simultaneously probe multiple periodic regions in an object to be examined, as opposed to conventional methods that probe using either one focused illumination beam or one large uniform illumination beam.

It is well-known from work on the Talbot effect and prior art that under illumination beam with sufficient spatial coherence a periodic structure such as a 1-D or 2-D transmission grating can produces intensity patterns with strong contrast (up to 100%) due to constructive and destructive interference at well-defined distances (the distances may depend on several factors, including if the diffraction grating is absorbing or phase-shifting, the phase shift induced, and the line-space ratio of the grating, as will be described in further detail below). Designing the beam splitting grating to produce a periodic pattern of x-ray microbeams with particular dimensions corresponding to an object with periodic structures, such as transistors, interconnects, and through silicon vias (TSVs) on a semiconductor wafer or chip, and placing that object with periodic structures in a position such that the microbeams are aligned to illuminate only the locations of the periodic structures containing particular devices or structures enables their analysis and characterization with high signal to noise ratio and high efficiency.

Depth-wise probing is also possible by moving the object to be examined along the x-ray beam axis (z) so that the Talbot interference pattern nodes are shifted from near the surface of the object to deeper within the object. This would allow illumination of multiple regions at different depths, allowing, for example, mapping differences in small angle scattering, diffraction, fluorescence, absorption, or reflectivity measurements as a function of depth.

Also described in this Section are a method and design of an x-ray system to obtain an x-ray probe with specific intensity pattern and probe size with known designs of sources with sufficient spatial coherence for the Talbot effect (including: microfocus x-ray source, liquid metal jet source with small spot size, an extended x-ray source with an absorption grating) or an x-ray source with a microstructured anode.

Also described in this Section are various embodiments of the invention that can achieve the use of periodic x-ray microbeams for chemical analysis of specific periodic regions of the sample, by collecting x-ray fluorescence from specified regions of the object to be examined (e.g. compositional analysis, layer thickness determination, etc.) while reducing the production of fluorescence signal from the regions of the object not illuminated by the periodic x-ray microbeams.

Also described in this Section are various embodiments of the invention that can achieve the use of periodic x-ray microbeams to perform x-ray diffraction analysis of specific periodic regions in a sample; for example performing crystallographic structure determination (e.g. crystallographic structure determination, strain analysis) and layer thickness measurements. This diffraction measurement made using the invention may be carried out using x-rays in transmission, but may also be performed using reflected x-rays.

Also described in this Section are various embodiments of the invention that can achieve the use of periodic x-ray microbeams to obtain statistical structural information of periodic structures using small angle scattering techniques. For an exemplary application to semiconductor devices, the enabled capabilities encompass information such as the determination of critical dimensions, exemplary parameters that include sidewall angle, pitch, and linewidth roughness.

Also described in this Section are various embodiments of the invention that use periodic x-ray microbeams for the characterization, analysis, and measurement of thin films to make a structural determination of periodic structures using x-ray reflectivity information. As an example, this reflectivity measurement may be used to determine such parameters as layer thickness, density, and roughness in a multi-layered structure. These measurements made using the invention may be carried out in transmission through a wafer or device using x-rays reflected from side walls of high aspect ratio structures, but may also be performed using reflected x-rays from surfaces and interfaces.

Also described in this Section are various embodiments of the invention that can achieve the characterization, analysis, and measurement of periodic structures of a multitude of samples across a broad range of applications using a combination or a subset of the methods noted above to obtain complementary and comprehensive information of the periodic structures.

The embodiments of the invention as described herein may be used to examine and analyze man-made objects such as semiconductor wafers, integrated circuits (ICs), IC packaging, or other electronic components, a manufactured material or device (such as a grating), a protein crystal structure, or a chemical or polymeric compound, provided that they are substantially similar in terms of physical parameters to be measured (such as shape, material composition, crystallography, texture, etc) and periodically positioned. The embodiments of the invention disclosed herein may be applied to these techniques when a Talbot interference fringe (of varied intensity) is produced and regions of interest within a sample are aligned with one or more of the antinodes (regions of constructive interference) of the Talbot interference fringe.

3.2. A Method Involving Talbot Fringes.

Figure 4:
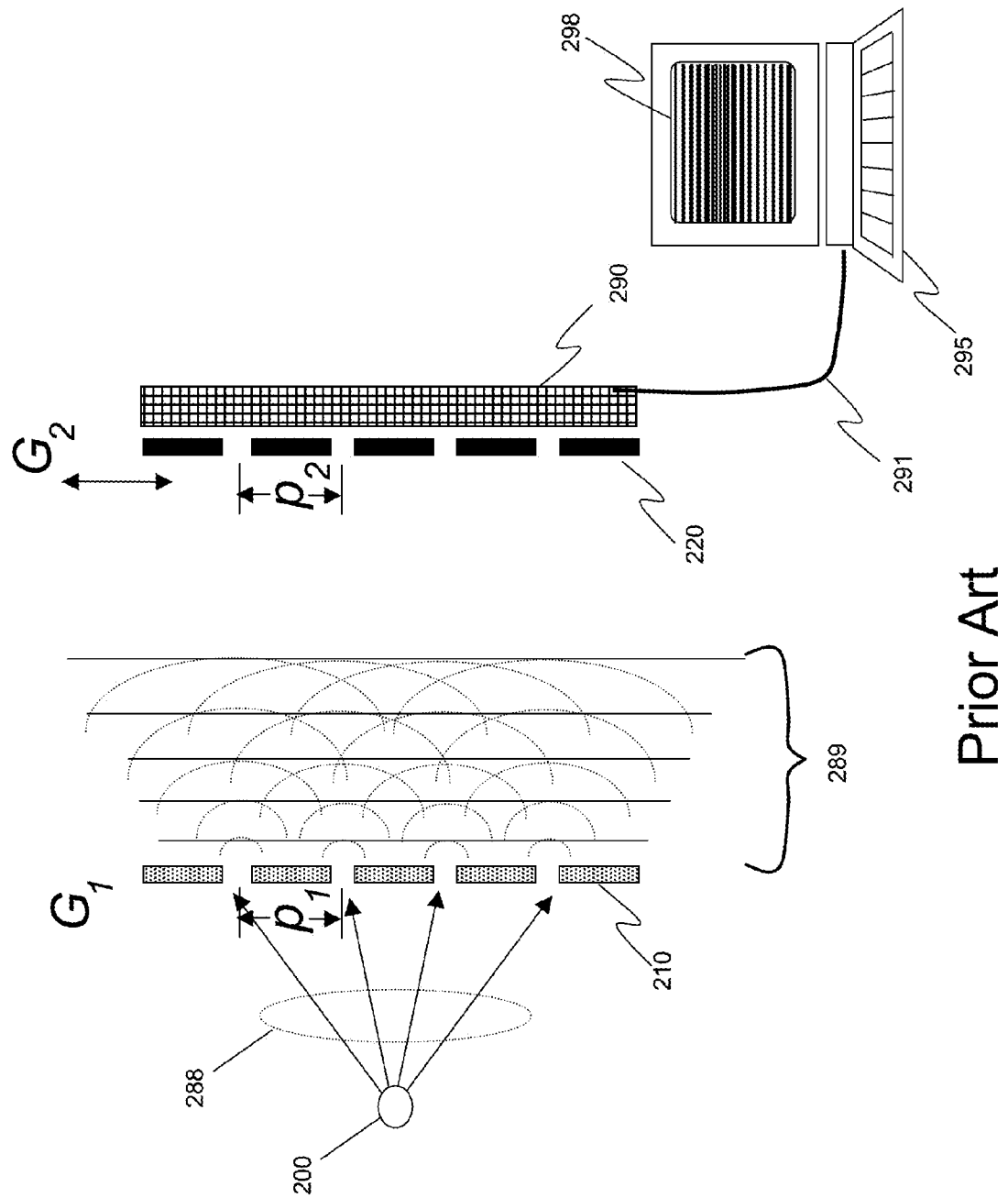
FIG. 4 illustrates a cross section view of the prior art x-ray grating interference system of FIG. 3.
Figure 5:
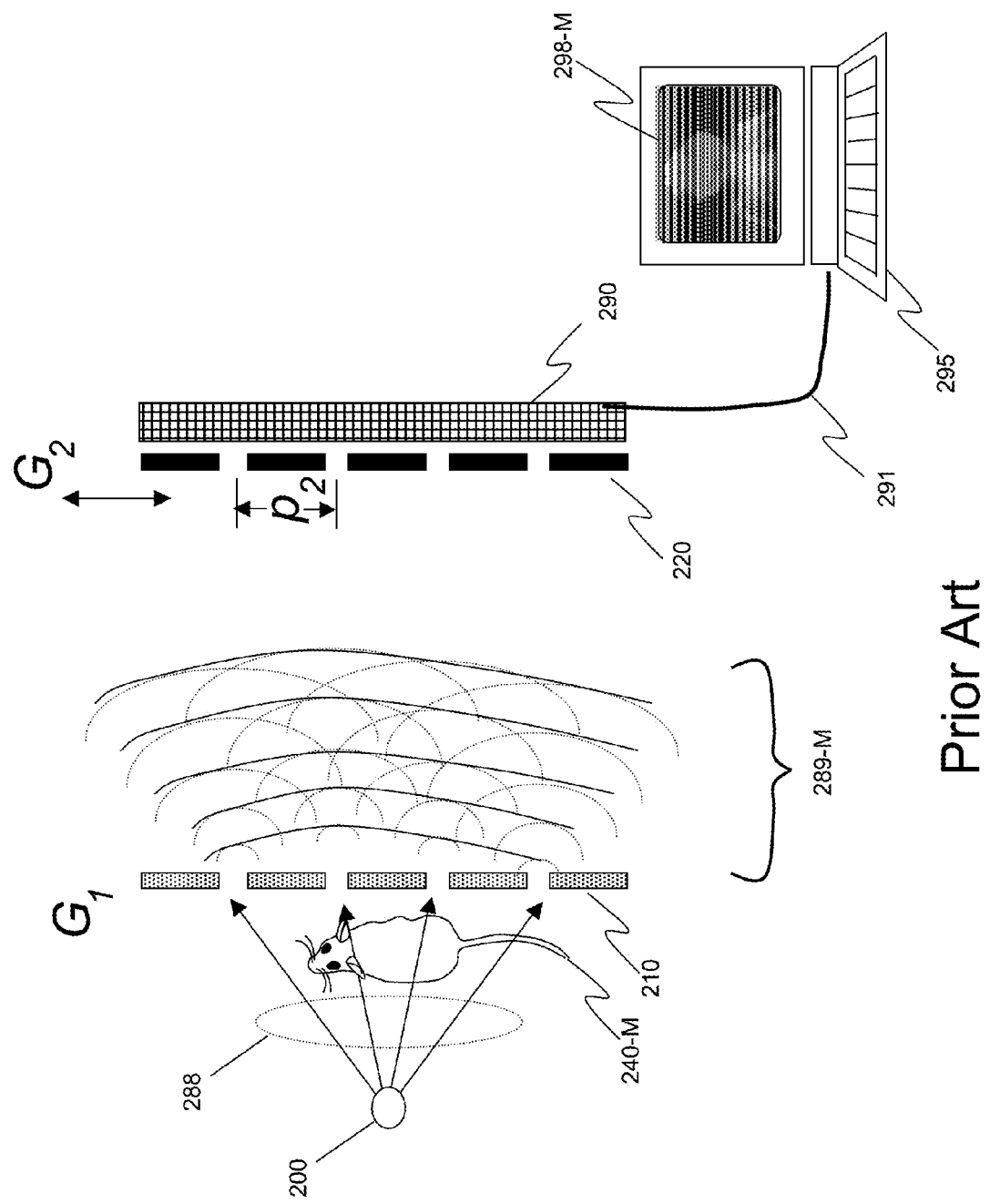
FIG. 5 illustrates the prior art x-ray grating interference system of FIG. 3 used to form an x-ray contrast image of a mouse.
Figure 6:
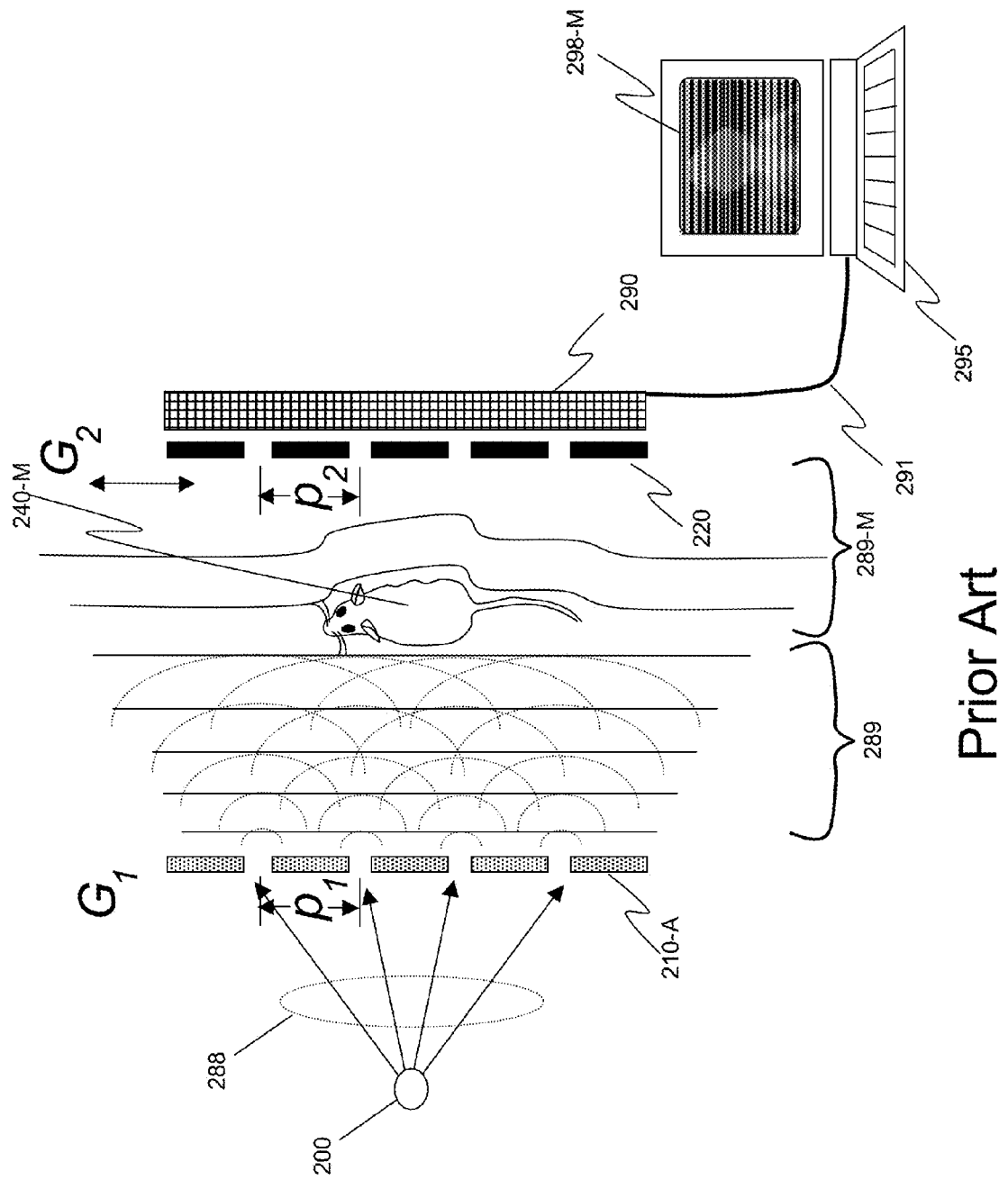
FIG. 6 illustrates a variation of the prior art x-ray grating interference system of FIG. 3 used to form an x-ray contrast image of a mouse.
Figure 40A:
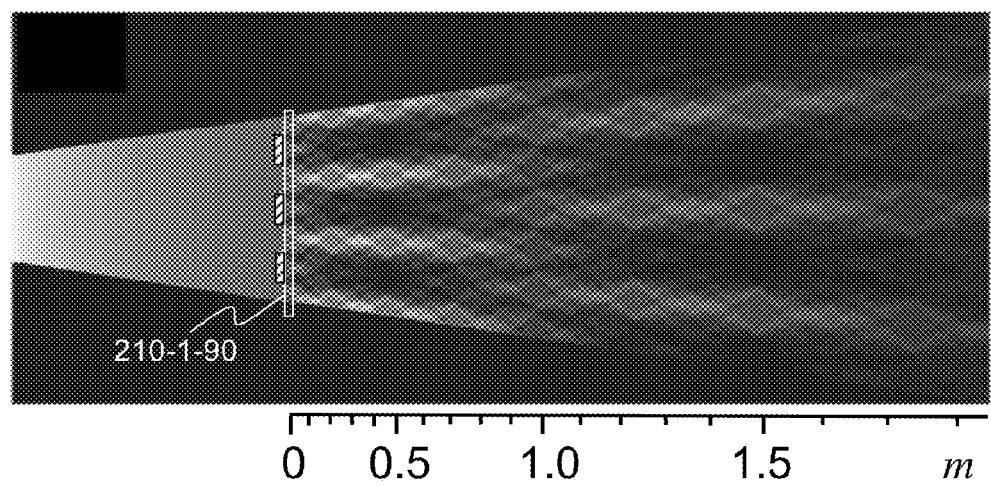
FIG. 40A illustrates an example of a Talbot interference fringe pattern for a 1:1 $\pi/2$ phase shifting grating.
Figure 40B:
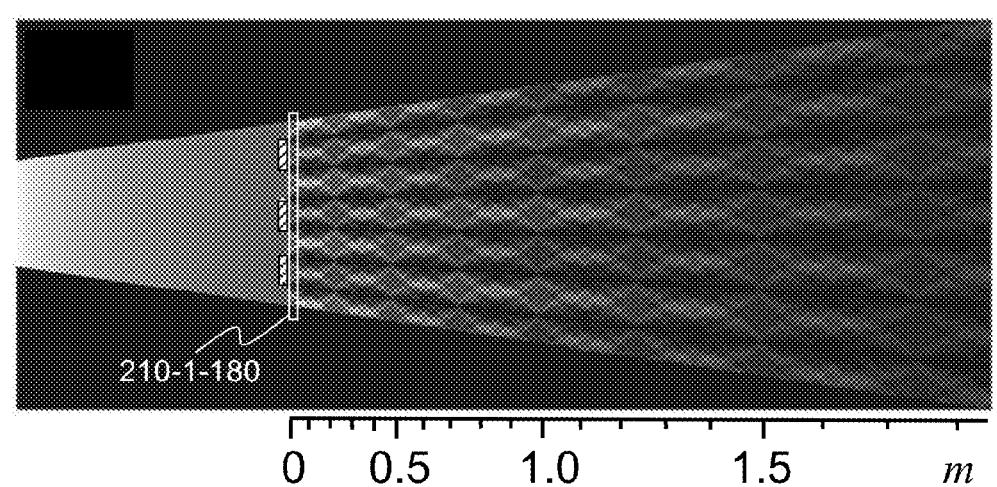
FIG. 40B illustrates an example of a Talbot interference fringe pattern for a 1:1 $\pi$ phase shifting grating.
Figure 40C:
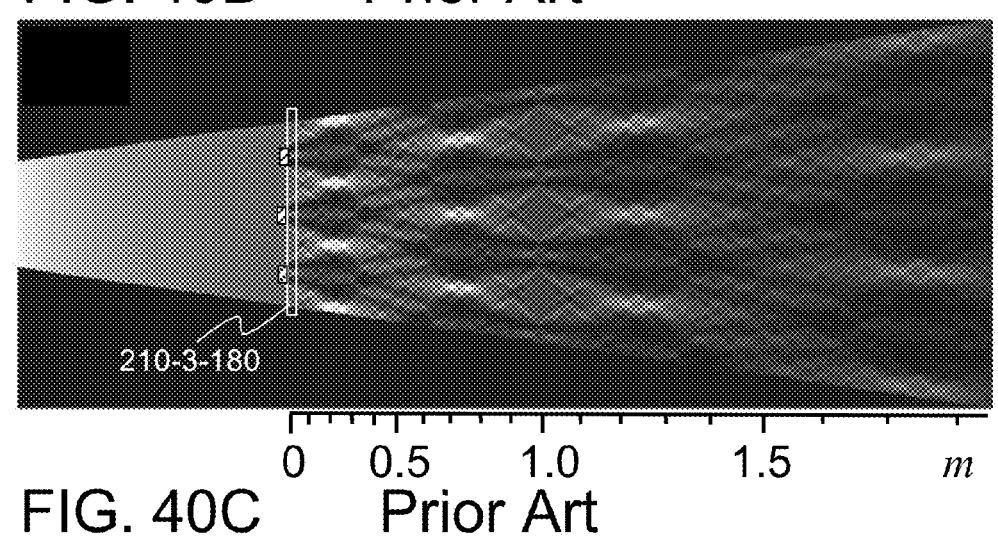
FIG. 40C illustrates an example of a Talbot interference fringe pattern for a 1:3 $\pi$ phase shifting grating.

Additional examples of Talbot interference patterns derived from the examples of FIG. 4 of "X-Ray Phase Imaging with Talbot Interferometry" by A. Momose et pp. 281-320 of *BIOMEDICAL MATHEMATICS: Promising Directions in Imaging, Therapy Planning, and Inverse Problems* (Medical Physics Publishing, Madison Wis., 2010), are shown in FIG. 40. FIG. 40A illustrates the intensity pattern produced by a grating 210-1-90 with lines (shown in cross section) introducing a π/2 radian phase shift in a 1:1 width ratio with adjacent spaces. FIG. 40B illustrates the intensity pattern produced by a grating 210-1-180 with lines (shown in cross section) introducing a t radian phase shift in a 1:1 width ratio with adjacent spaces. FIG. 40C illustrates the intensity pattern produced by a grating 210-3-180 with lines (shown in cross section) introducing a t radian phase shift in a 1:3 width ratio with adjacent spaces. All the gratings of FIG. 40 have a Ronchi (e.g. line/space square wave) profile, and for these illustrations, a point radiation source with sufficient spatial coherence. The beam splitting gratings are illuminated with diverging x-ray illumination, and the period of the fringes therefore generally increases with the distance from the grating. The scale factor m along the axis is described in the Momose reference as generally producing a self-image when m is even, and shifted Talbot self-images for phase shifting beam splitting gratings when m is odd.

In many embodiments, this beam splitting diffraction grating is that of a phase grating of low absorption but producing considerable x-ray phase shift of either $\pi/2$ or $\pi$ radians, or some other specified or predetermined value such as a fraction of $\pi$. These gratings may be one-dimensional or two-dimensional in nature. In some embodiments, the object being examined is placed downstream of the diffractive grating at a fractional Talbot distance $D_N$ represented by the equation $$D_N = N_a \frac{p_1^2}{8\lambda} = \frac{N_a}{16} D_T \qquad [\text{Eqn. 15}]$$

where $p_1$ is the period of the beam splitting grating, $D_N$ is the fractional Talbot distance for a plane wave illumination, $\lambda$ is the mean x-ray wavelength, and $N_a$ is the Talbot fractional order (N=1, 2, 3, . . . ) at which the object is placed. In some embodiments, the object is placed downstream of the diffractive grating at a distance that is not a fractional Talbot distance, but instead located at a distance wherein the wavefront is comprised of regions of anti-nodes and nodes that correspond to the periodic regions of interest for analysis.

Depending on the grating parameters (e.g. a $\pi$ phase shifting grating versus a $\pi/2$ phase shifting grating), optimal Talbot distances ($N_a$) may be chosen for interference patterns of interest or best suited for the application.

In a method according to the invention, the following steps will be followed to conduct an ensemble measurement of a periodic object. These are illustrated in the flow diagram shown in FIG. 41.

Figure 7:
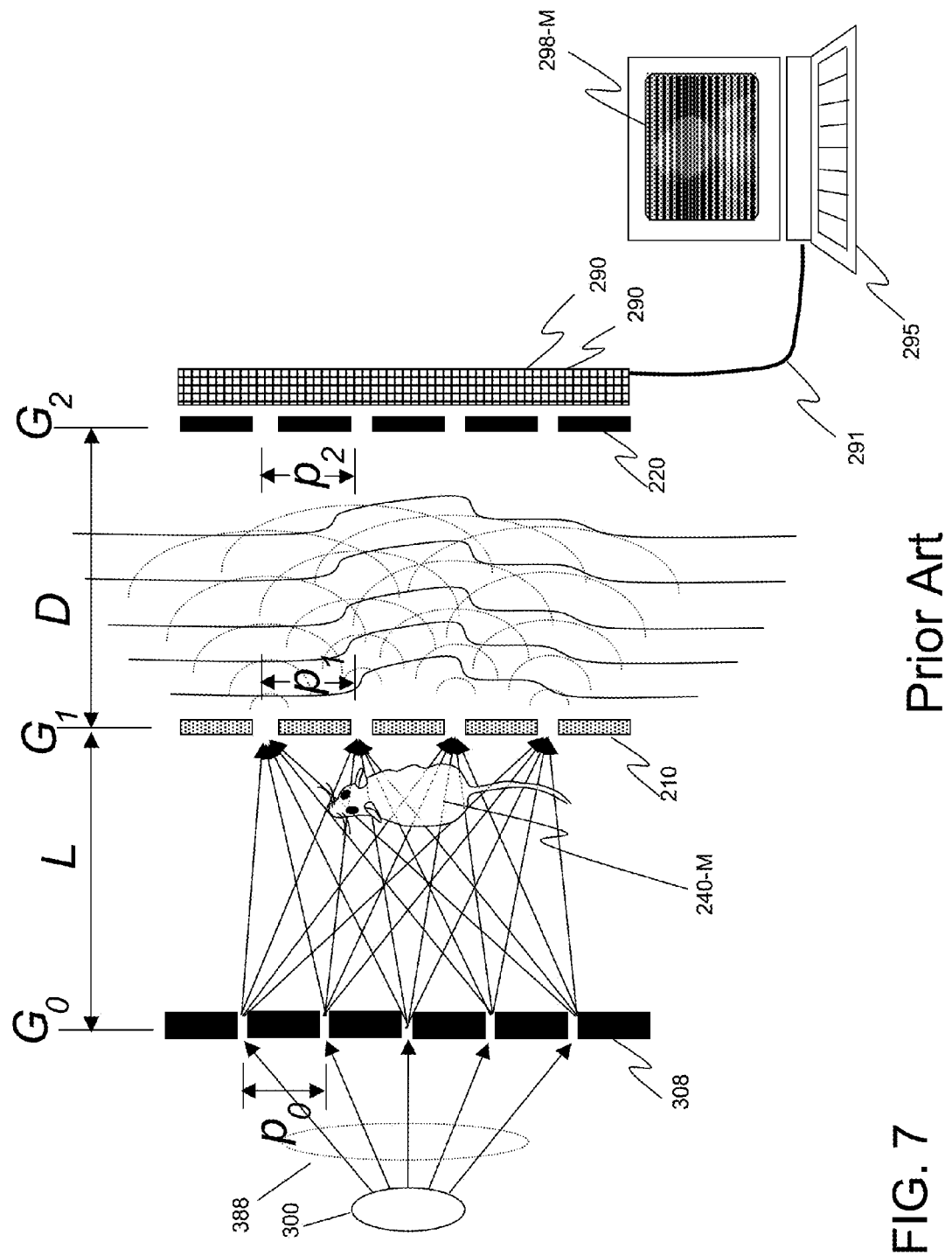
FIG. 7 illustrates a prior art Talbot-Lau interferometer being used to form an x-ray contrast image of a mouse.
Figure 8:
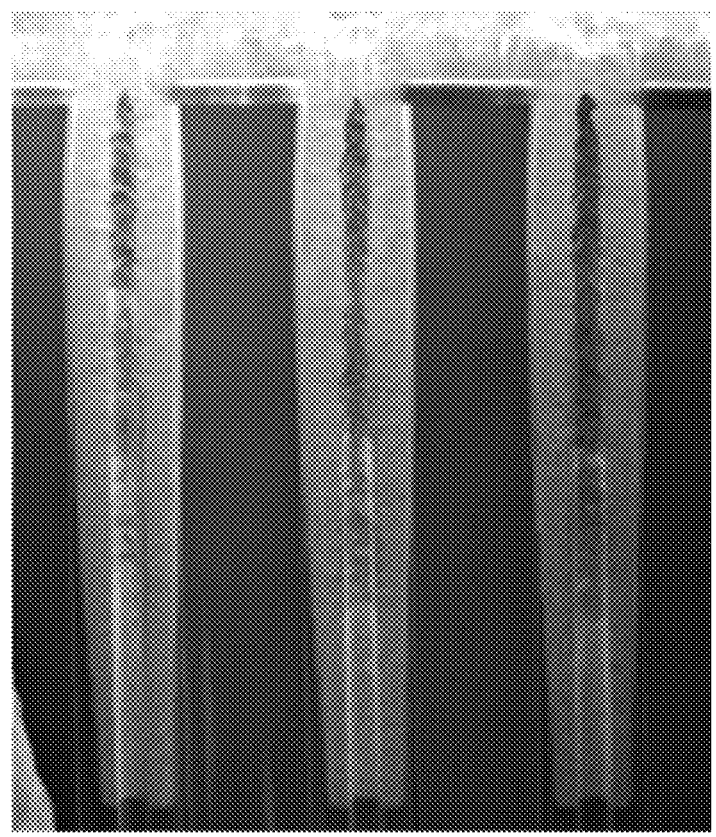
FIG. 8 illustrates a published example of a periodic object (defective TSVs in a silicon wafer) that may be examined using the methods of the invention.
Figure 41:
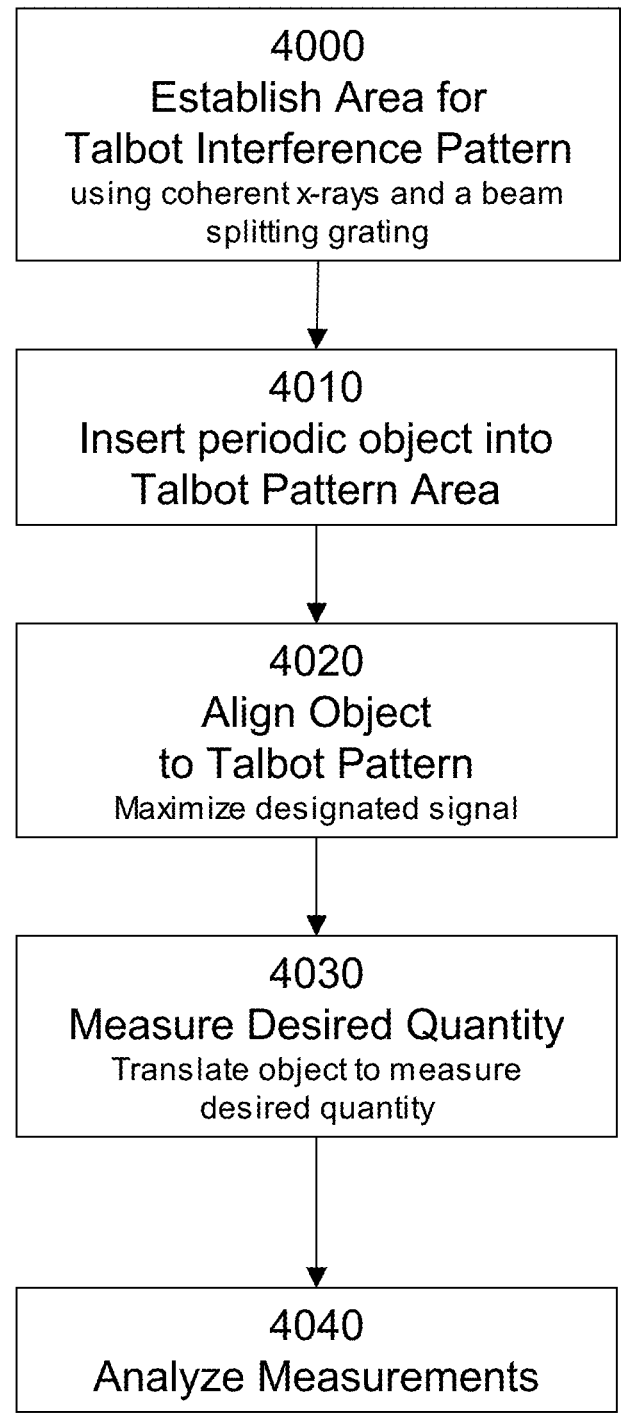
FIG. 41 illustrates the steps of illuminating the periodic structures of an object using structured illumination according to the invention.

First, as shown in FIG. 41, step 4000, a coherent or partially coherent source of x-rays is directed to interact with a beam splitting grating, a Talbot interference pattern of x-rays is established in a designated region of space. This may utilize x-rays from any source with enough coherence to establish Talbot fringes of high contrast (generally with contrast greater than 20%), and may utilize a point-source or microfocus source of x-rays, as was illustrated in FIG. 4, an extended x-ray source used in combination with a patterned aperture, as was illustrated in FIG. 7, or an array source of x-rays from discrete structures embedded in a thermally conducting substrate, as was illustrated in FIGS. 9-16 and 19-38. Some embodiments may also comprise a microfocus source with a collimating x-ray optic, such as a parabolic reflecting optic, downstream of the source to produce a parallel x-ray beam. The configurations disclosed may furthermore optionally comprise a monochromator, such as a double crystal monochromator or a channel cut monochromator, or any x-ray filter to narrow the bandwidth of the x-ray beams.

The beam splitting grating may be any grating suited to forming a Talbot interference pattern, such as absorption gratings, phase-shifting gratings, or combinations thereof, with apertures/phase shifters with any one of a variety of patterns, as has been illustrated elsewhere in this disclosure. One feature of the beam splitting grating, however, is that is will generally be designed to be used in combination with a particular object having a particular periodic pattern, such as an IC package with TSVs at a known pitch. The Talbot pattern created will be matched in dimension and pitch to the object to be examined.

In the next step 4010, the object with periodic structures to be examined will be inserted into the region at a predetermined location where the desired pattern of nodes and antinodes will be formed. It may generally be inserted with the x-rays off, or inserted while the x-rays are on and the Talbot pattern is in effect. It may be inserted using a mount, such as 5-axis mount, a rotation stage, or other holder with the ability to rotate and/or translate the object, which has been already positioned in the area where the Talbot fringes will be established.

In any case, once the object is in place, the object will be illuminated with the Talbot pattern.

In the next step 4020, the object will be aligned to the Talbot pattern. As discussed above, this will typically involve positioning the periodic structures using translation and/or rotation so that the bright anti-nodes of the Talbot pattern overlap the periodic structures. The alignment may match the pitch of the structures to the pitch of the Talbot pattern with a 1:1 relationship, or may be equal to an integer multiple of the periodic structures or regions of interest of the object.

This alignment of the periodic illumination to the periodic features can be carried out by observing the overall transmitted x-rays, and either maximizing the transmitted signal (in the case that the periodic objects are more transmissive) or minimizing the transmitted signal (in the case that the periodic structures are more absorbing).

Alignment can also be carried out using, for example, fluorescence, in that a fluorescence signal from the object is detected in any known configuration such as with an x-ray signal detector placed on the same side as the x-ray source relative to the object. The alignment is adjusted until the fluorescence signal detected is maximized if the fluorescence signal for the x-ray energy used is higher from the periodic objects, or minimized if the fluorescence signal is lower for the periodic objects. Additionally, the fluorescence signal may be detected with a detector capable of energy resolution, such as with an energy dispersive spectrometer or a wavelength dispersive spectrometer. With such a detector, specific fluorescence signals may be optimized. For example, the object may be aligned until a specific fluorescence line from the structures or regions of interest is maximized, or until a fluorescence line that would be absent or minimally located at the structures or regions of interest is minimized. One practical example may be minimization of the silicon fluorescence line(s) when the structures of interest are periodic copper structures in a bulk silicon substrate.

Once the Talbot pattern has been aligned to illuminate the periodic structures, in the next step 4030 the desired quantity can be measured. The exact protocol will depend on the measurement desired. If, for example, the average thickness of the an ensemble of TSVs is the quantity to be measured, the TSVs are aligned to overlap with the Talbot anti-nodes. In this example, the transmission and absorption of the x-rays by the TVSs is measured and the average thickness can be determined using established method known in the art. If, for example, the size and size distribution of voids of small dimension in the ensemble of TSVs is the quantity to be measured, the small angle scattering pattern from the TSVs aligned with the anti-nodes of the Talbot pattern is measured and a known analysis method is used to determine the size and size distribution of the voids. If the sidewalls or coatings of the TSVs are of interest, the anti-nodes may be aligned with not the center of the TSV but instead two anti-nodes are aligned on each side of a TSV, allowing analysis of such things as sidewall roughness through known methods using small angle scattering.

If, on the other hand, the crystallinity or composition of the periodic object is to be determined, x-ray diffraction signal or x-ray fluorescence signal is measured. The 3D nature of the Talbot pattern (e.g., intensity variation along the z-direction (beam propagation direction) and the lateral direction can be utilized to analyze, measure, and characterize information around the periodic structures by scanning the object with respect to the Talbot pattern, for example in the z-direction along the Talbot fringe, so that the point of highest intensity moves through the periodic structures, and correlating the measured signal (such as x-ray diffraction intensity) with the depth where the brightest portion of the Talbot anti-node is positioned may allow a determination if the structures have a uniform crystallinity of a predetermined specification.

The data collection will typically be carried out using an x-ray detector with an array of pixels mounted at some distance from the object under examination when absorption, small angle scattering, diffraction, or reflectivity is measured, or an x-ray spectrometer is used when x-ray fluorescence is measured. X-ray intensity will be converted to electronic signals, which are then passed through a connecting cable or a wireless interface to a data storage and analysis system.

Once the measurements have been collected, in the next step 4040, the measurements are analyzed to calculate or otherwise derive the desired metric. This may be correlated to the physical dimensions of the object, the composition or crystal structure, the local presence or absence of stresses within the periodic object, etc.

This method can be applied to any number of measurement and detection applications, including but not limited to x-ray transmission or absorption measurements, small angle x-ray scattering (SAXS), x-ray fluorescence (XRF) detection, x-ray reflectance (XRR) measurements, and x-ray diffraction (XRD) measurements. Other applications of this method of exposure to x-ray illumination with a structured intensity pattern tuned to the periodicity of an object to be examined will be known to those skilled in the art.

Figure 42:
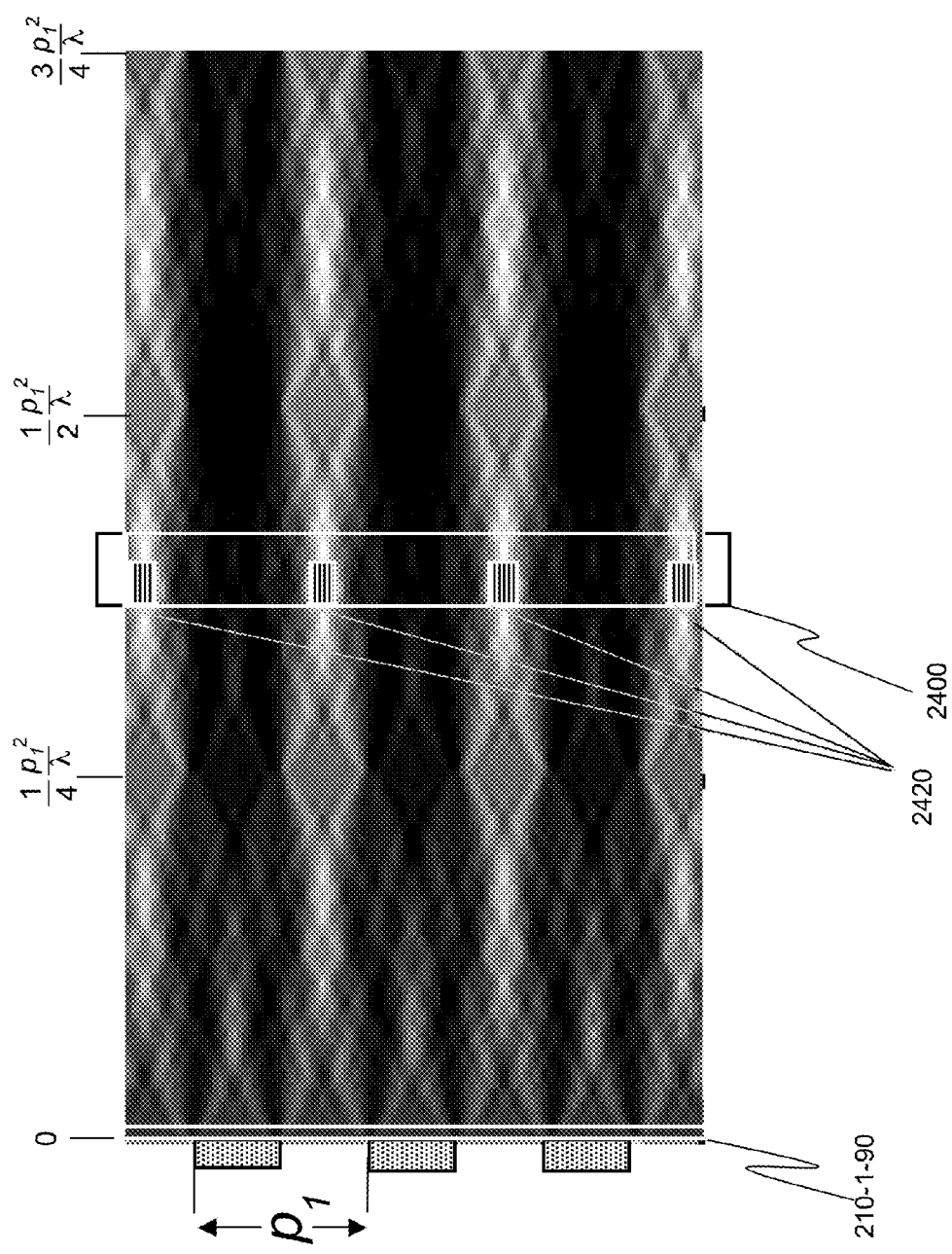
FIG. 42 illustrates a cross-section of the placement of an object comprising periodic structures is placed into a Talbot interference pattern according to the invention.

An example of one placement of an object 2400 comprising periodic features 2420 in a Talbot interference fringe pattern for a beam splitting grating 210-1-90 as may be used in some embodiments of the invention is shown in FIG. 42. The object 2400 is placed at a fractional Talbot distance such that the object features of interest 2420 are aligned with the anti-nodes (constructive interference regions of the interference pattern). This means x-rays effectively only interact with these periodic features 2420, while surrounding regions corresponding to the nodes (destructive interference regions of the pattern) produce no or a much diminished signal.

The Talbot pattern as illustrated in FIG. 42 corresponds to the intensity pattern for a beam splitting grating 210-1-90 having a 1:1 π/2 phase shifting pattern, as illustrated in, for example, "X-Ray Phase Imaging with Single Phase Grating" by Y. Takeda et al., *Jpn. J. Appl. Phys.* vol. 46, 2007, pp. L89-L91.

The periodic features and/or regions of interest of the object under examination may be aligned in a number of different ways, depending on the desired measurement results. For example, if the composition or dimensions of the features themselves are of interest, they should be centered on the anti-node of the Talbot interference pattern. If there are regions of interest such as the sides of a feature, the object under examination should be positioned such that the bright anti-nodes correspond to those regions. It should also be noted that there is a depth-sensitivity to this method. With a sufficiently thin sample, this method may be used to perform a depth-sensitive mapping of desired characteristics by moving the sample along the interference fringes.

One example of such a use is one in which a beam splitter is illuminated by an x-ray beam of adequate spatial coherence upstream, thus producing Talbot self-images and intensity patterns at defined distances (fractional and integer Talbot distances) downstream of the beam splitter. In this example, a planar sample to be imaged in a transmission geometry (plane of the sample is parallel to the diffractive grating) is placed at a distance downstream of the beam splitter in which there is a high-low intensity pattern due to the interference of the x-rays. If the beam splitting grating is of a phase-shifting type, it may be placed at one of the fractional Talbot distances, e.g.

$$D_N = N_a \frac{p_1^2}{8\lambda} = \frac{N_a}{16} D_T \qquad [\text{Eqn. 16}]$$

where $p_1$ is the period of the beam splitting grating, $D_N$ is the fractional Talbot distance for a plane wave illumination, $\lambda$ is the mean x-ray wavelength, and $N_5$ is the Talbot fractional order (N=1, 2, 3, . . . ) at which the detector is placed.

The pitch of the beam splitter may be selected as to match the pitch of the regions of interest (e.g. features or feature edges); this may be related to first order by the following relationship:

$$df = dg \cdot S\varphi \cdot M \qquad [\text{Eqn. 17}]$$

where df is defined as the pitch of the features or regions of interest, dg is the pitch of the diffractive grating, $S\varphi$ is the scaling factor (for phase-type diffractive gratings, $S\varphi$ is 1 for a π/2 phase shift and ½ for a π phase shift), and M is a magnification factor defined as $(L_1+L_2)/L_1$ where $L_1$ is the distance from the effective source spot to the diffractive grating and $L_2$ is the distance from the grating to the object under investigation.

Alignment of the periodic features of the object to be examined with the anti-nodes of the interference pattern and nodes (destructive interference) ensures that x-ray excitation only occurs at the bright anti-nodes, thus allowing illumination and subsequent measurement, characterization and analysis of only the regions and features of interest.

Figure 2:
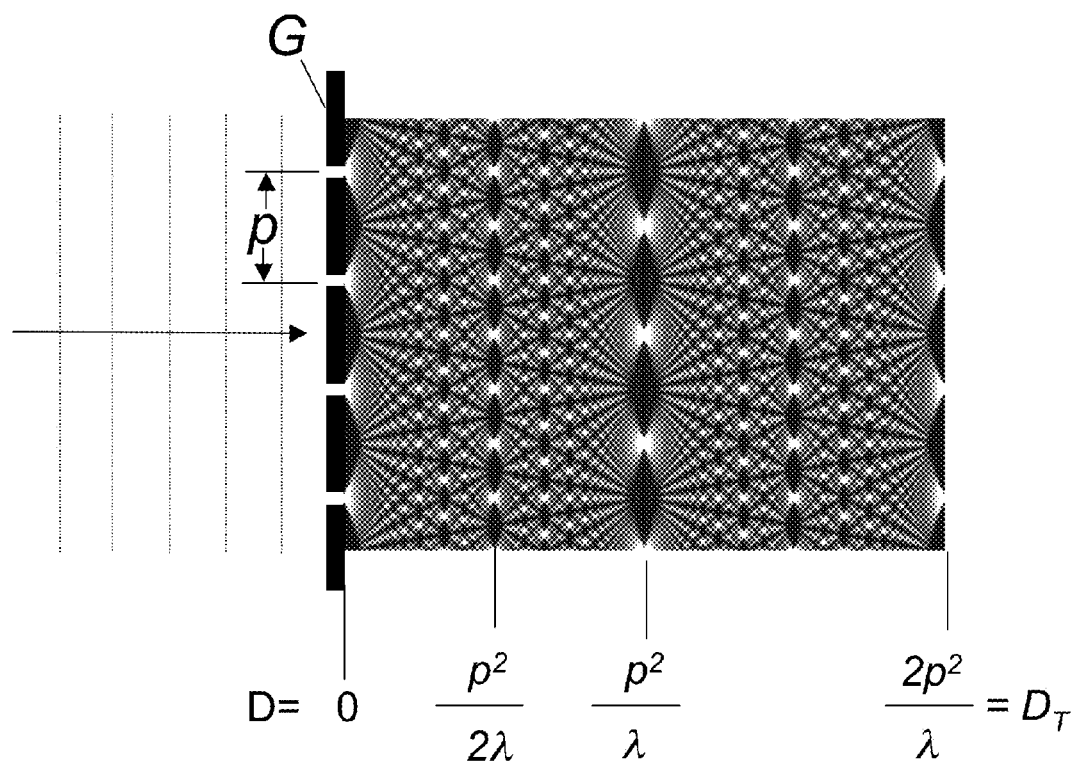
FIG. 2 illustrates a prior art Talbot interference pattern produced by a transmission grating.
Figure 3:
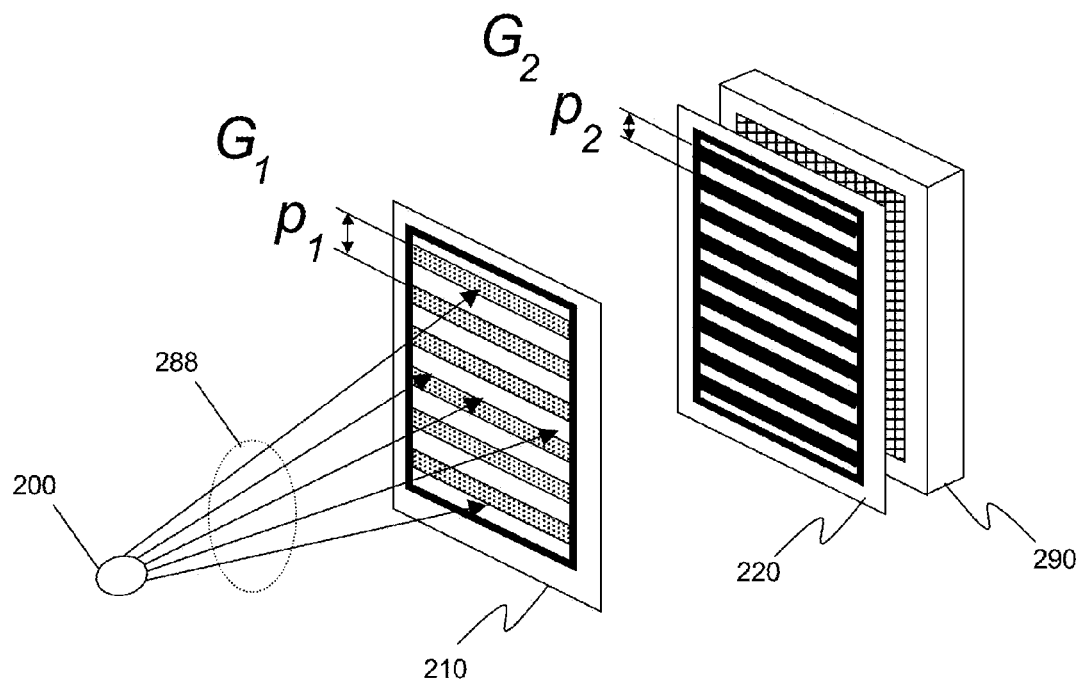
FIG. 3 illustrates a prior art x-ray grating interference system using a microfocus source.
Figure 43:
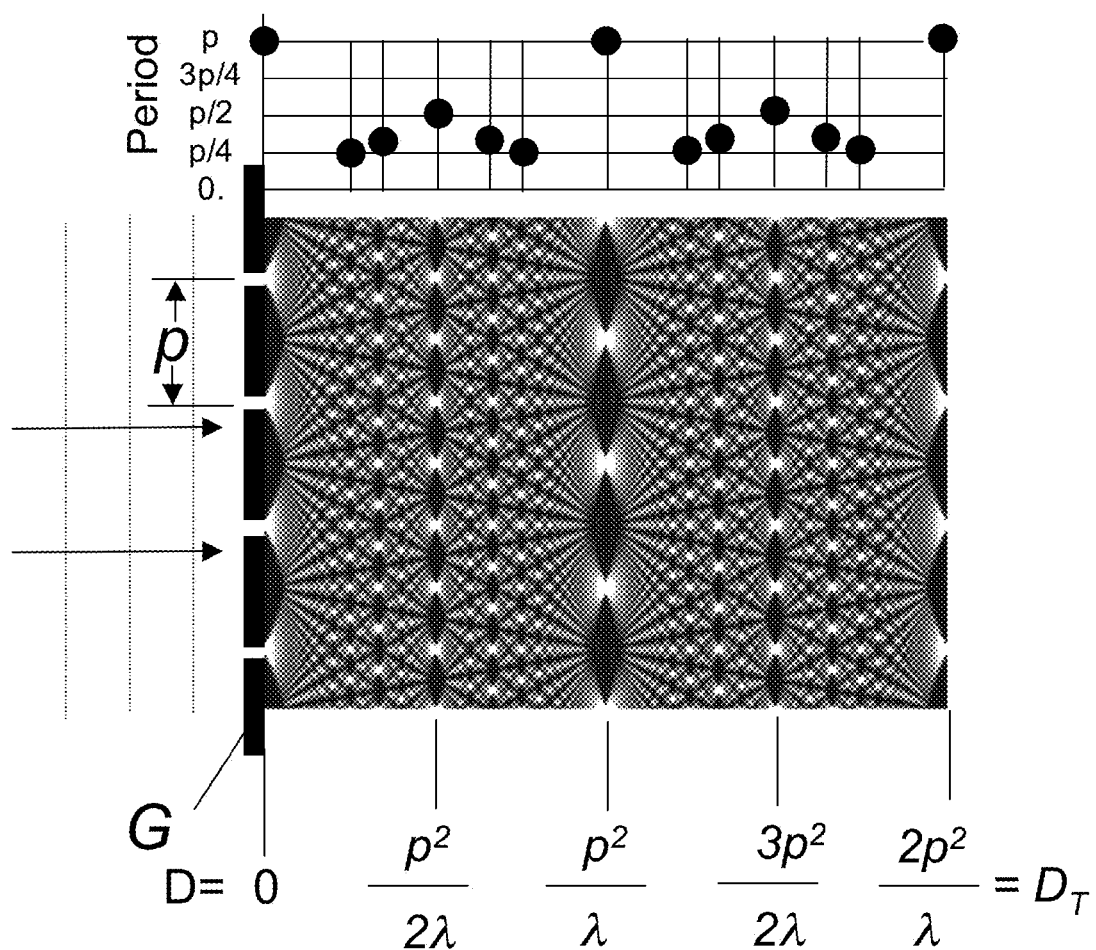
FIG. 43 illustrates the smaller periods available for the Talbot pattern of FIG. 2.

It should be noted that configurations may be used in which the structures manufactured on the beam splitting grating may be much larger than the periodic structures being examined, depending on the distance of the sample from the beam splitter. Illustrated in FIG. 43 are the Talbot fringes from FIG. 2, with the period of the interference fringes for some of the intermediate Talbot distances plotted above the figure (Note that the smallest period is 4 times smaller than the period of the beam splitting grating p).

At the Talbot distance $D_T$, the original grating pattern reproduces itself, with period p matching the original grating period. At half the Talbot distance $D_T/2$, the period is also p, but with the nodes and anti-nodes reversed. However, at a quarter of the Talbot distance $D_T/4$, the fringe period is p/2—half the value at the original grating. And, at half that (a Talbot distance of $D_T/8$), the fringe period is p/4. Therefore, structures at a pitch of 10 nanometers may be effectively illuminated according to the method of the invention by using a beam splitting grating with a period of 40 nanometers if a suitable selection of beam splitter is made.

It should also be noted that, in some circumstances, objects themselves may be able to act as beam splitting gratings. TSVs fabricated of copper may introduce a phase shift for x-rays, and an object comprising periodic TSVs may be used as a beam splitting grating with suitable coherent illumination. The resulting interference pattern itself may be used to infer various properties of the TSVs without requiring additional interaction with other objects or optical elements.

3.3. Embodiments as an Apparatus.

Additionally, an apparatus may be constructed to implement measurements based on the aforementioned method. Embodiments of this invention with respect to a measurement, characterization (e.g. metrology or inspection), and/or analysis apparatus may include:

a) an x-ray source system comprising an x-ray generator of sufficient spatial coherence or an x-ray source that when in combination with another element, such as an absorption grating, achieves sufficient spatial coherence;

b) a periodic diffractive optical element such as a diffractive grating preferably in transmission geometry that produces Talbot interference patterns when illuminated with an x-ray beam of sufficient spatial coherence;

c) one or more x-ray detector-analyzer systems, of type depending on the desired x-ray information to be obtained, such as position-sensitive detectors known to the art or x-ray spectrometers known to the art;

d) means for aligning periodic features of an object to be examined with respect to the interference pattern, e) means for recording the information detected; and f) means for analysis of the recorded information.

To achieve the Talbot effect, the x-ray source system must provide an illuminating x-ray beam of sufficient spatial coherence, which may be achieved a method already known to those versed in the art, including a high brightness microfocus/nanofocus source using a solid target or liquid metal jet target. Alternatively, the source may comprise a microstructured anode or linearly accumulating sub-sources, similar to those described above.

In several embodiments of the invention, a means of generating Talbot interference fringes in one direction or an interference pattern in two orthogonal directions by use of a diffractive element (preferably a phase-type periodic grating) is employed. The diffractive element may be a diffractive grating comprising phase shifting portions that splits the x-ray beam by advancing or retarding the phase of x-rays passing through the grating lines, or absorptive in nature, to result in periodic spatial modulation in the amplitude, the phase, or both amplitude and phase of the resultant wave front.

Figure 44:
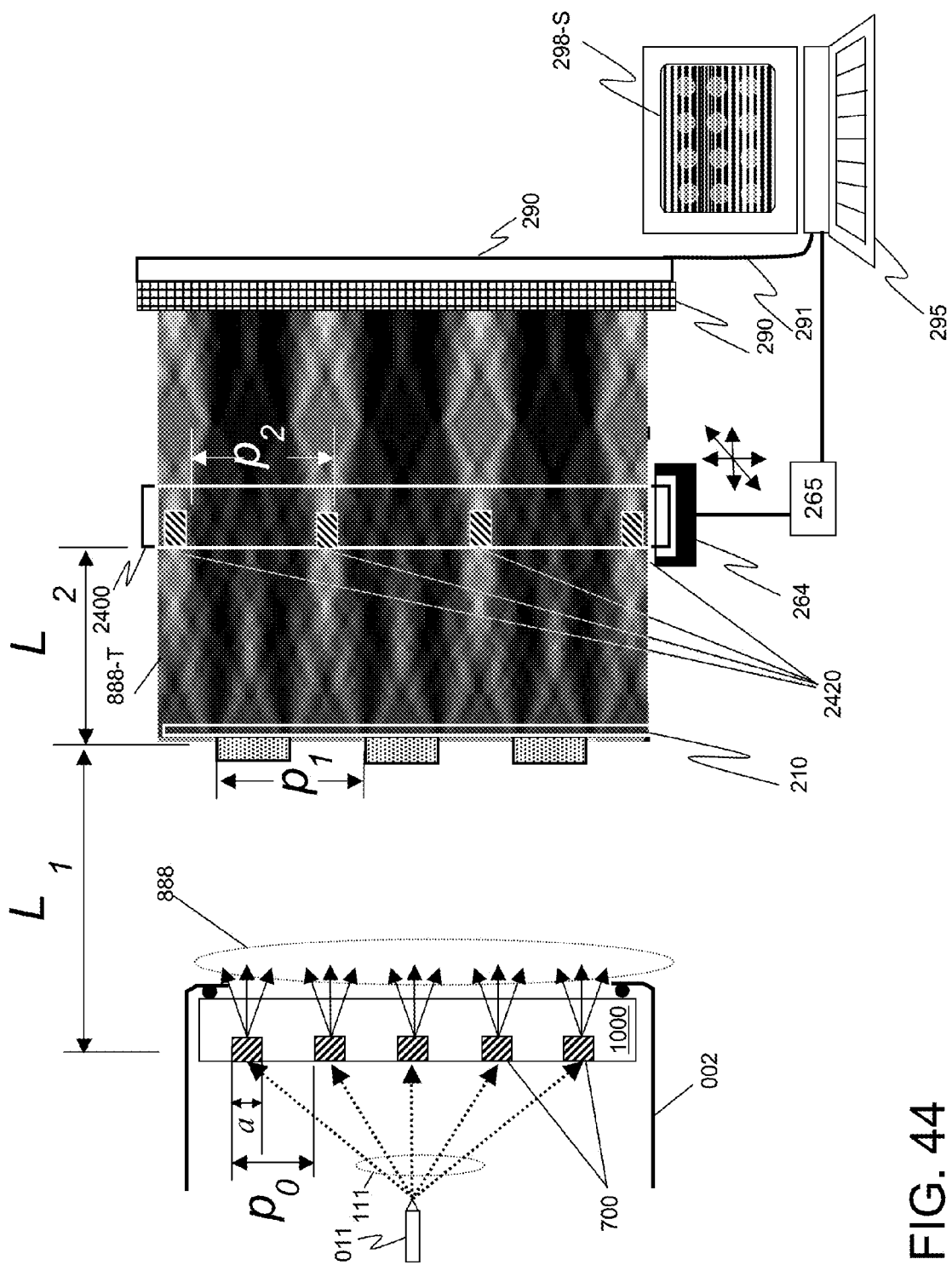
FIG. 44 schematically illustrates a cross-section of a system according to the invention in which an object comprising periodic structures is placed into a Talbot interference pattern.

In several embodiments of a metrology or characterization apparatus using the Talbot-based probing method will have components as illustrated in FIG. 44, The system typically comprises:

an x-ray source 002 that produces x-rays 888, a diffractive element 210 comprising an x-ray beam splitter of periodicity $p_1$, a sample holder 264 that is placed at or may be controlled by a controller 265 to move an object to be examined 2400 to be positioned at fractional or integer Talbot distance, and also align the periodic structures of the object to be positioned in a predetermined manner with respect to the periodic Talbot interference fringes, and an x-ray detector/analyzer system 290.

In such embodiments, the x-ray source 002 must produce x-rays of sufficient coherence for the Talbot interference fringes of high contrast (e.g. contrast greater than 20%) to be produced. This x-ray source may a conventional x-ray source, such as a high brightness microfocus/nanofocus source, or small focus liquid metal jet source, or, as was illustrated in FIG. 7, an extended source 300 with a multi-slit grating (absorption grating) 308 placed in front of it to produce an array of small coherent x-ray sources. Alternatively, the source may be an x-ray generator 002 that comprises a linear or 2D array of microstructures 700 comprising material or materials that produce x-rays of desired characteristics that are embedded in a second material 1000 of high thermal conductivity. Examples of such a source has already been described above, and in more detail in the previously mentioned US Patent Application entitled X-RAY SOURCES USING LINEAR ACCUMULATION by the inventors of the present invention (U.S. patent application Ser. No. 14/490,672 filed Sep. 19, 2014).

FIG. 44 is a schematic illustration of an embodiment of the disclosed x-ray characterization apparatus; the x-ray characterization system shown can be used to obtain any combination of x-ray information of interest, including XRF, XRD, imaging, and SAXS. FIG. 44 comprises a microstructured anode source comprising a substrate 1000 with microstructures 700 of x-ray generating material. The x-ray beam 888 of high spatial coherence illuminates a diffraction grating 210 positioned a distance $L_1$ from the source 002. At a Talbot distance $L_2$ downstream of the grating, the object 2400 is placed so that its features or regions of interest 2420 are aligned with the anti-nodes of the Talbot intensity pattern. Note that the periodicity of these regions $p_2$ is related to the periodicity of the diffraction grating $p_1$ by $$p_2 = p_1 \cdot S\varphi \cdot \frac{L_1 + L_2}{L_1} \qquad \text{[Eqn. 18]}$$

where $S\varphi$ is the scaling factor (for phase-type diffractive gratings, $S\varphi$ is 1 for a $\pi/2$ phase shift and ½ for a $\pi$ phase shift) and can depend on the type of the grating as well as well as the Talbot distance.

Additionally, in some of the embodiments, the diffraction element is a phase grating and is most preferably designed to cause a fractional or integer $\pi$ shift, such as $\pi/4$, $\pi/2$, $\pi$, or $3/2\pi$, etc. As in the method, the sample is preferably located a fractional or integer distance downstream of the diffraction element. Additional embodiments may comprise more than one of the above capabilities, in any combination. This can be accomplished through use of additional detectors and incorporation of optics that can be included or removed. An example of source and detector configurations for such a multi-purpose metrology system has been presented by Boris Yokhin et al. (U.S. Pat. No. 7,551,719).

3.4. A Embodiment Apparatus Using Small Angle X-Ray Scattering (SAXS).

Figure 45:
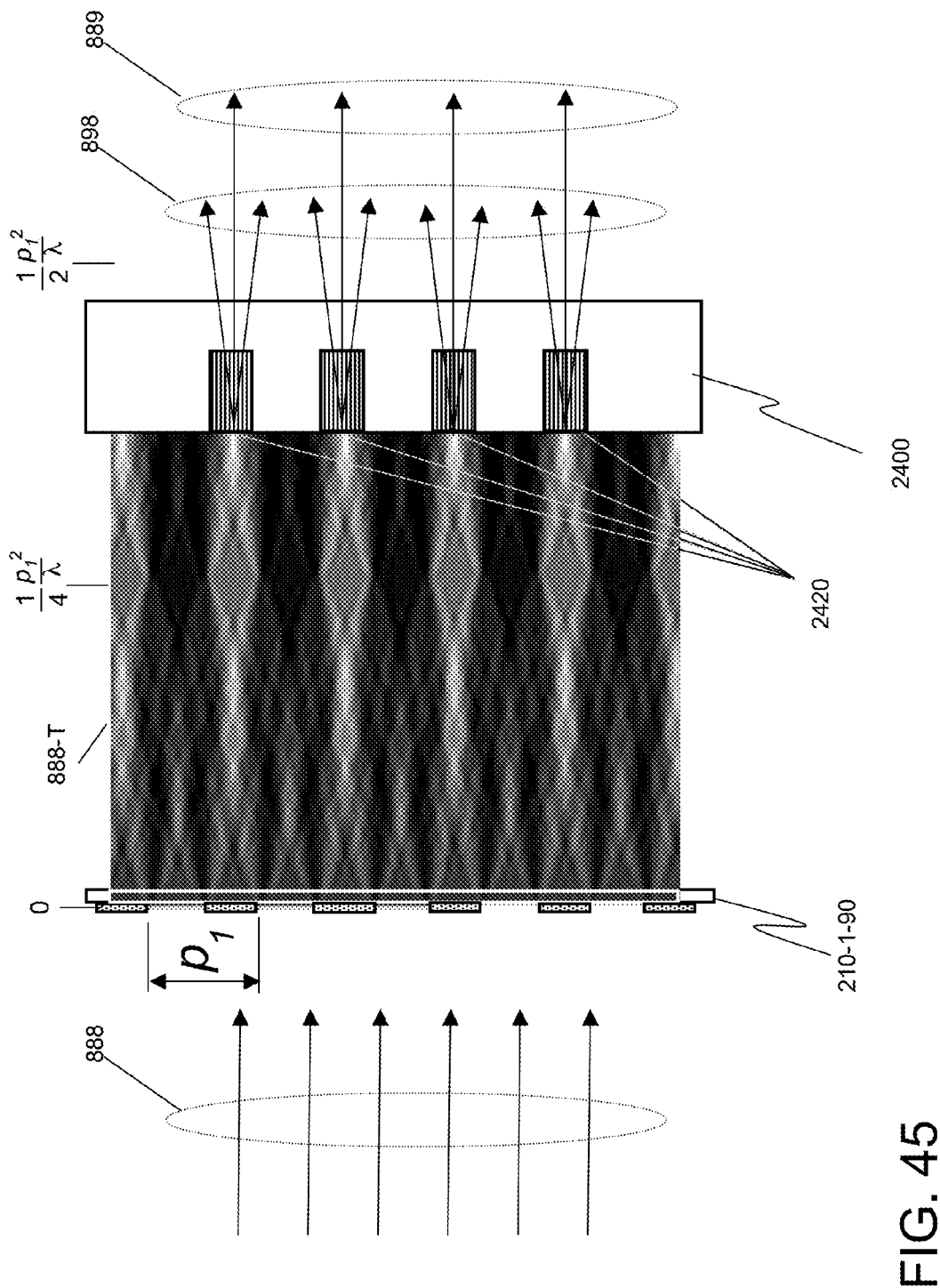
FIG. 45 schematically illustrates an object in a Talbot interference pattern producing small angle x-ray scattering.
Figure 46:
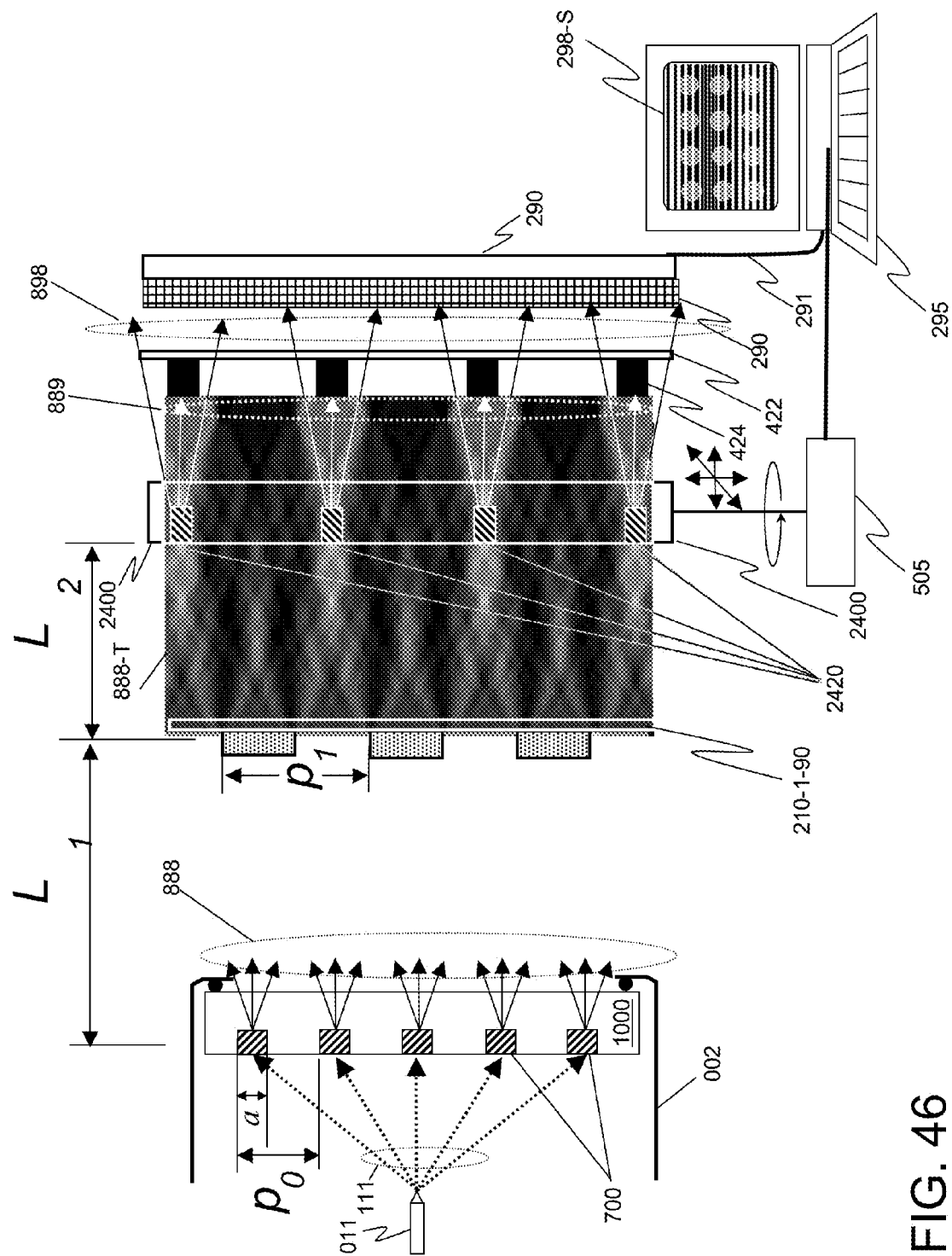
FIG. 46 illustrates a schematic in cross-section of a system according to the invention in which an object in a Talbot interference pattern produces small angle x-ray scattering.

FIGS. 45 and 46 show a schematic illustration of embodiments of the invention in which the periodic microbeams of the disclosed apparatus are used to obtain small angle x-ray scattering (SAXS) information from regions or features of interest.

In this embodiment, coherent x-rays 888 from an x-ray source 002 illuminate a phase grating 210-1-90. An optional aperture or collimating system (e.g. one or more apertures or slits) may be placed before or after the phase grating. The x-rays 888 form a Talbot interference pattern 888-T after interacting with the grating 210-1-90. The object 2400 comprising periodic structures 2420 is aligned such that the structures 2420 of interest are coincident with the Talbot pattern anti-nodes, and produce small angle x-ray scattering. The scattered x-rays 898 are detected by a detector 290, which will typically be a position-sensitive type well known in the art. An optional beam stop 422 with regions 424 that absorb x-rays may be employed to block the detection of transmission of primary x-rays 889 that are not scattered. For some embodiments of the system, small angle scattering of x-rays 898 up to 50 milliradians may be detected by the detector, while the beam stop 422 will block a range of angles from 0 radians to an angle dictated by the geometric arrangement of the system. For example, if the detector is 1 meter away from the object, and the overall illuminated area is 100 microns in diameter, then the beam stop will need to block from 0 milliradians to at least up to 0.1 milliradians, and possibly a larger number, to eliminate all directly transmitted (not scattered) x-rays. In some embodiments, the beam stop 422 is replaced with a single uniform beam stop placed close to the detector and is designed to stop directly transmitted x-rays.

In some embodiments, the object 2400 to be examined may be mounted on a mount, and rotated or translated by a stage, 5-axis mount 505, or goniometer.

It should be noted that these embodiments as illustrated are not to scale, as the divergence, collimation, or convergence of the Talbot interference pattern will depend on how well collimated the x-ray beam is and how far the object is placed from the source.

3.5. A Embodiment Apparatus Using X-Ray Fluorescence

Figure 47:
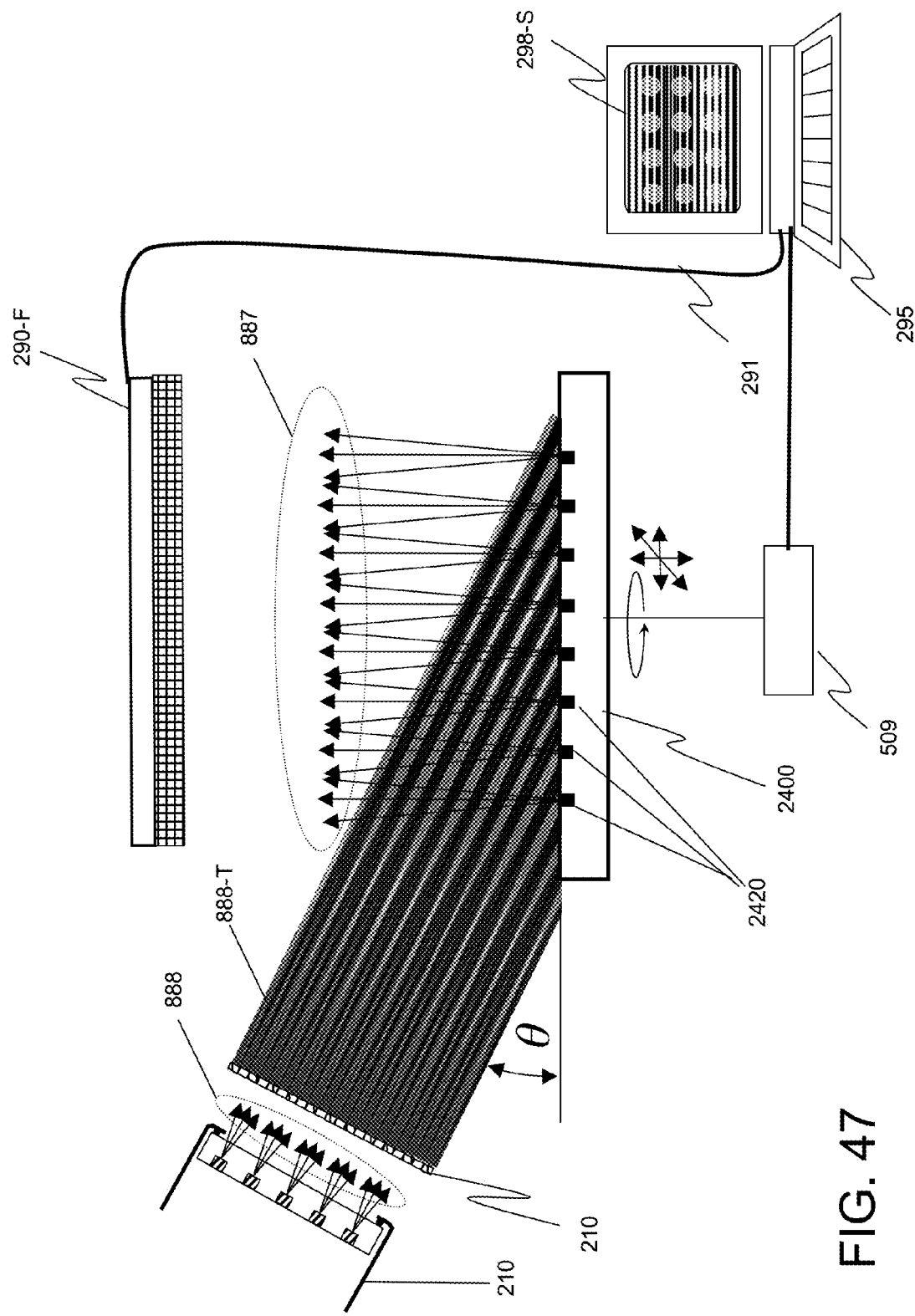
FIG. 47 illustrates a schematic in cross-section of a system according to the invention in which an object in a Talbot interference pattern produces x-ray fluorescence at grazing incidence.

FIG. 47 is a schematic illustration of an embodiment of the invention in which the disclosed apparatus is used to obtain x-ray fluorescence information from periodic regions within the object under examination. In this embodiment, the geometry is arranged to conform to a total x-ray fluorescence (TXRF) configuration. As in the previously described embodiments, the x-ray source 002 illuminates a phase grating 210 and forms a Talbot interference pattern 888-T after interacting with the grating 210. The object 2400 comprising periodic structures 2420 is aligned such that the structures 2420 of interest are coincident with the Talbot pattern anti-nodes, and produce x-ray fluorescence 887. As illustrated, the Talbot fringes intersect the object 2400 at an angle $\theta$ that is near grazing incidence for the material of the object, although other angles of incidence may also be used. The x-ray fluorescence 887 is then detected by a detector 290-F, positioned at some predetermined distance away from the object.

As illustrated, the Talbot interference pattern is a 3-D structure filling a volume of space, and as such, the periodic structures of the object are not positioned at the same Talbot distance. A more practical embodiment may be to use a 2-D Talbot pattern, in which the Talbot pattern is in the form a sheet, and illuminates the object with a 1-D line of x-rays. This allows the periodic structures to all be illuminated by the same Talbot fringe, since all features are the same distance from the beam splitting grating.

In some embodiments, the object 2400 to be examined may be rotated or translated by rotating or translating the object with a stage, 5-axis mount or goniometer 509.

In variations on this embodiment, an x-ray source system of either a microstructured source, a source comprised of linearly accumulating sub-sources, small focus source, or an extended source combined with a multi-slit may be used to illuminate the beam splitter and form a Talbot interference pattern that is incident on an object. Optionally, an optic and a monochromator may be placed between the source and the beamsplitter. This system may be horizontal or vertical. It may be oriented as shown at an small angle of incidence $\theta$, or with an angle of incidence near or at 90°. The detector may be offset to collect x-ray fluorescence emanating from the sample at an angle or alternatively, receive the fluorescence signal after reflection by an optic or multilayer. The detector may be of a wavelength or energy sensitive type such as silicon drift detectors, scintillation detectors, and proportional counters.

In some embodiments, the detector may be placed on the same side of the object as the x-ray source. In this configuration, the detector preferably is a silicon drift detector with a hole through the middle, but may be any energy or wavelength sensitive spectrometer. An optional x-ray optical element may be used, placed at a Talbot distance downstream of a beam splitter. Such an optic is preferably a reflective capillary x-ray optic such as an ellipsoidal monocapillary. Alternatively, an aperture or collimating component can be used instead of the optical element. The x-rays that are collimated or focused illuminate the object at periodic regions. Fluorescent x-rays produced by the object are then collected by a detector placed near the object to be investigated to maximize the solid angle of collection. The x-ray optical elements, configurations and systems that may be applied to embodiments of the invention have been described more fully in the co-pending U.S. Patent Application entitled X-RAY ILLUMINATORS WITH HIGH FLUX AND HIGH FLUX DENSITY by the inventors of the present invention (U.S. patent application Ser. No. 14/544, 191 filed Dec. 5, 2014), and in X-RAY SURFACE ANALYSIS AND MEASUREMENT APPARATUS by the inventors of the present invention (U.S. patent application Ser. No. 14/634,834 filed Mar. 1, 2015), which are both hereby incorporated by reference in their entirety.

3.6. A Embodiment Apparatus Using X-Ray Reflectance

Other embodiment of the invention in which the disclosed apparatus is used to obtain x-ray reflectance information from periodic regions within the object under examination. In this embodiment, the geometry is arranged to conform to an x-ray reflectance (XRR) configuration. As in the previously described fluorescence embodiments, the x-ray source illuminates a phase grating and forms a Talbot interference pattern after interacting with the grating. As in some of the previously described embodiments, an optional focusing or collimating system may be employed to create a predetermined wavefront profile (converging, diverging, or collimated) for the Talbot interference pattern. This focusing or collimating system may additionally be either bandwidth limiting or monochromatizing by inclusion of filtering, monochromatizing, etc. elements. The focusing system may also be placed before or after (preferably at a Talbot distance from) the phase grating The object comprising periodic structures is aligned such that the structures of interest are coincident with the Talbot pattern anti-nodes, and x-rays are reflected from the illuminated surface of the periodic structures. The reflected x-rays are then detected by a detector positioned at some predetermined distance away from the object.

3.7. A Embodiment Apparatus Using X-Ray Diffraction

Figure 48:
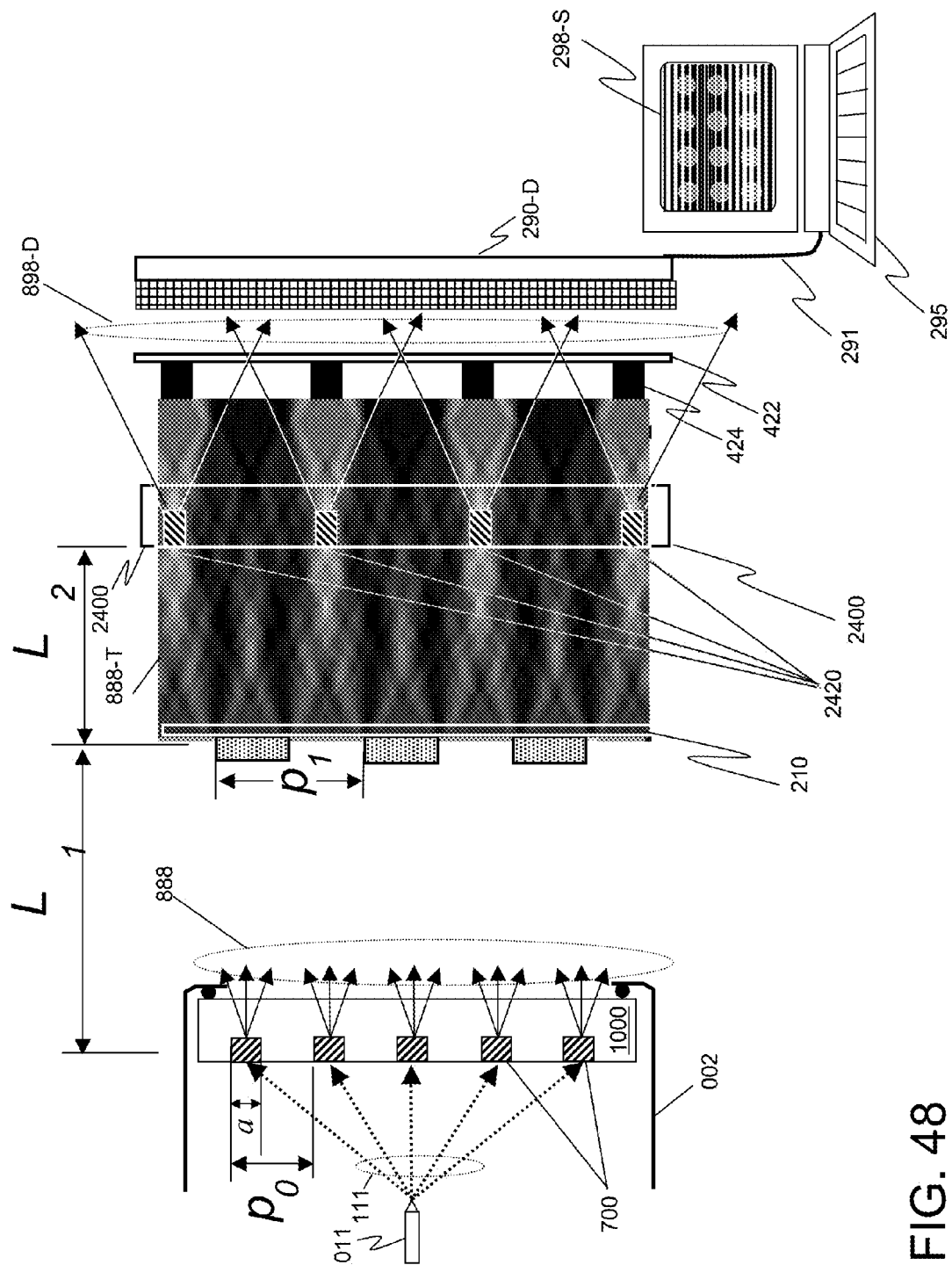
FIG. 48 illustrates a schematic in cross-section of a system according to the invention in which an object in a Talbot interference pattern produces x-ray diffraction.

FIG. 48 shows a schematic illustration of an embodiment of the invention in which the periodic microbeams of the disclosed apparatus are used to obtain x-ray diffraction (XRD) information from periodic structures or features of interest. An example of an x-ray diffraction embodiment having a transmission geometry is shown in FIG. 48, while other embodiments may having a grazing incidence/reflection geometry.

In the embodiment of FIG. 48, the x-ray source 002 (shown to be a microstructured anode source, but which can alternatively be an extended source with a source grating or any other x-ray generator with sufficient spatial coherence) illuminates a phase grating 210. An optional aperture or collimating system (e.g. one or more apertures or slits) may be placed before or after the phase grating. The x-rays 888 form a Talbot interference pattern 888-T after interacting with the grating 210. The object 2400 comprising periodic structures 2420 is aligned such that the structures 2420 of interest are coincident with the Talbot pattern anti-nodes, and produce x-ray diffraction 898-D. The diffracted x-rays 898-D are detected by a detector 290-D, which will typically be a position-sensitive type well known in the art. An optional beam stop 422 with regions 424 that absorb x-rays may be employed to block the detection of transmission of primary x-rays that are not diffracted.

3.8. Combinations of Embodiments.

Although apparati have been described using periodic structured illumination, such as Talbot interference fringes, to produce signals related to small angle x-ray scattering, x-ray fluorescence, x-ray reflectance and x-ray diffraction, these measurement systems are not mutually exclusive, and may be combined to collect information serially or in parallel. The descriptions presented here are not meant to be limiting, and combinations of these embodiments will be apparent to those skilled in the art.

4. Fabrication of Gratings

Fabrication of the gratings used in embodiments of the invention may be made using known prior art fabrication processes such as those previously described by Christian David [C. David et al., "Fabrication of diffraction gratings for hard x-ray phase contrast imaging", *Microelectron. Eng.* 84, 1172-1177, 2007].

Gratings for x-rays may be fabricated using silicon substrates, with etched changes in topography to induce phase changes and depositions of a higher Z material, such as gold (Au, Z=79), to induce absorption changes. The x-ray absorption properties for gold and silicon are illustrated in FIG. 39.

Figure 49:
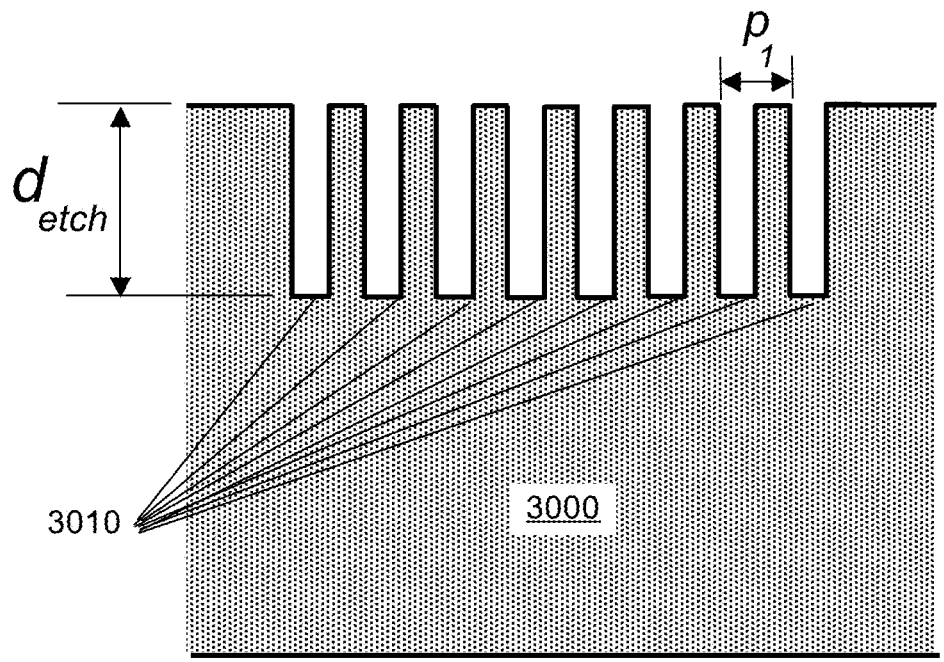
FIG. 49 illustrates a possible structure of an x-ray phase grating according to some embodiments of the invention.

As shown in FIG. 49, a periodic pattern 3010 may be etched into a silicon substrate 3000 to create a structure which introduces a periodic phase shift for x-rays falling at normal incidence. The phase shift depends on the etch depth, with a phase-shift of $\pi$ radians for normal incidence x-rays achieved when the following condition is met:

$$d_{etch} = \frac{1}{2} \frac{\lambda}{|n-1|} = \frac{1}{2} \frac{\lambda}{\delta} \quad [\text{Eqn. 19}]$$

Values for $\delta$ for silicon at several x-ray energies, along with the depth etched structures need to a phase-shift of $\pi$ radians are shown in Table IV.

A typical grating fabrication process comprises coating a <110> oriented silicon wafer with a photoresist, and patterning the resist using conventional photolithography, focused ion beam lithography, or electron beam lithography. The silicon then undergoes an etching process such as wet etching in, for example, a potassium hydroxide (KOH) solution, or reactive ion etching (RIE), with the etching selectively occurring only for portions of the silicon not masked by the resist. The etch depth may be controlled by adjusting the time of the etch process. Other variations of the etching process will be known those skilled in the art of semiconductor processing and manufacturing.

TABLE IV

Etch depth for Silicon phase shift of $\pi$ radians.

| X-ray Energy (keV) | Wavelength $\lambda$ (nm) | $\delta$ | $\pi$ phase shift depth (μm) |
|---|---|---|---|
| 3.0 | 0.413 | 5.43E−05 | 3.81 |
| 5.0 | 0.248 | 1.98E−05 | 6.26 |
| 8.048 (Cu Kα) | 0.154 | 7.58E−06 | 10.17 |
| 10.0 | 0.124 | 4.89E−06 | 12.69 |
| 17.48 (Mo Kα) | 0.0709 | 1.59E−06 | 22.36 |
| 30.0 | 0.0413 | 5.36E−07 | 38.52 |
| 50.0 | 0.0248 | 1.93E−07 | 64.31 |
| 59.39 (W Kα) | 0.0209 | 1.37E−07 | 76.32 |
| 100.0 | 0.0124 | 4.82E−08 | 128.74 |

Figure 50:
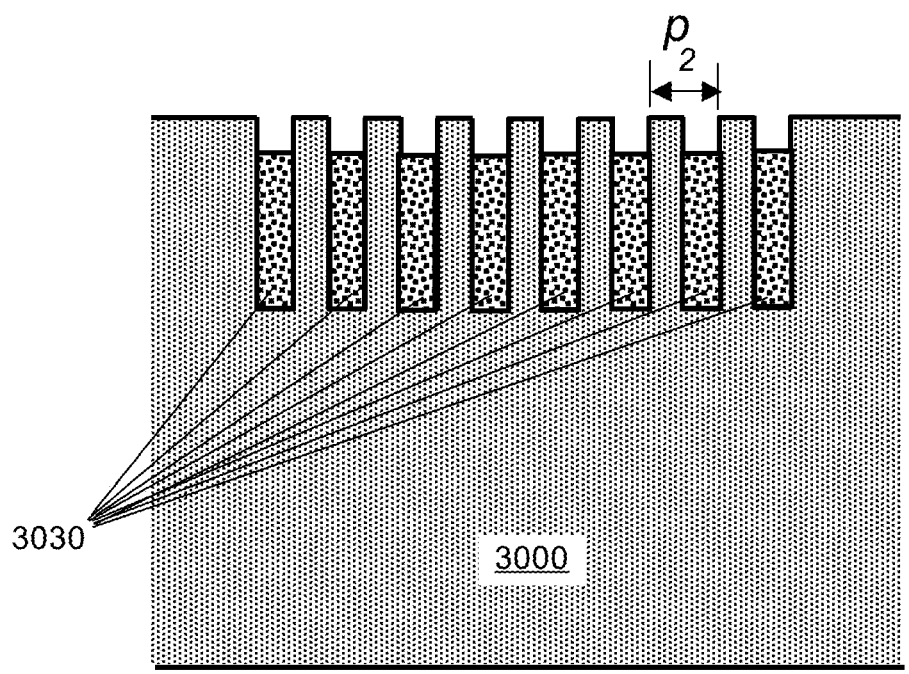
FIG. 50 illustrates a possible structure of an x-ray absorption grating according to some embodiments of the invention.

Absorption gratings such as those used for $G_2$ may be fabricated by initially crating a silicon phase grating, as described above, and then depositing an x-ray absorbing material, such as gold, into the grooves already patterned in the silicon. This is illustrated in FIG. 50, in which an amount of x-ray absorbing material 3030 such as gold has filled the grooves created in a silicon substrate 3000. One process for the deposition of gold into the silicon grooves involves a standard electroplating processes. To ensure that gold is only deposited into the grooves, a sacrificial layer of aluminum may initially deposited at an angle, and a seed layer ~50 nm thick comprising Chromium (Cr) and gold (Au) are then deposited. A phosphoric acid treatment removes the all the material deposited on the tops of the silicon structures, leaving seed material only in the bottom of the grooves in the silicon. Standard electroplating may follow, with growth of gold occurring only onto the deposited seed layers. Deposition of gold at hundreds of microns can create absorption gratings with a transmission modulation of 75% or more. Absorption will, however, depend on the x-ray energy and the absorption coefficient for the material, as was illustrated in FIGS. 1 and 39. Other methods for making x-ray absorption gratings will be known to those skilled in the art.

For some applications and for certain x-ray wavelengths, crystal gratings may also be used.

5.0 Detector Properties

The detector may be any one of a number of detectors used to form x-ray images. One type of commonly used x-ray detector comprises a fluorescent screen or scintillator, such as one comprises a layer of cesium iodide (CsI), thallium doped CsI, yttrium aluminium garnet (YAG) or gadolinium sulfoxylate (GOS), that emits visible photons when exposed to x-rays. The visible photons are then detected by an electronic sensor that converts visible intensity into electronic signals, often with the additional formation of a relay image using visible optics that enlarge and magnify the intensity pattern of the photons emitted by the fluorescent screen. With the relay optics, the electronic detector need not comprise a high resolution sensor itself, and inexpensive commercial CCD detectors or complementary metal-oxide-semiconductor (CMOS) sensor arrays with, for example, 1024×1024 pixels, each 24 μm×24 μm square, may be used.

Commercial flat panel digital x-ray sensors in which a layer of scintillator material is placed in close proximity to (or even coated onto) an array of conventional optical image sensors are manufactured by, for example, Varian Inc. of Palo Alto, Calif. and General Electric, Inc. of Billerica, Mass. Other configurations of image sensors may be known to those skilled in the art. In embodiments in which a G2 analyzer grating is used, it is preferable to use highly efficient, fast read-out detectors such as flat panel detectors, used for medical and industrial uses. For many applications, a flat panel detector with a resolution larger than 20 microns will require that an analyzer grating $G_2$ with a period equal to the Talbot fringe period to be placed in the x-ray beam path before the detector.

A second approach is to use an electronic sensor that directly creates an electrical signal in response to the absorption of x-rays, by, for example, the creation of direct electron-hole pairs in amorphous selenium (a-Se). These are then converted into electronic signals using an array of thin-film transistors (TFTs). Such direct flat panel detectors (FPDs) such as the Safire FPD of Shimadzu Corp. of Kyoto, Japan, are commercially available.

6.0. Variations

Embodiments may further comprise other components typically included in Talbot interferometer, including spectral filters to obtain a desired x-ray energy bandwidth and positioning control systems for all the various components of the system.

It should be noted that certain terms used within this disclosure will be well known to those skilled in the art, such as grids or gratings. In the descriptions here, grids and gratings are terms that may be used interchangeably, and are not meant to be restrictive to a particular grid, period, or pattern.

Likewise, it should be noted that certain terms used within this disclosure will be well known to those skilled in the art, such as Talbot fringes, interference patterns, or "carpets". In the descriptions here, interference patterns, fringes, or "carpets" are terms that may be used interchangeably, and are not meant to be restrictive to any particular intensity pattern.

Likewise, it should be noted that, although these methods and systems are intended for use with periodic structures, the structures need not be uniformly periodic to achieve a useful benefit. Gridded structures which are missing certain rows or columns of an array may still provide a useful signal, as will quasi-periodic structures, such as those formed using directed self-assembly (DSA). As long as a portion of the structures are generally periodic to some degree, the methods and systems of the invention may be employed.

With this application, several embodiments of the invention, including the best mode contemplated by the inventors, have been disclosed. It will be recognized that, while specific embodiments may be presented, elements discussed in detail only for some embodiments may also be applied to others.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. A method for examining an object with periodic structures, comprising:
   selecting an object with periodic structures for examination;
   determining a volume in which a Talbot interference pattern will be formed,
      said Talbot interference pattern to be formed using
         a source of x-rays and
         an x-ray beam splitting grating,
      and to be matched in dimension and pitch
         to the object with periodic structures to be examined;
   placing the object having periodic structures into said volume;
   establishing the Talbot interference pattern;
   aligning the periodic structures of the object
      with the anti-nodes of the Talbot interference pattern; and
   detecting an x-ray signal resulting from the interaction
      of the Talbot interference pattern
      and the periodic structures of the object.

2. The method of claim 1, in which
   the x-ray signal is a signal arising from transmission of x-rays through the periodic structures.

3. The method of claim 1, in which
   the x-ray signal is a signal arising from small angle x-ray scattering.

4. The method of claim 1, in which
   the source of x-rays is a microfocus source.

5. The method of claim 1, in which
   the source of x-rays is an extended source used in conjunction
   with an absorbing grating comprising periodic apertures.

6. The method of claim 1, in which
   the source of x-rays comprises:
   a vacuum chamber;
      an emitter for an electron beam; and
      an x-ray target comprising:
         a substrate comprising a first material and, embedded in the substrate,
         at least a plurality of discrete structures comprising a second material selected
            for its x-ray generating properties,
         and in which said plurality of discrete structures
            are arranged to form a periodic pattern of sub-sources.

7. The method of claim 6, in which
   the first selected material is selected from the group consisting of:
   beryllium, diamond, graphite, silicon, boron nitride, silicon carbide, sapphire and diamond-like carbon; and
   the second material is selected from the group consisting of:
   iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead and combinations and alloys thereof.

8. The method of claim 1, in which
   the x-ray beam splitting grating comprises structures to introduce a phase-shift of approximately ● radians for a predetermined x-ray wavelength.

9. The method of claim 1, in which
   the x-ray beam splitting grating comprises structures to introduce a phase-shift of approximately $\pi/2$ radians for a predetermined x-ray wavelength.

10. The method of claim 1, in which
the x-ray beam splitting grating comprises
an x-ray phase-shifting grating, in which
the period $p_1$ of the x-ray phase-shifting grating is less than or equal to the lateral coherence length of the x-rays from the x-ray source.

11. The method of claim 1, in which
matching the Talbot interference pattern
to the object having periodic structures to be examined comprises
selecting the x-ray beam splitting grating so that the anti-nodes of the Talbot interference pattern have the same pitch to overlap the periodic structures of the object.

12. The method of claim 1, in which
matching the Talbot interference pattern
to the object having periodic structures to be examined comprises
selecting the x-ray beam splitting grating so that the anti-nodes of the Talbot interference pattern have a pitch that is an integer multiple of the periodic structures of the object and will overlap a subset of the periodic structures of the object.

13. The method of claim 12, in which
the object having periodic structures is selected from the group consisting of:
a semiconductor wafer, an integrated circuit, and
a packaging component for an integrated circuit; and
the x-ray signal provides information that leads to a determination of at least one of the properties of the periodic structures of the object selected from the group consisting of:
critical dimensions, sidewall angle, pitch, and linewidth roughness.

* * * * *